United States Patent
Volosin et al.

(10) Patent No.: US 12,406,761 B2
(45) Date of Patent: Sep. 2, 2025

(54) SYSTEMS AND METHODS FOR PROVIDING AND MANAGING A PERSONALIZED CARDIAC REHABILITATION PLAN

(71) Applicant: ZOLL Medical Corporation, Chelmsford, MA (US)

(72) Inventors: Kent Volosin, Mars, PA (US); Jason T Whiting, Gibsonia, PA (US); Rachel H Carlson, Falls Creek, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 18/426,746

(22) Filed: Jan. 30, 2024

(65) Prior Publication Data
US 2024/0257939 A1    Aug. 1, 2024

Related U.S. Application Data

(63) Continuation of application No. 16/943,099, filed on Jul. 30, 2020, now Pat. No. 11,942,203.
(Continued)

(51) Int. Cl.
*A61B 5/00* (2006.01)
*A61B 5/0205* (2006.01)
(Continued)

(52) U.S. Cl.
CPC .......... *G16H 20/30* (2018.01); *A61B 5/0006* (2013.01); *A61B 5/0205* (2013.01); *A61B 5/349* (2021.01);
(Continued)

(58) Field of Classification Search
None
See application file for complete search history.

(56) References Cited

U.S. PATENT DOCUMENTS

| 6,006,119 A | 12/1999 | Soller et al. |
| 6,212,427 B1 | 4/2001 | Hoover |
(Continued)

FOREIGN PATENT DOCUMENTS

WO    2002062211    8/2002

OTHER PUBLICATIONS

PCT Search Report and Written Opinion for PCT Application No. PCT/US2020/044190, dated Oct. 14, 2020, 22 pages.

*Primary Examiner* — Shirley X Jian
(74) *Attorney, Agent, or Firm* — ZOLL Medical Corporation

(57) ABSTRACT

A system for managing an individualized cardiac rehabilitation plan for an ambulatory cardiac rehabilitation patient includes an externally worn device configured to monitor cardiac activity of the patient and a server in communication with the externally worn device. The server includes a computer-readable medium and at least one server processor configured to receive one or more inputs from a healthcare provider, develop a patient-specific cardiac rehabilitation plan, including a plurality of exercise sessions, based on the one or more inputs, transmit the rehabilitation plan to the externally worn device, receive patient data from the externally worn device, and record one or more status identifiers for each past exercise session based on the received patient data. The at least one server processor is configured to adjust the rehabilitation plan based on the one or more recorded status identifiers and transmit the adjusted rehabilitation plan to the externally worn device.

19 Claims, 28 Drawing Sheets

Exercise Performance Data Structure 1100

| | Overall Plan Data Fields 1105 | Individual Exercise Fields 1110 | |
|---|---|---|---|
| 1105a | Plan A | Aerobic | 1110a |
| 1105b | Acceptable | Walking | 1110b |
| 1105c | 85bpm | Completed | 1110c |
| 1105d | 120bpm | 12 minutes | 1110d |
| 1105e | 80bpm | 14 | 1110e |
| 1105f | 70bpm | 115bpm | 1110f |
| 1105g | 60bpm | Yes | 1110g |
| 1105h | RR Interval, HRV, PVC burden... | 5 Minutes | 1110h |
| 1105i | RR Interval, HRV, PVC burden... | Yes | 1110i |
| 1105j | RR Interval, HRV, PVC burden... | 2 Minutes | 1110j |
| 1105k | <16 | Question Set A Responses: 1, 2, 1, 3 | 1110k |
| | | Question Set A Responses: 1, 2, 1, 3 | 1110m |

Related U.S. Application Data

(60) Provisional application No. 62/880,897, filed on Jul. 31, 2019.

(51) Int. Cl.
| | |
|---|---|
| *A61B 5/349* | (2021.01) |
| *A63B 24/00* | (2006.01) |
| *G16H 10/60* | (2018.01) |
| *G16H 15/00* | (2018.01) |
| *G16H 20/30* | (2018.01) |
| *G16H 40/67* | (2018.01) |
| *G16H 50/70* | (2018.01) |
| *A61B 5/024* | (2006.01) |
| *A61B 5/11* | (2006.01) |
| *A61B 5/339* | (2021.01) |

(52) U.S. Cl.
CPC .......... *A61B 5/4833* (2013.01); *A61B 5/7475* (2013.01); *A63B 24/0062* (2013.01); *G16H 10/60* (2018.01); *G16H 15/00* (2018.01); *G16H 40/67* (2018.01); *G16H 50/70* (2018.01); *A61B 5/02405* (2013.01); *A61B 5/02438* (2013.01); *A61B 5/112* (2013.01); *A61B 5/339* (2021.01); *A61B 2505/09* (2013.01)

(56) References Cited

U.S. PATENT DOCUMENTS

| | | | |
|---|---|---|---|
| 8,140,154 B2 * | 3/2012 | Donnelly | G16H 40/63 |
| | | | 607/6 |
| 8,374,888 B2 | 2/2013 | Earles et al. | |
| 8,818,477 B2 | 8/2014 | Soller | |
| 8,905,925 B2 | 12/2014 | Beck et al. | |
| 9,846,764 B2 | 12/2017 | Dziubinski et al. | |
| 10,055,549 B2 | 8/2018 | Chung et al. | |
| 10,262,111 B2 | 4/2019 | Dziubinski et al. | |
| 10,271,791 B2 | 4/2019 | Donnelly et al. | |
| 10,602,964 B2 | 3/2020 | Kerber | |
| 11,183,305 B2 | 11/2021 | Dziubinski et al. | |
| 11,904,202 B2 * | 2/2024 | Hacking | A61B 5/1121 |
| 2002/0156654 A1 | 10/2002 | Roe et al. | |
| 2006/0004603 A1 * | 1/2006 | Peterka | G16H 40/67 |
| | | | 705/2 |
| 2007/0219059 A1 | 9/2007 | Schwartz et al. | |
| 2012/0259652 A1 | 10/2012 | Mallon et al. | |
| 2014/0172313 A1 | 6/2014 | Rayner | |
| 2014/0172442 A1 | 6/2014 | Broderick et al. | |
| 2016/0058364 A1 * | 3/2016 | Ionescu | A61B 5/14546 |
| | | | 600/407 |
| 2016/0246937 A1 | 8/2016 | Dziubinski et al. | |
| 2017/0065823 A1 | 3/2017 | Kaib et al. | |
| 2017/0132395 A1 | 5/2017 | Futch | |
| 2017/0173262 A1 | 6/2017 | Veltz | |
| 2017/0188979 A1 | 7/2017 | Volpe | |
| 2017/0333755 A1 * | 11/2017 | Rider | A63B 21/06 |
| 2018/0049675 A1 | 2/2018 | Kerber | |
| 2018/0247713 A1 | 8/2018 | Rothman | |
| 2019/0200878 A1 | 7/2019 | Wang | |
| 2019/0282178 A1 | 9/2019 | Volosin et al. | |
| 2020/0289889 A1 * | 9/2020 | Hacking | A61B 5/0205 |
| 2021/0008413 A1 | 1/2021 | Asikainen et al. | |
| 2021/0035674 A1 | 2/2021 | Volosin et al. | |

* cited by examiner

715 ↘

Generate a Cardiac Rehabilitation Plan

716 ↘

Patient Name: | John Doe |

718 ↘
( Generate Recommended Plan )

Patient ID: | XX-XXX-XXXX |

---

Available Plan Options  ← 720

Please select one of:

- ○ Hard Cardiac Rehabilitation Plan — About Plan: Highest initial exertion levels, recommended for ACC/AHA Stage A Patients ◀— 720a
- ○ Medium Cardiac Rehabilitation Plan — About Plan: Moderate initial exertion levels, recommended for ACC/AHA Stage B Patients ◀— 720b
- ○ Easy Cardiac Rehabilitation Plan — About Plan: Lowest initial exertion levels, recommended for ACC/AHA Stage C and D Patients ◀— 720c
- ◉ Custom Cardiac Rehabilitation Plan — Note: Launches Plan Customizer Interface ◀— 720d 722 ↘ ( Submit )  ( Clear )  ( Cancel )

FIG. 7C

Cardiac Rehabilitation Plan Customization for John Doe (Patient ID XX-XXX-XXXX)

- Customize Existing Plan (726)
- ○ Hard Cardiac Rehabilitation Plan
- ○ Medium Cardiac Rehabilitation Plan
- ○ Easy Cardiac Rehabilitation Plan

Custom Plan Options (728)

728a:
- Exercise Session 1: Walking
- Frequency: Daily
- Starting Duration: 10 minutes
- Ending Duration: 30 minutes
- Target Pace: 60 Steps/min 728b:
- Exercise Session 2: Cycling
- Frequency: 3X/Wk
- Starting Duration: 15 minutes
- Ending Duration: 30 minutes
- Target Speed: 10mph 728c:
- Exercise Session 3: Weights
- Frequency: 2x/Wk
- Starting Reps: 10
- Ending Reps: 25
- Target Weight: 5 pounds

General Settings (730)

- Target HR: 100bpm
- Max HR: 120bpm
- Recommended Max. HR Levels:
  - ACC/AHA Stage A: 150bpm
  - ACC/AHA Stage B: 135bpm
  - ACC/AHA Stage C: 120bpm
  - ACC/AHA Stage D: 100bpm
- Max. Exercise Sessions Per Day: 2
- Min. Exercise Sessions Per Day: 1
- Plan Length: 30 days (732) Submit | Clear | Cancel

Cardiac Rehabilitation Plan Generation for John Doe
(Patient ID XX-XXX-XXXX)

736

Starting Information

736a

| | | | | |
|---|---|---|---|---|
| Exercise 1: | Walking ▽ | Duration: 6 minutes | Average Pace | 56 Steps/min |
| Date Completed: | 1/1/2019 | Max. Heart Rate | 115bpm | |

736b

| | | | | |
|---|---|---|---|---|
| Exercise 2: | Cylcing ▽ | Duration: 8 minutes | Average Speed | 8mph |
| Date Completed: | 1/2/2019 | Max. Heart Rate | 120bpm | |

738

Target Goal Information

738a

| | | | |
|---|---|---|---|
| Exercise 1: | Walking ▽ | Target Duration: | 25 minutes |
| Target Heart Rate: | 115bpm | Target Pace: | 70 Steps/min |

738b

| | | | |
|---|---|---|---|
| Exercise 2: | Cycling ▽ | Target Duration: | 25 minutes |
| Target Heart Rate: | 120bpm | Target Speed: | 12mph |

740

( Submit )   ( Clear )   ( Cancel )

FIG. 7E

Rehab Plan Data Structure 1000

| Plan Identifier Fields 1005 | | Individual Exercise Fields 1010 | |
|---|---|---|---|
| 1005a | Plan Identifier Field | Exercise Identifier | 1010a |
| 1005b | Overall Number of Exercises | Exercise Type | 1010b |
| 1005c | Plan Difficulty Level | Length of Exercise | 1010c |
| 1005d | Plan Recommendation Field | Post Activity RPE | 1010d |
| | | Average Heart Rate | 1010e |
| | | Pre-Exercise Questions | 1010f |
| | | Post Exercise Questions | 1010g |
| | | Warm-up | 1010h |
| | | Warm-up Type | 1010i |
| | | Warm-up Duration | 1010j |
| | | Cool Down | 1010k |
| | | Cool Down Type | 1010m |
| | | Cool Down Duration | 1010n |

FIG. 10A

Rehab Plan Data Structure 1000

| Plan Identifier Fields 1005 | Individual Exercise Fields 1010 |
|---|---|
| Plan 12 | Aerobic |
| 3 | Walking |
| Hard | 12 Minutes |
| Outcome 2 | <16 |
| | >100 |
| | Set 1 |
| | Set 1 |
| | Yes |
| | Stretching |
| | 5 minutes |
| | Yes |
| | Stretching |
| | 2 minutes |

Exercise Performance Data Structure 1100

| Overall Plan Data Fields 1105 | Individual Exercise Fields 1110 |
|---|---|
| Plan Identifier | Exercise Identifier |
| Performance Evaluation | Exercise Type |
| Overall Heart Rate | Completion Status |
| Heart Rate During Exercise | Completed Duration |
| Non-Exercise Heart Rate | Completed RPE |
| Resting Heart Rate | Completed Heart Rate |
| Sleeping Heart Rate | Warm-up Indicator |
| Overall ECG Metrics | Warm-up Duration |
| ECG Metrics During Exercise | Cool Down Indicator |
| Non-Exercise ECG Metrics | Cool Down Duration |
| Overall RPE | Pre Exercise Questions and Responses |
|  | Post Exercise Questions and Responses |

FIG. 11A

Exercise Performance Data Structure 1100

| | Overall Plan Data Fields 1105 | Individual Exercise Fields 1110 | |
|---|---|---|---|
| 1105a | Plan A | Aerobic | 1110a |
| 1105b | Acceptable | Walking | 1110b |
| 1105c | 85bpm | Completed | 1110c |
| 1105d | 120bpm | 12 minutes | 1110d |
| 1105e | 80bpm | 14 | 1110e |
| 1105f | 70bpm | 115bpm | 1110f |
| 1105g | 60bpm | Yes | 1110g |
| 1105h | RR Interval, HRV, PVC burden... | 5 Minutes | 1110h |
| 1105i | RR Interval, HRV, PVC burden... | Yes | 1110i |
| 1105j | RR Interval, HRV, PVC burden... | 2 Minutes | 1110j |
| 1105k | <16 | Question Set A Responses: 1, 2, 1, 3 | 1110k |
| | | Question Set A Responses: 1, 2, 1, 3 | 1110m |

Cardiac Rehabilitation Plan for John Doe

Next Exercise Session

- Exercise Type: Walking — 1402
- Target Duration: 10 minutes — 1404
- Target Pace: 60 Steps/min — 1406
- Scheduled Start Time: 2:00 p.m. — 1408
- Safe to Start?: Yes — 1410
- Pre-session Instructions: Stretch Secure WCD — 1412

1414 — Let's Get Started!

1416 — Cancel

Cardiac Rehabilitation Plan for John Doe

Pre-Exercise Session Questionnaire

- Do you feel well enough to exercise? Yes — 1422
- How short of breath do you feel? 2 — 1424
- How painful does your chest feel? 0 — 1426
- How tired do you feel? 1 — 1428

1430 — Submit

1432 — Cancel

Cardiac Rehabilitation Plan for John Doe

Current Exercise Session

Target Pace: [60 Steps/min] ─1406
Actual Pace: [40 Steps/min – Increase Pace] ─1442

Target Duration: [10 minutes] ─1404
Remaining Duration: [5 min. 30 sec.] ─1444

Last Milestone: [6 min. to go!] ─1446

1448─ ( End )

Cardiac Rehabilitation Plan for John Doe

Post Exercise Session Information and Questionnaire

Average Heart Rate: [100 bpm] ─1462
Average Pace: [60 Steps/min] ─1466
Rate Your Exertion During Last Session: [14 ▽] ─1470

Maximum Heart Rate: [120 bpm] ─1464
Ready to Proceed?: [No – Under-Performance of Exercise] ─1468

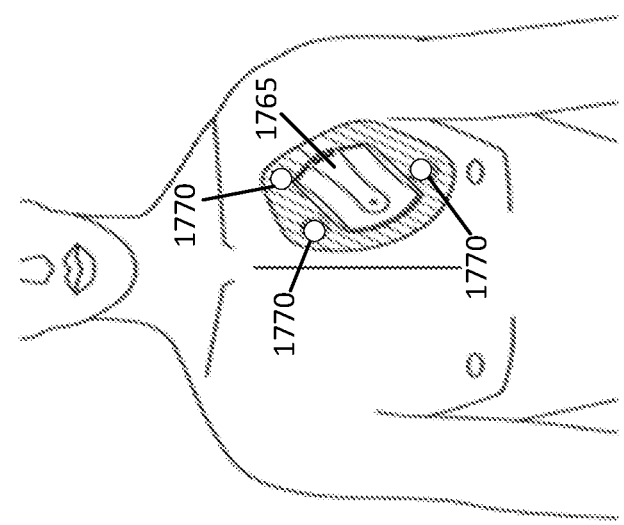
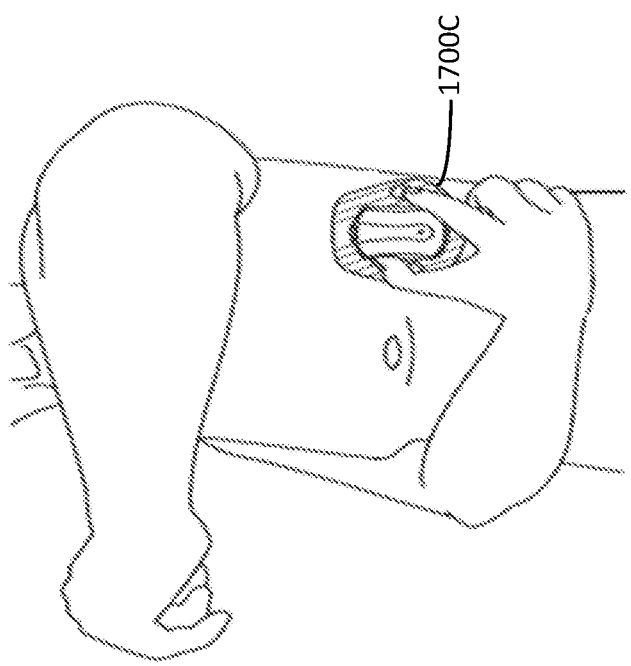
FIG. 17C

SYSTEMS AND METHODS FOR PROVIDING AND MANAGING A PERSONALIZED CARDIAC REHABILITATION PLAN

RELATED APPLICATIONS

This application claims priority under 35 U.S.C. § 120 as a continuation of U.S. application Ser. No. 16/943,099, titled "SYSTEMS AND METHODS FOR PROVIDING AND MANAGING A PERSONALIZED CARDIAC REHABILITATION PLAN," filed Jul. 30, 2020, which claims priority under 35 U.S.C. § 119(e) to U.S. Provisional Application Ser. No. 62/880,897, titled "SYSTEMS AND METHODS FOR PROVIDING AND MANAGING A PERSONALIZED CARDIAC REHABILITATION PLAN," filed Jul. 31, 2019, each of which is hereby incorporated herein by reference in its entirety.

BACKGROUND

The present disclosure is directed to determining, providing, and remotely managing personalized rehabilitation plans for ambulatory cardiac patients.

Heart failure, if left untreated, could lead to certain life-threatening arrhythmias. Both atrial and ventricular arrhythmias are common in patients with heart failure. One of the deadliest cardiac arrhythmias is ventricular fibrillation, which occurs when normal, regular electrical impulses are replaced by irregular and rapid impulses, causing the heart muscle to stop normal contractions. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity) result in the heart providing insufficient levels of blood flow to the brain and other vital organs for the support of life. It is generally useful to monitor heart failure patients to assess heart failure symptoms early and provide interventional therapies as soon as possible.

Patients who are at risk, have been hospitalized for, or otherwise are suffering from, adverse heart failure conditions can be assigned a specific treatment regimen including a physical rehabilitation plan. In some examples, depending on the underlying condition being monitored or treated, the physical rehabilitation plan can include one or more physical activities the patient is to complete daily. A professional such as a physical therapist or rehabilitation coordinator can monitor the patient's progress during the physical rehabilitation plan.

SUMMARY

In at least one example, a system for managing an individualized cardiac rehabilitation plan is provided. The system includes an externally worn device and a server. The externally worn device is configured to continuously monitor an ambulatory cardiac rehabilitation patient for one or more arrhythmias. The server is configured to operably couple to the externally worn device. The server includes a computer-readable medium, a user interface, a wireless network interface, and at least one processor operably coupled to the computer readable medium, the user interface, and the wireless network interface. The computer-readable medium includes a database stored thereon. The wireless network interface is configured to communicate securely with the externally worn device. The at least one processor is configured to receive, from the user interface, healthcare provider (HCP) input regarding the rehabilitation plan, generate one or more plan data structures based on the HCP input and to be stored in the database, the one or more plan data structures specifying an individualized set of rehabilitative exercise sessions along with associated start times and durations for each of the rehabilitative exercise sessions, the rehabilitative exercise sessions to be performed by the ambulatory cardiac rehabilitation patient over a rehabilitation period of time, cause, via the network interface, the externally worn device to administer the rehabilitation plan based on the one or more plan data structures, receive, via the network interface, electrocardiogram (ECG) and non-ECG physiological information for the ambulatory cardiac rehabilitation patient from the externally worn device, the ECG and non-ECG physiological information being periodically or continuously updated over the rehabilitation period of time, compare the ECG and/or non-ECG physiological information to predetermined criteria specified for the rehabilitation plan to generate a comparison, and dynamically adjust the cardiac rehabilitation plan based on the comparison to create an adjusted cardiac rehabilitation plan, and cause, via the network interface, the externally worn device to administer the adjusted cardiac rehabilitation plan.

Implementations of the system for managing an individualized cardiac rehabilitation plan can include one or more of the following features. In the system, the predetermined criteria can include at least one of a predetermined maximum heart rate for a rehabilitation exercise session, a resting heart rate prior to the start of a rehabilitation exercise session, a duration of the rehabilitation exercise session, a step rate for the rehabilitation exercise session, and indication of one or more arrhythmias. The at least one processor can be configured to compare the ECG and non-ECG physiological information for a first rehabilitation exercise session to the predetermined criteria, and to dynamically adjust at least one of a duration and a difficulty level of one or more of a plurality of subsequent rehabilitation exercise sessions in the plan. The at least one processor can be configured to compare the ECG and non-ECG physiological information for a first rehabilitation exercise session to the predetermined criteria, and to dynamically adjust a frequency of a plurality of subsequent rehabilitation exercise sessions in the plan. The at least one processor can be configured to perform the comparison at least based on comparing a maximum heart rate of a first rehabilitation exercise session to a predetermined maximum heart rate. The at least one processor can be configured to perform the comparison at least based on comparing a minimum heart rate of a first rehabilitation exercise session to a predetermined minimum heart rate. The at least one processor can be configured to perform the comparison at least based on comparing a step rate of a first rehabilitation exercise session to a predetermined maximum step rate. The at least one processor can be configured to perform the comparison at least based on comparing a step rate of a first rehabilitation exercise session to a predetermined step rate. The at least one processor can be configured to dynamically adjust the plan based on the comparison at least by repeating the first rehabilitation exercise session.

In the system, the at least one processor can be configured to dynamically adjust the cardiac rehabilitation plan by changing a difficulty level associated with the cardiac rehabilitation plan, a start time of at least one of the rehabilitative exercise sessions in the cardiac rehabilitation plan, and/or a duration of at least one of the rehabilitative exercise sessions in the cardiac rehabilitation plan. The at least one processor can be further configured to generate one or more exercise performance data structures based upon a performance of the cardiac rehabilitation patient during the rehabilitation period of time and store the one or more exercise performance data structures in the database. The one or more exercise performance data structures can include one or more overall plan data fields and one or more individual exercise performance data fields. The one or more overall plan data fields can include a plan identifier field, an overall percentage completed field, a performance evaluation field, an overall heart rate field, a during exercise heart rate field, a non-exercise heart rate field, a resting heart rate field, a sleeping heart rate field, one or more overall ECG metric fields, one or more ECG metrics during exercise fields, one or more ECG metrics during non-exercise fields, one or more resting ECG metrics fields, one or more sleeping ECG metrics fields, and/or one or more overall rating of perceived exertion (RPE) fields. The one or more overall ECG metrics can include heart rate metrics, RR interval metrics, heart rate variability metrics, premature ventricular complex burden or counts, atrial fibrillation burden metrics, pauses, heart rate turbulence metrics, QRS height, QRS width, changes in a size or shape of morphology of the received ECG information, cosine R-T, artificial pacing, QT interval, QT variability, T wave width, T wave alternans, T-wave variability, and/or ST segment changes. The one or more individual exercise fields can include an exercise identifier field, a type of exercise field, a completion status field, a completed duration field, a completed patient RPE field, a completed patient heart rate field, a warm-up period indicator field, a type of warm-up performed field, a length of warm-up period field, a pre-exercise questions and responses field, and a post-exercise questions and responses field.

In the system, the one or more plan data structures can include one or more overall plan data fields and one or more individual exercise performance data fields. The one or more overall plan data fields can include a plan identifier field, an overall number of exercise sessions field, a plan difficulty level field, and/or a plan recommendation field for the ambulatory cardiac rehabilitation patient. The one or more individual exercise fields can include an exercise identifier field, a type of exercise field, a prescribed length of exercise field, a prescribed RPE field, a prescribed average heart rate field, a warm-up indicated field, a type of warm-up field, a prescribed length of warm-up period field, a set of default pre-exercise questions field, and/or a set of default post-exercise questions field. The externally worn device can be configured to protect the ambulatory cardiac rehabilitation patient from the one or more arrhythmias. The one or more plan data structures can specify the individualized set of rehabilitative exercise sessions can include between about 2 rehabilitative exercise sessions and about at least one of 10, 20, 50, 100, and 500 rehabilitative exercise sessions. The rehabilitation period of time can include between about 2 days and about at least one of 1 week, 2 weeks, 4 weeks, 3 months, 6 months, one year, two years, and three years. The one or more plan data structures can specify an individualized set of rehabilitative exercise sessions can include, for each of the exercise sessions, an indication of a type of exercise. The individualized set of rehabilitative exercise sessions can include walking, biking, and/or weight training.

The one or more plan data structures can include, for each of the exercise sessions, a predetermined warm-up and/or cool-down period of time.

In the system, the externally worn device can include a plurality of ECG sensing electrodes configured to monitor a cardiac activity of the ambulatory cardiac rehabilitation patient. The externally worn device can include a plurality of therapy electrodes configured to provide an electrical therapeutic shock to the ambulatory cardiac rehabilitation patient in response to detecting one or more cardiac arrhythmias. The externally worn device can include a garment configured to be worn about a torso of the ambulatory cardiac rehabilitation patient. The externally worn device can include at least one patch configured to be adhesively attached to the ambulatory cardiac rehabilitation patient. The patch can include a plurality of ECG sensing electrodes for monitoring a cardiac activity of the ambulatory cardiac rehabilitation patient. The externally worn device can include non-ECG physiological sensors for monitoring a cardiac activity of the ambulatory cardiac rehabilitation patient. The externally worn device can include a patient user interface configured to receive patient feedback, and the at least one processor can be further configured to compare the patient feedback to the predetermined criteria specified for the rehabilitation plan to generate the comparison. The patient feedback can include an indication of the patient's perceived exertion.

In another example, a method of managing an individualized cardiac rehabilitation plan is provided. The method includes acts of receiving, by at least one processor, HCP input from a user interface operably coupled to the at least one processor, the HCP input regarding the cardiac rehabilitation plan; generating, by the at least one processor, one or more plans based on the HCP input, the one or more plans specifying an individualized set of rehabilitative exercise sessions along with associated start times and durations for each of the rehabilitative exercise sessions, the rehabilitative exercise sessions to be performed by an ambulatory cardiac rehabilitation patient over a rehabilitation period of time; storing, by the at least one processor, the one or more plans in a memory operably coupled to the at least one processor; transferring, by the at least one processor, the rehabilitation plan including the one or more plans to an externally worn device via a network interface operably coupled to the at least one processor, the externally worn device being configured to continuously monitor an ambulatory cardiac rehabilitation patient for one or more arrhythmias; causing, by the at least one processor, the externally worn device to administer the rehabilitation plan based on the one or more plans; receiving, by the at least one processor via the network interface, electrocardiogram (ECG) and non-ECG physiological information for the ambulatory cardiac rehabilitation patient from the externally worn device, the ECG and non-ECG physiological information being periodically or continuously updated over the rehabilitation period of time; dynamically adjusting, by the at least one processor, the cardiac rehabilitation plan based on the received ECG and non-ECG physiological information to create an adjusted cardiac rehabilitation plan; transferring, by the at least one processor, the adjusted cardiac rehabilitation plan to the externally worn device via the network interface; causing, by the at least one processor, the externally worn device to administer the adjusted cardiac rehabilitation plan; and confirming, by the at least one processor, that the externally worn device is administering the adjusted cardiac rehabilitation plan.

Implementations of the method for managing an individualized cardiac rehabilitation plan can include one or more of the following features. In the method, the act of dynamically adjusting the cardiac rehabilitation plan can include an act of changing, by the at least one processor, a difficulty level associated with the cardiac rehabilitation plan, a start time of at least one of the rehabilitative exercise sessions in the cardiac rehabilitation plan, and/or a duration of at least one of the rehabilitative exercise sessions in the cardiac rehabilitation plan. The method may further include acts of generating, by the at least one processor, exercise performance data based upon a performance of the cardiac rehabilitation patient during the rehabilitation period of time and storing, by the at least one processor, the exercise performance data in the memory.

In the method, the act of generating the exercise performance data can include acts of generating overall plan data and generating individual exercise performance data. The act of generating the one or more overall plan data can include an act of generating a plan identifier, an overall percentage completed, a performance evaluation, an overall heart rate, a during exercise heart rate, a non-exercise heart rate, a resting heart rate, a sleeping heart rate, an overall ECG metric, an ECG metric during exercise, an ECG metric during non-exercise, a resting ECG metric, a sleep ECG metric, and/or an overall rating of perceived exertion (RPE). The act of generating the overall ECG metrics can include an act of generating average EMAT, average RR interval, heart rate variability, premature ventricular complex burden or count, atrial fibrillation burden, pause, heart rate turbulence, QRS height, QRS width, change in a size or shape of morphology of the received ECG information, cosine R-T, artificial pacing, QT interval, QT variability, T wave width, T wave alternans, T-wave variability, and/or ST segment changes. The act of generating the individual exercise data can include an act of generating an exercise identifier, a type of exercise, a completion status, a completed duration, a completed patient RPE, a completed patient heart rate, a warm-up period indicator, a type of warm-up performed, a length of warm-up period, a pre-exercise question or response, and/or a post-exercise question or response. The act of generating the one or more plans can include acts of generating overall plan data and generating individual exercise performance data. The act of generating the overall plan data can include an act of generating a plan identifier, an overall number of exercise sessions, a plan difficulty level, and/or a plan recommendation for the ambulatory cardiac rehabilitation patient. The act of generating the individual exercise performance data can include an act of generating an exercise identifier, a type of exercise, a prescribed length of exercise, a prescribed RPE, a prescribed average heart rate, a warm-up indicated, a type of warm-up, a prescribed length of warm-up period, a set of default pre-exercise questions, and/or a set of default post-exercise questions.

The method can further include an act of protecting the ambulatory cardiac rehabilitation patient from the one or more arrhythmias via the externally worn device. In the method, the act of generating the one or more plans specifying an individualized set of rehabilitative exercise sessions can include an act of generating between about 2 rehabilitative exercise sessions and about at least one of 10, 20, 50, 100, and 500 rehabilitative exercise sessions. The act of generating the one or more plans can include an act of generating rehabilitative exercise sessions to be performed over a rehabilitation period of time between about 2 days and about at least one of 1 week, 2 weeks, 4 weeks, 3 months, 6 months, one year, two years, and three years. The act of generating the one or more plans specifying an individualized set of rehabilitative exercise sessions can include acts of generating, for each of the exercise sessions, an indication of a type of exercise. The act of generating the one or more plans can include an act of generating an individualized set of rehabilitative exercise sessions including walking, biking, and/or weight training. The act of generating the one or more plans can include an act of generating, for each of the exercise sessions, a predetermined warm-up and/or cool-down period of time.

The method can further include an act of monitoring a cardiac activity of the ambulatory cardiac rehabilitation patient via a plurality of ECG sensing electrodes of the externally worn device. The method can further include acts of detecting one or more cardiac arrhythmias and providing, in response to detection of the one or more cardiac arrhythmias, an electrical therapeutic shock to the ambulatory cardiac rehabilitation patient via a plurality of therapy electrodes of the externally worn device. The method can further include an act of wearing a garment of the externally worn device about a torso of the ambulatory cardiac rehabilitation patient. The method can further include acts of attaching, adhesively to the ambulatory cardiac rehabilitation patient, at least one patch of the externally worn device; monitoring a cardiac activity of the ambulatory cardiac rehabilitation patient via a plurality of ECG sensing electrodes of the patch; and providing, in response to detection of one or more cardiac arrhythmias, an electrical therapeutic shock to the ambulatory cardiac rehabilitation patient via a plurality of therapy electrodes of the patch. The method can further include an act of monitoring a cardiac activity of the ambulatory cardiac rehabilitation patient via a plurality of ECG sensing electrodes of the externally worn device.

In another example, a system for managing an individualized cardiac rehabilitation plan is provided. The system includes a server. The server includes a computer-readable medium, a user interface, a wireless network interface, and at least one server processor. The computer-readable medium includes a database stored thereon. The wireless network interface is configured to communicate securely with an externally worn cardiac monitoring device. The at least one server processor operably coupled to the computer-readable medium, the user interface, and the network interface. The at least one server processor configured to receive HCP input via the user interface, the HCP input regarding the rehabilitation plan, generate one or more plan data structures to be stored in the database based on the HCP input, the one or more plan data structures specifying an individualized set of rehabilitative exercise sessions, along with associated start times and durations, to be performed by an ambulatory cardiac rehabilitation patient over a rehabilitation period of time, and securely transmit the one or more plan data structures via the network interface. The externally worn cardiac monitoring device is configured to communicate with the server. The device includes at least one device processor. The at least one device processor is configured to continuously monitor the ambulatory cardiac rehabilitation patient for one or more arrhythmias, receive the one or more plan data structures from the server, instruct the ambulatory cardiac rehabilitation patient to initiate one of the rehabilitative exercise sessions of the rehabilitation plan at the associated one of the start times based on the received one or more plan data structures, cause the device to monitor heart rate and motion information of the ambulatory cardiac rehabilitation patient during performance of the one of the rehabilitative exercise sessions, compare the monitored heart rate and motion information to threshold heart rate and motion information, record one or more status identifiers based on the comparison, and securely transmit via the network interface the recorded status identifiers to the server.

Implementations of the system for managing an individualized cardiac rehabilitation plan can include one or more of the following features. In the system, the one or more status identifiers can indicate under-performance, over-performance, non-performance, non-completion, and/or completion of the one of the rehabilitative exercise sessions. The at least one server processor can be further configured to receive the recorded status identifiers; and generate a report based upon at least a portion of the recorded status identifiers. The at least one server processor can be further configured to transmit the report to a computing device associated with a physician of the ambulatory cardiac rehabilitation patient. The externally worn device can be further configured to protect the ambulatory cardiac rehabilitation patient from the one or more arrhythmias. The one or more plan data structures specifying the individualized set of rehabilitative exercise sessions can include between about 2 rehabilitative exercise sessions and about at least one of 10, 20, 50, 100, and 500 rehabilitative exercise sessions. The rehabilitation period of time can include between about 2 days and about at least one of 1 week, 2 weeks, 4 weeks, 3 months, 6 months, one year, two years, and three years. The one or more plan data structures specifying an individualized set of rehabilitative exercise sessions can include, for each of the exercise sessions, an indication of a type of exercise. The individualized set of rehabilitative exercise sessions can include walking, biking, and/or weight training. The one or more plan data structures can include, for each of the exercise sessions, a predetermined warm-up and/or cool-down period of time.

In the system, the externally worn device can further include a plurality of ECG sensing electrodes for monitoring a cardiac activity of the ambulatory cardiac rehabilitation patient. The externally worn device can include a plurality of therapy electrodes for providing an electrical therapeutic shock to the ambulatory cardiac rehabilitation patient in response to detecting one or more cardiac arrhythmias. The externally worn device can include a garment worn about a torso of the ambulatory cardiac rehabilitation patient. The externally worn device can include at least one patch adhesively attached to the ambulatory cardiac rehabilitation patient, and wherein the patch includes a plurality of ECG sensing electrodes for monitoring a cardiac activity of the ambulatory cardiac rehabilitation patient and/or a plurality of therapy electrodes for providing an electrical therapeutic shock to the ambulatory cardiac rehabilitation patient in response to detecting one or more cardiac arrhythmias. The externally worn device can include a plurality of ECG sensing electrodes for monitoring a cardiac activity of the ambulatory cardiac rehabilitation patient. The externally worn device can include non-ECG physiological sensors for monitoring a cardiac activity of the ambulatory cardiac rehabilitation patient. The non-ECG physiological sensors can include one or more of a vibrational sensor, a pulse oxygen sensor, a blood pressure sensor, a lung fluid sensor, and a motion sensor.

In another example, a method of managing an individualized cardiac rehabilitation plan is provided. The method includes acts of receiving, by at least one server processor, HCP input regarding the rehabilitation plan via a user interface operably coupled to the at least one server processor; generating, by the at least one server processor, one or more plans based on the HCP input and specifying an individualized set of rehabilitative exercise sessions, along with associated start times and durations, to be performed by an ambulatory cardiac rehabilitation patient over a rehabilitation period of time; securely transmitting, by the at least one server processor, the one or more plans via a network interface; continuously monitoring, by at least one device processor, the ambulatory cardiac rehabilitation patient for one or more arrhythmias; receiving, by the at least one device processor, the one or more plans from the at least one server processor; instructing, by the at least one device processor, the ambulatory cardiac rehabilitation patient to initiate one of the rehabilitative exercise sessions of the rehabilitation plan at the associated one of the start times based on the received one or more plans; causing, by the at least one device processor, monitoring of heart rate and motion information of the ambulatory cardiac rehabilitation patient during performance of the one of the rehabilitative exercise sessions; comparing, by the at least one device processor, the monitored heart rate and motion information to threshold heart rate and motion information; recording, by the at least one device processor, one or more status identifiers based on the comparison; and securely transmitting, by the at least one device processor, the recorded status identifiers to the at least one server processor via the network interface.

Implementations of the method for managing an individualized cardiac rehabilitation plan can include one or more of the following features. In the method, the one or more status identifiers can indicate under-performance, over-performance, non-performance, non-completion, and/or completion of the one of the rehabilitative exercise sessions. The method can further include acts of receiving, by the at least one server processor, the recorded status identifiers and generating, by the at least one server processor, a report based upon at least a portion of the recorded status identifiers. The method can further include an act of transmitting, by the at least one server processor, the report to a computing device associated with a physician of the ambulatory cardiac rehabilitation patient. The method can further include an act of protecting the ambulatory cardiac rehabilitation patient from the one or more arrhythmias via an externally worn device including the at least one device processor.

In the method, the act of generating the one or more plans specifying an individualized set of rehabilitative exercise sessions can include an act of generating between about 2 rehabilitative exercise sessions and about at least one of 10, 20, 50, 100, and 500 rehabilitative exercise sessions. The act of generating the one or more plans can include an act of generating rehabilitative exercise sessions to be performed over a rehabilitation period of time between about 2 days and about at least one of 1 week, 2 weeks, 4 weeks, 3 months, 6 months, one year, two years, and three years. The act of generating the one or more plans specifying an individualized set of rehabilitative exercise sessions can include an act of generating, for each of the exercise sessions, an indication of a type of exercise. The act of generating the one or more plans can include an act of generating an individualized set of rehabilitative exercise sessions including walking, biking, and/or weight training. The act of generating the one or more plans can include acts of generating, for each of the exercise sessions, a predetermined warm-up and/or cool-down period of time.

The method can further include an act of monitoring a cardiac activity of the ambulatory cardiac rehabilitation patient via a plurality of ECG sensing electrodes of an externally worn device including the at least one device processor. The method can further include acts of detecting one or more cardiac arrhythmias and providing, in response to detection of the one or more cardiac arrhythmias, an electrical therapeutic shock to the ambulatory cardiac rehabilitation patient via a plurality of therapy electrodes of an externally worn device including the at least one device processor. The method can further include an act of wearing a garment of a device externally worn about a torso of the ambulatory cardiac rehabilitation patient, the device including the at least one device processor. The method can further include acts of attaching, adhesively to the ambulatory cardiac rehabilitation patient, at least one patch of an externally worn device including the at least one device processor; monitoring a cardiac activity of the ambulatory cardiac rehabilitation patient via a plurality of ECG sensing electrodes of the patch; and providing, in response to detection of one or more cardiac arrhythmias, an electrical therapeutic shock to the ambulatory cardiac rehabilitation patient via a plurality of therapy electrodes of the patch. The method can further include an act of monitoring a cardiac activity of the ambulatory cardiac rehabilitation patient via a plurality of ECG sensing electrodes of an externally worn device including the at least one device processor.

In an additional example, a system for generating a patient-specific cardiac rehabilitation plan can be provided. The system can include an HCP computing device associated with an HCP of a cardiac rehabilitation patient and a server computing device operably coupled to the HCP computing device. The HCP computing device can include a memory storing patient baseline information for the cardiac rehabilitation patient and at least one first processor coupled to the memory and configured to receive rehabilitation goal information from the HCP and present a patient-specific cardiac rehabilitation plan to the HCP based on the rehabilitation goal information.

The server computer can include a first network interface configured to receive the rehabilitation goal information from the HCP computing device and a second network interface configured to remotely communicate with at least a wearable cardiac monitoring device being worn by the cardiac rehabilitation patient, the wearable cardiac monitoring device including a plurality of electrocardiogram (ECG) electrodes configured to continuously sense an ECG signal for the cardiac rehabilitation patient and a motion sensor configured to monitor a movement of the cardiac rehabilitation patient and produce a motion signal. The second network interface can be further configured to receive patient baseline information from the wearable cardiac monitoring device. The server computing device can further include a memory configured to store at least the rehabilitation goal information, the patient baseline information, and historic patient data for the cardiac rehabilitation patient, and at least one processor operably coupled to the first network interface, the second network interface, and the memory, the at least one processor being configured to determine a patient start point based upon the patient baseline information, determine a patient end point based upon the rehabilitation goal information, determine a rehabilitation time period based upon the rehabilitation goal information, generate the patient-specific cardiac rehabilitation plan based upon the patient start point, the patient end point, the rehabilitation time period, and the historic patient data for the cardiac rehabilitation patient, and transmit the patient-specific cardiac rehabilitation plan to the HCP computing device for presentation to the HCP and implementation on the wearable cardiac monitoring device.

In some examples of the above-described system, the baseline information can include patient result information corresponding to the cardiac rehabilitation patient completing an initial physical activity. In some examples, the initial physical activity can include a six-minute walk test.

In some examples of the above-described system, the rehabilitation goal information can include at least one final physical activity the cardiac rehabilitation patient is to complete after the rehabilitation period.

In some examples of the above-described system, the rehabilitation period can include at least one of two weeks, thirty days, one month, forty-five days, two months, three months, and ninety days. In some examples, the rehabilitation period can include between about 2 days and about at least one of 1 week, 2 weeks, 4 weeks, 3 months, 6 months, one year, two years, and three years.

In some examples of the above-described system, the patient-specific cardiac rehabilitation plan can include a series of physical activities to be performed by the cardiac rehabilitation patient over the rehabilitation period. In some examples, each of the series of physical activities lasts a predetermined period of time, the physical activities including at least one of walking, biking, and weight training.

In some examples of the above-described system, the at least one processor can be further configured to transmit the patient-specific cardiac rehabilitation plan to the wearable cardiac monitoring device. In some examples, the wearable cardiac monitoring device is configured to monitor the cardiac rehabilitation patient during completion of physical activities included in the patient-specific cardiac rehabilitation plan.

An additional example can include a computing device operably coupled to a wearable cardiac monitoring device. The computing device can include a network interface configured to receive, from the wearable cardiac monitoring device, patient data generated from an ECG signal and a motion signal acquired by the wearable cardiac monitoring device; a memory configured to store medical history data for the cardiac rehabilitation patient and a cardiac rehabilitation plan over a rehabilitation period; and at least one processor operably coupled to the memory and the network interface. The at least one processor can be configured to retrieve the medical history data from the memory, determine the cardiac rehabilitation plan based on at least the medical history data for the cardiac rehabilitation patient, the cardiac rehabilitation plan including a plurality of activities, each of the plurality of activities having an associated activity duration, store the cardiac rehabilitation plan on the memory, determine a start time for an exercise session based upon the cardiac rehabilitation plan, at the start time of the exercise session, initiate recording of exercise performance data generated from the ECG signal for the cardiac rehabilitation patient and the motion signal as acquired by the wearable cardiac monitoring device during the exercise session, complete the recording of exercise performance data upon determining that the exercise session has ended, store the recorded exercise performance data on the memory, analyze the recorded exercise performance data to determine a condition of the patient during the exercise session of the cardiac rehabilitation plan and adherence information indicating patient adherence to the cardiac rehabilitation plan, determine whether changes to the cardiac rehabilitation plan are recommended based upon the condition of the patient during the exercise session and the adherence information, and, where changes are recommended, generate an updated cardiac rehabilitation plan, store the updated cardiac rehabilitation plan on the memory, and cause the wearable cardiac monitoring device to execute the updated cardiac rehabilitation plan.

In some examples of the above-described computing device, the wearable cardiac monitoring device can include a plurality of ECG electrodes configured to continuously sense the ECG signal for the cardiac rehabilitation patient and a motion sensor configured to monitor a movement of the cardiac rehabilitation patient and produce the motion signal.

In some examples of the above-described computing device, the wearable cardiac monitoring device can further include at least one non-ECG physiological sensor configured to monitor at least one physiological signal other than the ECG signal of the cardiac rehabilitation patient. In some examples, the at least one physiological sensor can include a cardio-vibrational sensor configured to measure heart sounds information for the cardiac rehabilitation patient. In some examples, the at least one non-ECG physiological sensor can include at least one of a pulse oxygen sensor, a blood pressure sensor, and a lung fluid sensor.

In some examples of the above-described computing device, the motion sensor comprising at least one of an accelerometer and a gyroscope. In some examples, the motion signal can include at least one of position information, movement information, and orientation information.

In some examples of the above-described computing device, the cardiac rehabilitation plan can include a series of physical activities to be performed by the cardiac rehabilitation patient over the rehabilitation period, each physical activity being associated with one or more exercise sessions. In some examples, each of the series of physical activities lasts a predetermined period of time, the physical activities comprising at least one of walking, biking, and weight training. In some examples, at least one of the series of physical activities can include a warm-up period and a cool down period. In some examples, the rehabilitation period can include at least one of two weeks, thirty days, one month, forty-five days, two months, three months, and ninety days. In some examples, the at least one processor can be configured to initiate the exercise session of the cardiac rehabilitation plan by indicating to the cardiac rehabilitation patient that the cardiac rehabilitation patient is to complete at least one of the series of physical activities. In some examples, the computer device can include a display operably coupled to the at least one processor and configured to display the indication to the cardiac rehabilitation patient that the cardiac rehabilitation patient is to complete at least one of the series of physical activities.

In some examples of the above-described computing device, the patient analysis information is based on analyzing one or more ECG metrics derived from the ECG signal for the cardiac rehabilitation patient collected by the wearable cardiac monitoring device during the exercise session. In some examples, the at least one processor can be further configured to monitor the one or more ECG metrics during the exercise session to determine if any of the one or more ECG metrics exceed at least one metric threshold. In some examples, the at least one metric threshold can include at least one of an average heart rate over 120 beats per minute and an average heart rate greater than thirty beats per minute above an average resting heart rate for the cardiac rehabilitation patient.

In some examples of the above-described computing device, the memory can be further configured to store activity baseline information for the cardiac rehabilitation patient. In some examples, the cardiac rehabilitation plan includes an associated difficulty rating determined from the baseline information for the cardiac rehabilitation patient. In some examples, the least one processor can be further configured to generate the updated cardiac rehabilitation plan by altering the associated difficulty rating of the cardiac rehabilitation plan.

In some examples of the above-described computing device, the patient data can further include patient exertion feedback comprising at least one of a rating of perceived exertion from the cardiac rehabilitation patient, shortness of breath information, and fatigue level information. In some examples, the at least one processor can be configured to alter the exercise session of the cardiac rehabilitation plan during completion by the cardiac rehabilitation patient based upon the patient exertion feedback.

In some examples of the above-described computing device, the at least one processor can be further configured to receive physician approval of the updated cardiac rehabilitation plan prior to implementation.

In some examples of the above-described computing device, the at least one processor can be further configured to generate one or more reports based upon the patient information as the cardiac rehabilitation patient completes the cardiac rehabilitation plan.

In some examples of the above-described computing device, the at least one processor can be further configured to receive, from the wearable cardiac monitoring device, intersession patient data acquired by the wearable cardiac monitoring device corresponding to periods of time between exercise sessions of the cardiac rehabilitation plan; analyze the intersession patient data to identify at least one physiological event; and determine whether changes are recommended for the cardiac rehabilitation plan based upon the identified physiologic events. In some example, the at least one physiological event can include at least one of an atrial fibrillation event, a bradycardia event, a tachycardia event such as tachycardia onset and tachycardia offset, a pause in heart rate, high average heart rate, a transitory heart rate spike, and a transitory heart rate dip. In some examples, the at least one physiological event can include at least one of a high average blood pressure, a low average blood pressure, a transitory blood pressure spike, a transitory blood pressure dip, and low average blood oxygen levels.

In some examples of the above-described computing device, the at least one processor can be further configured to receive, from the wearable cardiac monitoring device, pre-session patient data acquired by the wearable cardiac monitoring device during a pre-activity period prior to an exercise session of the cardiac rehabilitation plan; analyze the pre-session patient data to identify one or more physiologic events; and determine whether changes are recommended for the cardiac rehabilitation plan based upon any identified potential cardiac events in the pre-session patient data. In some examples, the pre-session patient data can include answers to a pre-session questionnaire provided by the cardiac rehabilitation patient. In some examples, the pre-activity period can include at least one of a half hour before the exercise session, an hour before the exercise session, two hours before the exercise session, and four hours before the exercise session.

In some examples, one or more computer readable, non-transitory storage media are provided. The one or more media store instructions that are executable by a processor to perform the method actions described herein.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples and are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIG. 7C depicts a view of a sample user interface that a physician can access to generate a cardiac rehabilitation plan for a cardiac patient, in accordance with an example of the present disclosure.

FIG. 7D depicts a view of a sample user interface that a physician can access to customize an individualized cardiac rehabilitation plan for a cardiac patient, in accordance with an example of the present disclosure.

FIG. 7E depicts a view of a sample user interface that a physician can access to generate a cardiac rehabilitation plan for a cardiac patient based upon starting and target goal information, in accordance with an example of the present disclosure.

FIGS. 10A and 10B depict sample rehabilitation plan data structures to use in generating a cardiac rehabilitation plan, in accordance with an example of the present disclosure.

FIGS. 11A and 11B depict sample exercise performance data structures to use when monitoring a patient's progression through a cardiac rehabilitation plan, in accordance with an example of the present disclosure.

FIG. 14A depicts a view of a sample user interface configured to provide access to information regarding a future exercise session.

FIG. 14B depicts a view of a sample user interface configured to provide a pre-exercise session questionnaire.

FIG. 14C depicts a view of a sample user interface configured to provide access to information regarding a current exercise session.

FIG. 14D depicts a view of a sample user interface configured to provide access to information regarding a previous exercise session.

FIGS. 17A-17D depict sample ambulatory medical devices that may be prescribed to a heart failure patient, in accordance with an example of the present disclosure.

DETAILED DESCRIPTION

Figure 1:
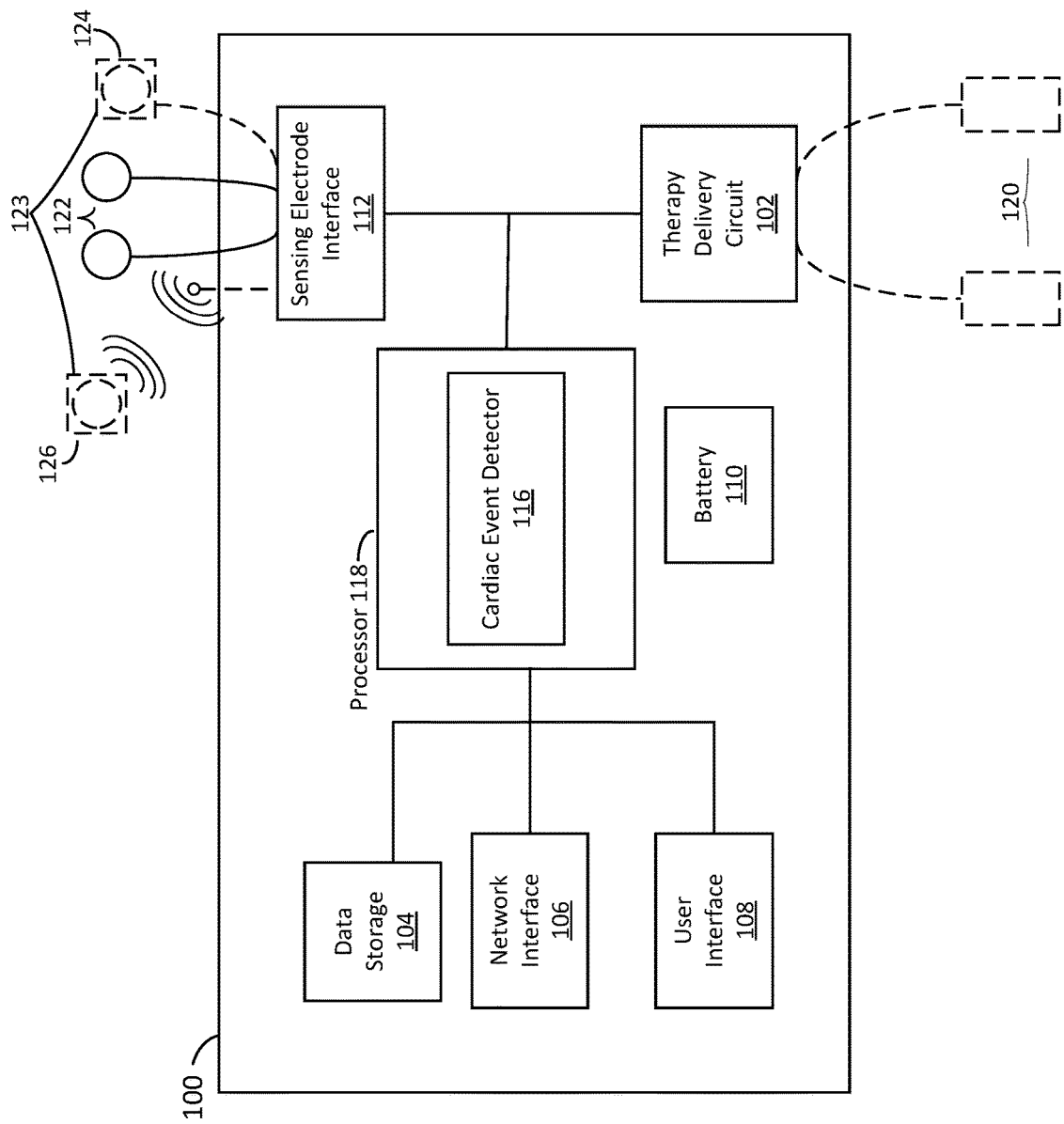
FIG. 1 depicts a schematic view of a sample controller for a wearable medical device, in accordance with an example of the present disclosure.

Wearable medical devices, such as cardiac event monitoring devices, are used in clinical or outpatient settings to monitor and/or record various ECG and other physiological signals for a patient. These ECG and other physiological signals can be used to determine a current condition for a patient as well as to predict, plan, and prepare for future adverse events such as cardiac events or other adverse changes to a patient's health.

Additionally, for many heart failure patients, a physical rehabilitation plan, or cardiac rehabilitation plan, is prescribed to improve the physical condition of the patient. Individuals with cardiac disease or who have experienced a cardiac event typically benefit from participation in a cardiac rehabilitation plan that includes regular exercise and lifestyle changes. Cardiac rehabilitation is commonly used to deliver exercise and lifestyle interventions. Cardiac rehabilitation can include coordinated, multifaceted interventions designed to reduce risk, foster and sustain performance of healthy behaviors, reduce disability, and promote an active lifestyle for heart failure patients.

Wearable medical devices are continuously worn and so can continuously monitor ECG and other physiological information of ambulatory patients. Systems, devices, and techniques herein implement cardiac rehabilitation plans that draw on such continuously available real-time ECG and non-ECG physiological information in at least two ways. First, the device is configured to provide individualized plans that are dynamically adjusted based on the most current and/or real time ECG and non-ECG physiological information from the ambulatory patient. Second, the device is configured to measure the patient's adherence to such plans based on the most current and/or real time ECG and non-ECG physiological information from the ambulatory patient. In these implementations, rather than relying only on patient responses and patient self-reporting of progress or adherence, the device is configured to use the most current and/or real time ECG and non-ECG physiological information from the ambulatory patient to determine how to automatically adjust the plan and/or record accurately whether the patient is performing the activities in the plan. For example, the non-ECG physiological information can include patient motion information (such as step rate, patient position, and posture), respiration information, lung fluid level information, pulse information, blood oxygenation information (e.g., VO2 metrics, VCO2 metrics, etc.), blood pressure information, and other such information. In some implementations, the device is configured to process patient feedback received via a user interface (e.g., responses to questions, pre- and post-workout questions and surveys, indications of exertion, such as a rating of perceived exertion or RPE) when dynamically adjusting a plan or tracking patient adherence to the plan.

Cardiac rehabilitation as described herein can be delivered in both in-patient and outpatient settings and has been shown to reduce the rate of mortality and morbidity in heart failure patients by stabilizing, slowing, or even reversing the progression of certain cardiac diseases. Clinical data demonstrates that engaging in a properly administered outpatient cardiac rehabilitation is safe and reduces morbidity, mortality, and readmission rates. Various studies have shown that patients who participate in outpatient cardiac rehabilitation have a lower risk of death (e.g., 21%-47%), a lower risk of myocardial infarction (e.g., 21%-31%), and decreased readmissions as compared to patients who do not participate in outpatient cardiac rehabilitation. The benefits provided by cardiac rehabilitation features, systems, devices, and techniques as described herein are important to the individual heart failure patient and to society as subsequent healthcare costs may be reduced following participation, with greater cost-effectiveness in patients at high risk for subsequent cardiac events.

Unfortunately, approximately 45%-60% of patients are never referred to an outpatient cardiac rehabilitation program and an additional approximately 25% that are referred do not enroll in the program. Moreover, patient adherence to cardiac rehabilitation plans is problematic, with average dropout rates running as high as 50%. There are several reasons given for these discouraging statistics, but a predominant reason listed amongst cardiac patients that do not enroll in an outpatient cardiac is the requirement to attend scheduled rehabilitative exercise sessions at a specific facility or office. A patient may be required to attend a number of office visits throughout the rehabilitation period, usually multiple visits a week. For some patients with limited mobility or transportation resources, such a commitment becomes burdensome and the cardiac rehabilitation plan is partially or completely ignored, and the patient's physical recovery directly suffers. An aspect of the cardiac rehabilitation process is modification of the rehabilitation plan in response to how the patient is progressing through the rehabilitation plan. Without regular office visits for close evaluation during physical activities, adjustment of the cardiac rehabilitation plan is nearly impossible. Thus, many of the benefits of cardiac rehabilitation described above remain unrealized for many patients.

To address these and other obstacles to successful execution of, and patient adherence to, cardiac rehabilitation plans, methods and systems are described herein to facilitate remote physical exercise sessions that are individualized to each patient and dynamically adjusted, both at the outset of the cardiac rehabilitation plan and as the patient progresses through the plan. These features increase the convenience of the exercise sessions and decrease the discomfort felt by the patient by aligning exercise frequency, intensity, and duration with the patient's current medical condition. Thus, the methods and systems described herein provide a patient and their healthcare provider (HCP) with the ability to engage in remote physical exercise sessions as outlined in a cardiac rehabilitation plan while still providing the benefits of adjusting the cardiac rehabilitation plan based upon patient response to the physical activities and exercise sessions included in the plan.

In certain implementations of the present disclosure, methods and systems use the monitoring and processing capabilities of ambulatory medical devices to monitor patient physiological information during performance of a cardiac rehabilitation exercise session. The physiological information monitored during an exercise session can include ECG information as well as non-ECG physiological information such as motion information. In some implementations, the ambulatory medical device can also track how the patient's body responds to the exercise session—before, during, and after its occurrence. To monitor and protect the patient from life-threatening arrhythmias during exercise sessions, the ambulatory medical device can include arrhythmia treatment elements, for example, as in the case of a wearable cardioverter/defibrillator (WCD) or an externally worn transcutaneous pacing device.

In certain implementations, the various ECG and non-ECG physiological information collected by the medical device can be used to determine when the patient starts an exercise session (start time), how long the patient performs the exercise session (duration), and when the patient ends the exercise session (end time). For specific exercises such as walking, the ECG and non-ECG physiological information can be used to determine additional activity-specific information such as how far the patient travels during the exercise session, what their average step rate is during the exercise session, what their maximum step rate is during the exercise session, whether the patient rests during the exercise session, and other similar information. The physiological information can also be used to determine additional physical response data for the patient such as maximum heart rate during the exercise session, average heart rate during the exercise session, average respiratory rate during the exercise session, maximum respiratory rate during the exercise session, ventricular tachycardia (VT)/ventricular fibrillation (VF) onset occurrence, and other similar physiological metrics.

In some implementations, the methods and systems further utilize the processing capabilities of a remote server and/or the medical device to generate and adjust cardiac rehabilitation plans. This server can include a network interface in secure wireless communication with the wearable medical device and at least one processor configured to execute a variety of processes. For instance, in these implementations, the processor has access to a database housing one or more plan data structures. The processor can execute a plan generation process that parses input received from an HCP and generates one or more rehabilitation plans. The plan generation process can store the generated rehabilitation plans in the plan data structures within the database. Some examples of plan data structures and the information housed therein are described further below, but in at least one example, the one or more plan data structures specify an individualized set of rehabilitative exercises to be performed by the patient over a rehabilitation period. As each of the exercises can be associated with start times, and durations and/or end times, in some examples, the plan data structures include fields configured to store values that represent these chronological elements.

In some implementations, the server can cause the patient's wearable medical device to administer a rehabilitation plan based on the one or more plan data structures. For instance, the server can transmit a message via a network connecting the server and the wearable medical device. The message can include data descriptive of a rehabilitation plan and a request for the wearable medical device to begin administration of the rehabilitation plan. In response to receipt of the message, the wearable medical device can notify, via a user interface, the patient of details regarding the rehabilitation plan, provide reminders to perform exercise sessions, and execute other processes that administer the rehabilitation plan. As described above, the wearable medical device can further track the patient's performance during exercise sessions. In addition, the wearable medical device can transmit messages to the server that communicate the patient's ECG and non-ECG physiological information and additional physical response data.

In certain implementations, the server can receive and process the collected and determined information from the patient's wearable medical device. For example, the server can periodically or continuously parse the messages containing the physiological information and determine whether the cardiac rehabilitation plan should be adjusted for the patient. Where adjustments are needed, the server can automatically generate one or more updated cardiac rehabilitation plans over the course of the patient's rehabilitation efforts. These updates can include dynamic adjustments to the rehabilitation plan based on the received ECG and non-ECG physiological information, the additional physical response data, and the patient's progression through the rehabilitation plan. In addition, the server can cause the patient's wearable medical device to execute the adjusted rehabilitation plan using the processes described generally above and described in more detail below.

In some examples, the system (e.g., the server and/or the wearable medical device) can implement a user interface through which the system can receive input from the HCP regarding the initial rehabilitation plan and/or updated rehabilitation plans. This user interface can include controls that display and/or receive input regarding elements of a rehabilitation plan. In this way, these example systems enable an HCP to approve and/or modify the initial rehabilitation plan and/or dynamic adjustments specified in one or more updated rehabilitation plans.

In addition to dynamically adjusting a cardiac rehabilitation plan, example systems and methods of the present disclosure can further monitor patient performance of, and adherence to, the cardiac rehabilitation plan. An advantage of the disclosures herein is that the patient need not attend HCP clinical office visits. Rather, the wearable medical device automatically monitors the patient's progress through the plan. As the patient is not regularly attending office visits, the patient's HCP will not need to receive regular updates from a supervising professional. As described herein, the data collected by the patient's wearable medical device can be used to determine the patient's performance throughout the rehabilitation plan and to determine whether the patient is on track for completing or substantially completing the prescribed cardiac rehabilitation plan. In some examples, information regarding patient performance and adherence to the rehabilitation plan can be reviewed, for example, via a user interface provided by the server. In some examples, this user interface takes the form of one or more web pages served by the server to a device associated with the HCP accessible, for example, via a physician's portal or other similar information interface.

The methods and systems described herein provide several advantages. For instance, the examples disclosed herein enable a wide population of ambulatory cardiac rehabilitation patients to participate, following a physician's or other HCP's referral, in cardiac rehabilitation plans that focus on preventative and rehabilitative services. This population of patients can include hospitalized patients, patients recently discharged from hospital following a cardiac event or procedure, and/or out-patients who have recently been diagnosed with being at risk of a cardiac event. In some implementations, the methods and systems described herein administer plans that focus on assessment of current clinical condition, patient mobilization, and identification and provision of information regarding modifiable risk factors and self-care. Further, some example methods and systems include a focus on discharge planning with a daily living plan and planning for outpatient cardiac rehabilitation. For instance, during the patient cardiac rehabilitation as described herein, a patient can be closely monitored, with the help of specialized wearable medical devices, and assessed by one or more HCPs for adverse conditions. In some examples, an HCP can use the devices and processes disclosed herein to perform a baseline assessment of the patient prior to patient performance of any given exercise session included in a cardiac rehabilitation plan and determine whether the patient should perform or skip/postpose the exercise session.

Table 1 as shown below includes a set of parameters monitored and analyzed by wearable medical devices in some examples when determining whether to skip/postpone or stop an exercise session. The options presented below can be presented to a patient (e.g., via the user interface of the wearable medical device) and/or an HCP (e.g., via a user interface implemented via the remote server) to indicate whether a session in the plan is to be skipped or stopped, and provide a reason for skipping or stopping the session.

TABLE 1

| Evaluated Parameters to Skip Exercise Session (Patient and/or HCP indicates information below by selecting a corresponding user interface option indicating why the patient wishes to skip exercise session) | Evaluated Parameters to Stop Exercise Session (Patient and/or HCP indicates information below by selecting a corresponding user interface option indicating why the patient wishes to stop exercise session) |
|---|---|
| New or recurrent chest pain in previous period of time (e.g., 8 hours) | Diastolic blood pressure over 110 mmHg |
| increasing creatine kinase and/or troponin values | Decrease in systolic blood pressure over 10 mmHg during exercise session |
| Indication of decompensated heart failure | Significant ventricular or atrial arrhythmias with or without associated symptoms |
| Abnormal cardiac rhythm or unstable ECG over previous period of time (e.g., 8 hours) | Second-degree or third-degree heart block |
| | Signs of exercise intolerance including angina, marked dyspnea, and ECG changes indicative of ischemia |

In some examples, a wearable medical device is configured to provide an HCP, or a physical therapist working under instruction of an HCP, supervising a cardiac rehabilitation plan with access to and documentation of vital signs and bio-acoustic data. This data can provide feedback on the patient's musculoskeletal strength and flexibility. If the patient is still in the hospital, the cardiac rehabilitation plan administered via the wearable medical devices described herein can include self-care activities, walking, upper body movement or weight training, controlled stair climbing, and other similar activities in preparation for the patient's discharge. Table 2 below includes recommendations for both aerobic and flexibility exercises for a patient cardiac rehabilitation plan, where the patient may still be in the hospital. The exercises in Table 2 below may be part of a recommended cardiac rehabilitation plan administered via a wearable medical device and remotely monitored at a server.

TABLE 2

|  | Aerobic Exercises | Flexibility Exercises |
|---|---|---|
| Frequency | 2-4 times per day | Minimally once per day or as often as tolerated |
| Intensity | Until heart rate is 20 bpm above resting heart rate for myocardial infarction patients<br>Until heart rate is 30 bpm above resting heart rate for patients recovering from heart surgery | Until mild stretch discomfort |
| Time | Begin with 3-5 minutes of walking as tolerated, progressively adding duration. A rest period may include a slower walking pace or a complete rest that is shorter than the duration of the exercise, attempting to achieve a 2:1 exercise/rest ratio. Progressing to 10-15 minutes of continuous walking. | 30 seconds for each major joint |
| Type | Walking or other aerobic modes (e.g., cycling) | Focus on dynamic movement with interest to lower back and posterior thigh regions. |

Prior to discharge from a hospital, a patient can have a safe and progressive outpatient cardiac rehabilitation plan formulated. In examples where a patient is referred to an outpatient cardiac rehabilitation plan, the patient can transition into an outpatient cardiac rehabilitation program administered by a wearable medical device as described in detail below. Goals recorded and tracked by the wearable medical device for outpatient cardiac rehabilitation generally include goals similar to those recorded and tracked for inpatient cardiac rehabilitation. These goals can include, for example, to develop and assist the patient with implementing a safe and effective formal exercise and lifestyle physical activity program, to provide appropriate supervision and monitoring to detect changes in clinical status, to provide ongoing surveillance to the patient's HCPs in order to enhance medical management, to return the patient to vocational and recreational activities or modify these activities based upon the patient's clinical status, and to provide patient education to optimize secondary prevention. Table 3 below includes recommendations for aerobic, resistance, and flexibility exercise sessions to be performed during performance of an outpatient cardiac rehabilitation plan. As such, the exercises in Table 3 below may be part of a recommended cardiac rehabilitation plan administered via a wearable medical device and remotely monitored at a server.

TABLE 3

|  | Aerobic Exercise | Resistance Exercise | Flexibility Exercise |
|---|---|---|---|
| Frequency | Minimally 3 days a week | 2-3 nonconsecutive days a week | 2-3 times per week |
| Intensity | Until heart rate is 30 bpm above resting heart rate or Rating of Perceived Exertion (RPE) is 12-16 (on a 6-20 scale) | Until 10-15 repetitions without significant fatigue, RPE is 11-13 (on a 6-20 scale) | To the point of feeling tightness or slight discomfort |
| Time | 20-60 minutes | 1-3 sets, 8-10 different exercises focusing on major muscle groups | 15 second holds for static stretching, 4 or more repetitions of each stretch |
| Type | Walking, cycling, stepping, rowing, elliptical exercise, ergometer exercise, stair climbing | Select equipment that is safe and comfortable for the patient | Static and dynamic stretching focused on the major limb joints and the lower back |

To efficiently manage outpatient cardiac rehabilitation over a rehabilitation period, example processes and devices disclosed herein monitor and evaluate various patient parameters as the patient progresses through the rehabilitation period. In some examples, a wearable medical device is configured to routinely assess various parameters before, during, and after each rehabilitation session, as deemed appropriate by an HCP. These parameters can include heart rate assessment, blood pressure assessment, changes in patient weight, symptoms of exercise intolerance, symptoms of evidence of change in clinical status, changes in medication adherence, ECG monitoring, non-ECG physiological signal monitoring, and patient feedback. Parameters similar to those as shown in Table 1 can be evaluated by a supervising professional prior to or during an exercise session to determine if the patient should skip/postpone an exercise session or stop an ongoing exercise session. Additionally, it should be noted that the parameters assessed, as described above, can be adjusted for an individual patient as the patient progresses through the rehabilitation period.

These examples, and various other similar examples of benefits and advantages of the techniques, processes, and approaches as provided herein, are described in additional detail below.

The various dynamic adjustment and adherence monitoring processes described herein are implemented, in some examples, by data processing devices, such as computer systems and certain types of medical devices. For instance, some examples include a patient monitoring and treatment device. Patient monitoring and treatment devices are used to monitor and record various physiological or vital signals for a patient and provide treatment to a patient when necessary. For patients at risk of a cardiac arrhythmia, specialized cardiac monitoring and/or treatment devices such as a cardiac event monitoring device, a WCD, or a hospital wearable defibrillator can be prescribed to and worn by the patient for an extended period of time. For example, a patient having an elevated risk of sudden cardiac death, unexplained syncope, prior symptoms of heart failure, an ejection fraction of less than 45%, less than 35%, or other such threshold deemed of concern by a physician, and other similar patients in a state of degraded cardiac health can be prescribed a specialized cardiac monitoring and/or treatment device.

For example, a WCD such as the LifeVest® Wearable Cardioverter Defibrillator from ZOLL Medical Corporation (Chelmsford, MA), can be prescribed to the patient. As described in further detail below, such a device includes a garment that is configured to be worn about the torso of the patient. The garment can be configured to house various components such as ECG sensing electrodes and therapy electrodes. The components in the garment can be operably connected to a monitoring device that is configured to receive and process signals from the ECG sensing electrodes to determine a current cardiac condition of the patient and, if necessary, provide treatment to the patient using the therapy electrodes.

FIG. 1 illustrates an example component-level view of the medical device controller 100 included in, for example, a wearable medical device such as a WCD. As shown in FIG. 1, the medical device controller 100 can include a therapy delivery circuitry 102, a data storage 104, a network interface 106, a user interface 108, at least one battery 110, a sensor interface 112 (e.g., to interface with both ECG sensing electrodes 122 and non-ECG physiological sensors 123 such as motion sensors, vibrational sensors, lung fluid sensors, infrared and near-infrared-based pulse oxygen sensor, blood pressure sensors, among others), a cardiac event detector 116, and least one processor 118. In some examples, the patient monitoring medical device can include a medical device controller 100 that includes like components as those described above but does not include the therapy delivery circuitry 102 (shown in dotted lines). FIG. 1 is described in greater detail below.

Figure 2:
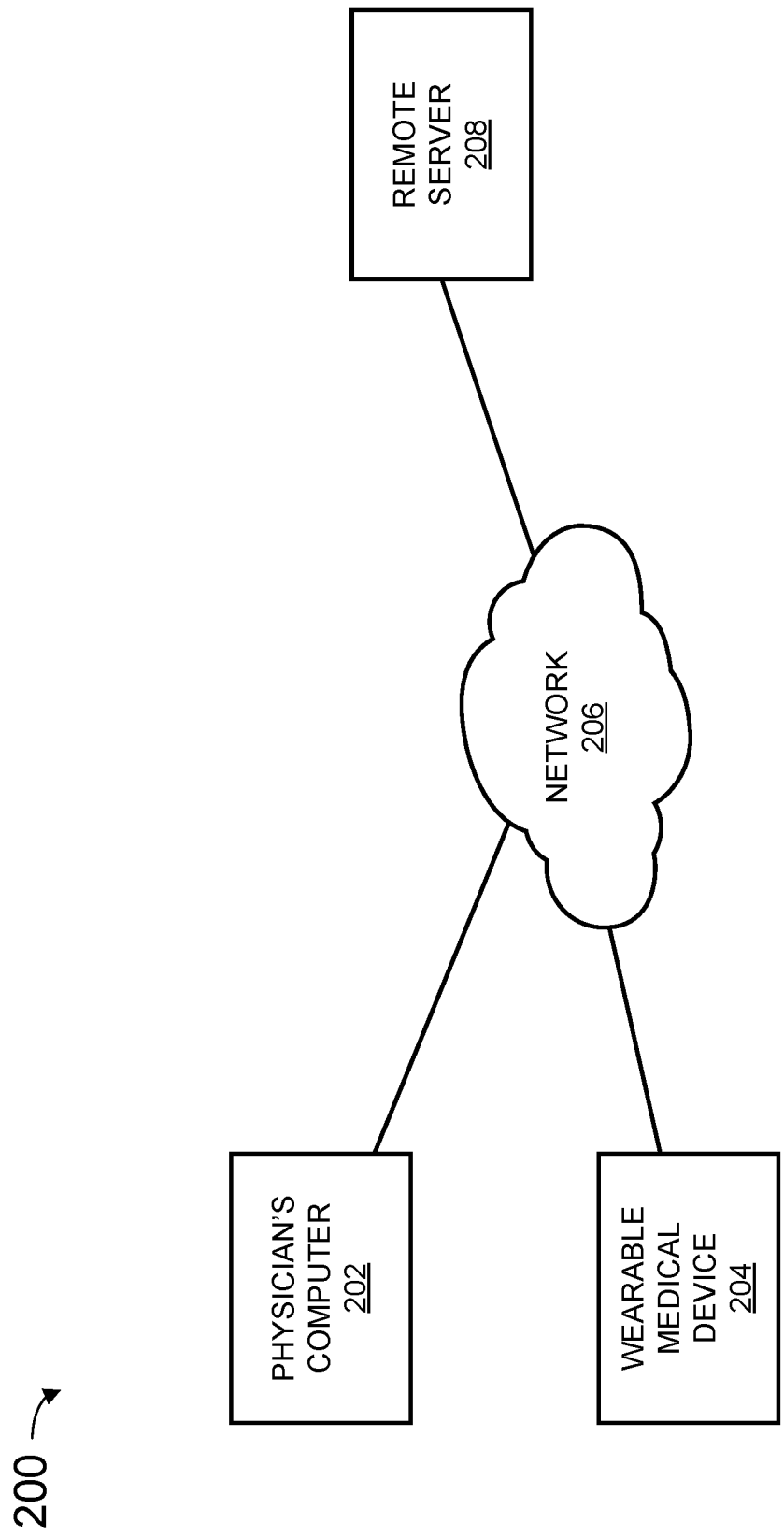
FIG. 2 depicts a sample network overview, in accordance with an example of the present disclosure.

FIG. 2 illustrates a sample network 200 in which a wearable medical device (e.g., a medical device including medical device controller 100 as shown in FIG. 1) can be operably connected to a remote server. As described above in connection with FIG. 1, the wearable medical device controller 100 can include a network interface 106 for transmitting data over a wireless link such as a Bluetooth® wireless link (e.g., via a "hotspot" or other base station or intermediate device), a broadband cellular link, or a Wi-Fi™ communications link based on the IEEE 802.11 standard. As shown in FIG. 2, a doctor's computer 202 and a wearable medical device 204 can be operably connected to a monitoring server 208 through network 206. In certain implementations, while being worn, the wearable medical device 204 can collect information related to the patient such as various patient metrics and parameters as described herein. For example, the wearable medical device 204 can collect physiological and ECG data related to the patient for the period of time that the patient has been prescribed the wearable medical device. The wearable medical device 204 can also collect accelerometer data indicative of motion information associated with the patient such as number of steps taken during a time period such as 30 minutes, one hour, two hours, six hours, or one day, as well as duration information related to periods of activity such as how often and how long did a patient exercise for. Depending upon the connection to network 206, and the programming of wearable medical device 204, the wearable medical device can be configured to regularly transmit the collected information to the monitoring server 208 for storage and further processing and analysis. The network 206 may be a private, secure network configured to allow for intercommunication between authorized devices 204, computer 202, and server 208. For example, the private network may be implemented as a virtual private network (VPN) that can be formed using a plurality of encrypted communication techniques, including the creation of secure communication channels (called "tunnels") within a public network. As an example, a device 204 or computer 202 may implement a temporary or permanent dedicated communication software application to securely communicate with the server 208 via such a tunnel. The dedicated communication software application can encrypt and send messages to the server 208 and receive and decrypt messages received from the server 208. Some types of such dedicated communication software applications can embed encrypted messages in formatted data packets, so that the encrypted messages are unreadable from outside of the secure communication channel.

Figure 3:
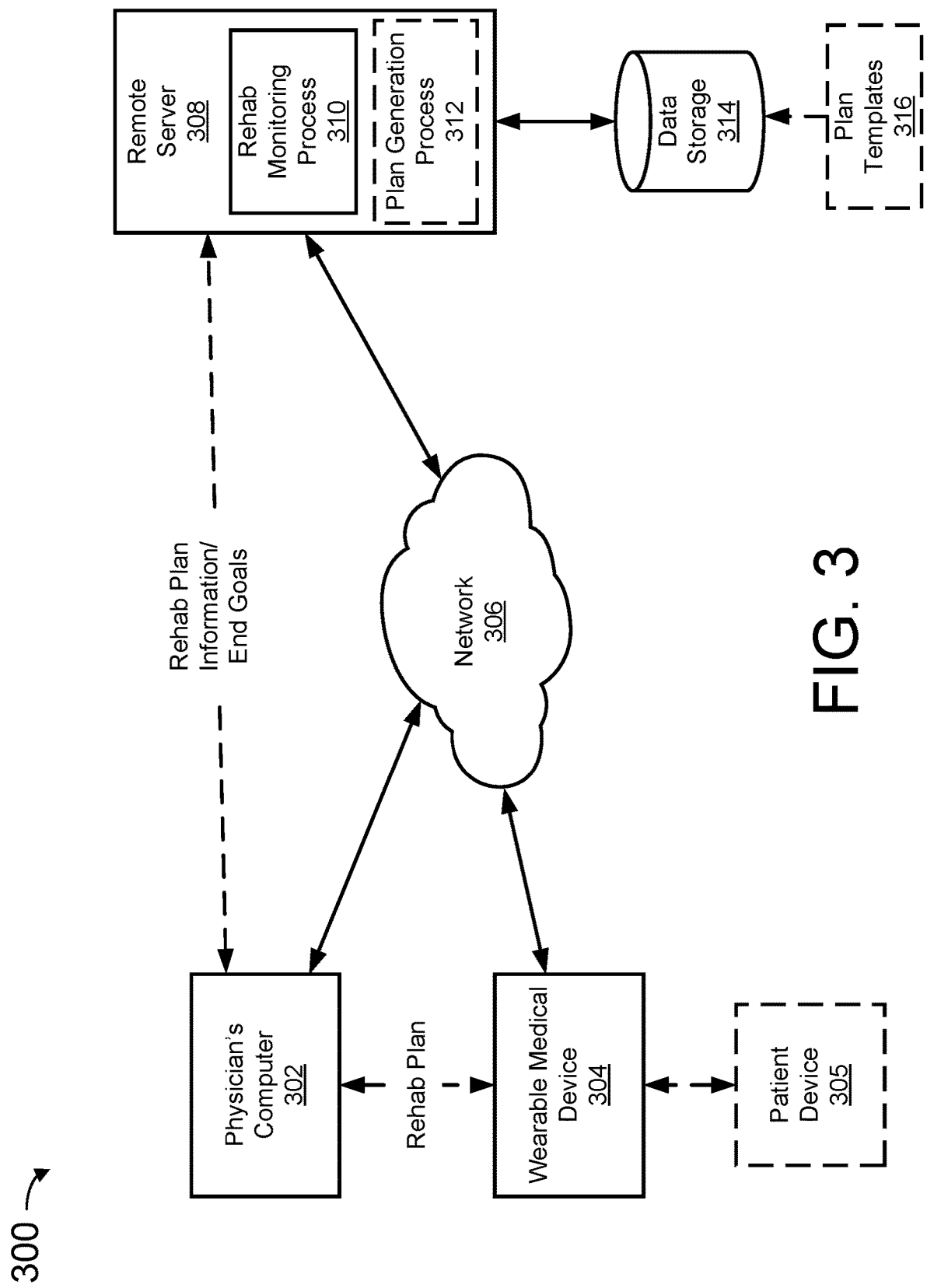
FIG. 3 depicts a second sample network overview, in accordance with an example of the present disclosure.

FIG. 3 illustrates a sample network 300 in which a remote server can be operably connected to, and configured to collect information from, a wearable medical device and a doctor's computing device. Similar to FIG. 2, a doctor's computer 302 and a wearable medical device 304 can be operably connected to a monitoring server 308 through network 306. However, to implement the processes and techniques as described herein, the monitoring server can include a cardiac rehabilitation monitoring process 310. The monitoring process 310 can be configured to use information collected from the wearable medical device 304 to monitor the patient's progress throughout a cardiac rehabilitation plan and generate one or more reports and/or notifications for review by the patient's healthcare provider based upon the patient's progress.

In some examples, the various components as included in network 300 can be configured to exchange information. For example, the doctor's computer 302 can be configured to transfer patient information, cardiac rehabilitation plan information, alert criteria, patient parameters and/or ECG metrics of interest during monitoring, and other related information to the monitoring server 308 via the network 306. Similarly, the wearable medical device 304 can be configured to transfer data collected by the wearable medical device including, but not limited to, (a) ECG data, (b) non-ECG data, including motion data, acoustical data, body fluid content information (measured, for example, using radio frequency fluid measurement techniques), and (c) other communication data such as device alerts, indications of device, system and/or arrhythmia conditions, and other similar information to the monitoring server 308 via the network 306. In certain implementations, the information received from the wearable medical device can include continuously collected information related to the patient. For example, the ECG data can include continuously collected ECG data from which a range of continuous ECG metrics can be derived as described herein. The patient information as collected herein provides for a complete collection of historical data that has been continuously collected and can be further analyzed for any specific time period, e.g., the last 24 hours, last week, two weeks ago, and other similar predefined historical periods as described herein. In some implementations, the ECG data can include discretely recorded ECG strips of predetermined lengths, ranging from a few seconds to several minutes. For instance, the ECG data can include ECG strips of 30 seconds, 1 minute, 2 minutes, 6 minutes, or 10 minutes.

For example, the ECG data can be recorded when a patient experiences and chooses to report a symptom such as fatigue, chest pain, tightness in the chest, a racing heartbeat, dizziness, and/or syncope. In implementations, the ECG data can be automatically recorded when a symptom is detected by a processor integrated into the wearable medical device (e.g., processor 118 as shown in FIG. 1) based on non-ECG physiological data, such as motion data from one or more sensors such as motion sensors. Such symptoms can include changes in a patient's gait, swaying, and patient fall. For example, the wearable medical device processor can detect one or more such symptoms by establishing a baseline of the patient's normal movements over a period of time. Then, when the patient's gait changes from the established baseline in a manner that transgresses a predetermined threshold, the wearable medical device processor can classify the movement as a change in gait and/or abnormal swaying. When such an event is detected, the patient's ECG data is automatically recorded and stored in a data storage (e.g., data storage 104 as shown in FIG. 1).

In some examples, the wearable medical device can be operably coupled to another patient device 305 such as a patient's computing device. The patient device 305 can be configured to receive data from the wearable medical device 304. In certain implementations, the patient device 305 can include a personal computer, a tablet computer, a smartphone, and other similar computing devices. In some examples, the patient device 305 can be associated with an HCP who is caring for the patient wearing the wearable medical device 304.

The monitoring server 308 can be operably connected to a data storage device 314 that is configured to store the information received from the doctor's computer 302 and the wearable medical device 304. In some examples, the data storage device 314 can be integrated into the monitoring server 308 (as described in FIG. 4 below as memory 404) or can be integrated into a separate computing device operably coupled to the monitoring server.

In some examples, the monitoring server 308 can also include a cardiac rehabilitation plan generation process 312. The plan generation process 312 can be configured, for example, to use patient-specific rehabilitation plan information and/or plan end goals as received from the physician's computer 302 to generate a patient specific cardiac rehabilitation plan. Examples of plan generation processes are described below in greater detail at, for example, the descriptions of FIGS. 5, 6, and 9A. The rehabilitation plan can be transmitted to the physician's computer for review and transmission to the wearable medical device 304 for implementation. It should be noted that the cardiac rehabilitation plan being transmitted from the physician's computer 302 to the wearable medical device 304 is shown by way of example only. In certain implementations, the wearable medical device 304 can be configured to receive the cardiac rehabilitation plan directly from the remote server 308.

In some examples, the plan generation process 312 as implemented by the remote server 308 can access one or more plan templates 316 stored on the data storage 314 to provide a framework for generating a patient-specific cardiac rehabilitation plan as described herein. For instance, in certain implementations, the one or more plan templates 316 can include one or more pre-set cardiac rehabilitation plans that are based upon the difficulty of physical activities to be performed in exercise sessions. These pre-set cardiac rehabilitation plans can be classified, for example, as "easy," "medium," and "hard." Further, in some examples, each of the pre-set cardiac rehabilitation plans can correspond to a classification of a patient, such as provided by the ACC/AHA cardiac patient classification scheme. Thus, in at least one example, the pre-set cardiac rehabilitation plans include plans for each of the following stages.

Stage A: Patients at risk for heart failure who have not yet developed structural heart changes (i.e. those with diabetes, those with coronary disease without prior infarct)

Stage B: Patients with structural heart disease (i.e. reduced ejection fraction, left ventricular hypertrophy, chamber enlargement) who have not yet developed symptoms of heart failure Stage C: Patients who have developed clinical heart failure Stage D: Patients with refractory heart failure requiring advanced intervention (i.e. biventricular pacemakers, left ventricular assist device, transplantation)

Additionally, in certain implementations the plan generation process 312 as implemented by the remote server 308 can access one or more exercise sessions from a library of pre-defined exercise sessions that can be used when populating a cardiac rehabilitation plan. Examples of accessing a library of pre-defined exercise sessions is described below, for example, in the discussion of FIG. 9A.

Figure 4:
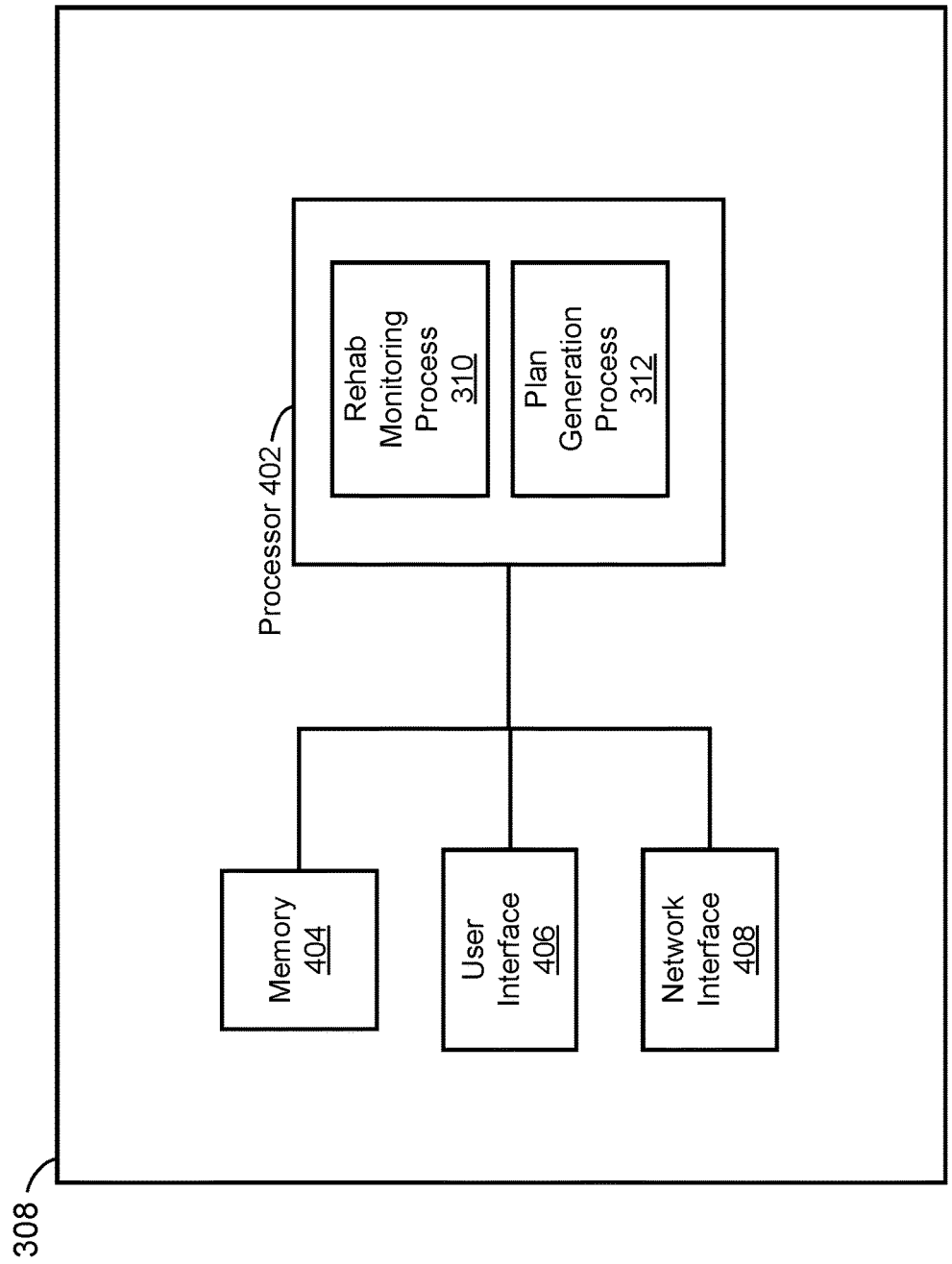
FIG. 4 depicts a schematic view of a remote computing device, in accordance with an example of the present disclosure.

FIG. 4 illustrates a sample architecture of a remote computing device such as monitoring server 308 as described above. As seen in FIG. 4, the monitoring server 308 can include a processor 402, a memory 404, a user interface 406, and a network interface 408.

In some implementations, the processor 402 can be configured to implement one or both of cardiac rehabilitation monitoring process 310 and cardiac rehabilitation plan generation process 312 as described herein. The memory 404 can be configured to store executable instructions and data used for operation of the monitoring server 308. In certain examples, the memory 404 can include executable instructions that, when executed, are configured to cause the processor 402 to perform one or more operations. In some examples, the memory 404 can be configured to store information such as ECG and patient motion data as received from, for example, a wearable medical device such as wearable medical device 304 as shown in FIG. 3. Similarly, in some examples, the memory 404 can be configured to store cardiac rehabilitation and patient information received from, for example, a healthcare provider's computer such as physician's computer 302 as shown in FIG. 3. In certain examples, the user interface 406 can receive input or provide output, thereby enabling a user to interact with the monitoring server 308. For example, the user interface 406 can be implemented as one or more remote computing devices configured to interface with the server 308 via the network interface 408. The user interface 406 in such instances can include desktop computers, workstations, laptops, handheld devices, smart phones, smart watches, and/or combination thereof. In some examples, the network interface 408 can facilitate the communication of information between the monitoring server 308 and one or more other devices or entities over a communications network. For instance, in the example as illustrated in FIG. 3, the network interface 408 can be configured to communicate with one or more remote communicating devices such as physician's computer 302 and wearable medical device 304 via a network such as network 306 using, for example, a wired or wireless connection between the network interface and the network. FIG. 4 is described in greater detail below.

The processes as described herein can provide for an improved cardiac rehabilitation process for both patients and HCPs. The patients have the added benefit that the cardiac rehabilitation plans can be dynamically updated while minimizing necessary office visits. The HCPs have the added benefit of receiving more information such as adherence and cardiac rehabilitation progression information on an on-going, as-needed, or requested basis.

Figure 5:
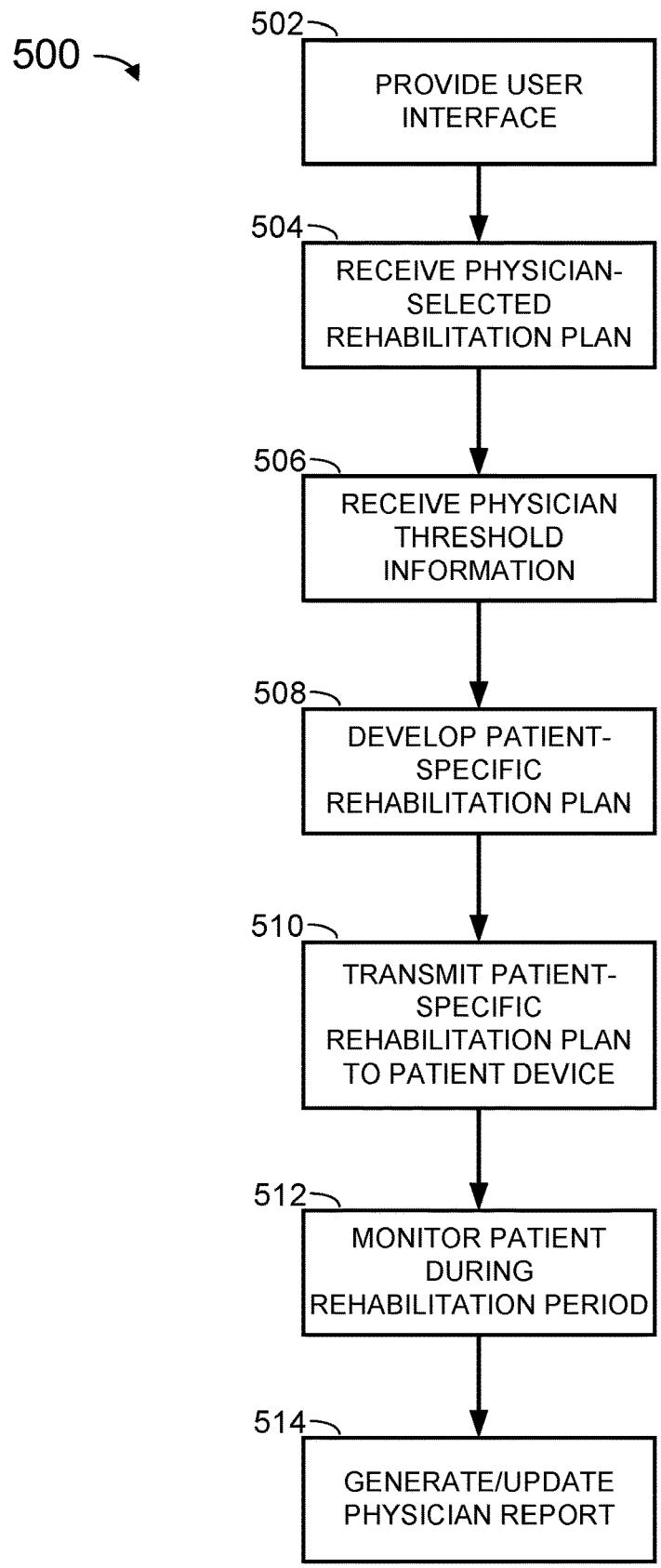
FIG. 5 depicts a sample process flow for developing a patient-specific cardiac rehabilitation plan, in accordance with an example of the present disclosure.

FIG. 5 illustrates a sample overview process 500 for generating a patient-specific cardiac rehabilitation plan and monitoring the patient as they progress through the plan during a rehabilitation period. A processing device such as processor 402 of remote server 308 and/or the processor 118 of the medical device controller 100 can be configured to implement at least a portion of the process 500 as shown in FIG. 5.

As shown in FIG. 5, the process 500 starts with the processor providing 502 a user interface to an HCP. For example, the processor can execute a web server that is configured to serve a web site to a browser executing on a computing device associated with the HCP. Alternatively or additionally, the processor can execute an application local to the computing device that is configured to interoperate, directly or through an intermediate device, with the patient's wearable medical device. FIG. 7C illustrates one example of a user interface screen that the processor is configured to provide 502 according to some examples.

As shown, FIG. 7C illustrates a sample view of a user interface screen 715 that can be accessed and utilized by a physician and/or other HCP to generate a cardiac rehabilitation plan for a cardiac patient. For example, the user interface screen 715 can be implemented as a portion of the plan generation process 312 as described above. The physician can access user interface 406 as described above to interact with the user interface screen 715.

As illustrated in FIG. 7C, the user interface screen 715 includes user interface controls 716, 718, 720, and 722. In some examples, the user interface control 716 provides access to patient specific information such as the cardiac patient's name and an identifier associated with the cardiac patient. In certain implementations, the patient identifier can be a medical records number associated with the cardiac patient, an insurance identification number associated with the cardiac patient, a number that directly identifies the cardiac patient such as a social security number, or another similar identification number. Based upon the patient specific information, the processor can access the cardiac patient's medical record. Based upon information contained in the medical record such as patient condition information, historical patient information, demographic information, and rehabilitation baselining information, the processor can generate a recommended plan without additional information from the physician. The user interface control 718 can include a button or other selectable control. In some examples, the processor responds to input selecting the user interface control by automatically generating a recommended cardiac rehabilitation plan for the patient. This recommended rehabilitation plan can be based on a plan template (e.g., a plan template selected from the one or more plan templates 316 of FIG. 3). For instance, the processor can be configured to recommend a rehabilitation plan from the one or more plan templates that correspond with the ACC/AHA classification of the patient.

Figure 7A:
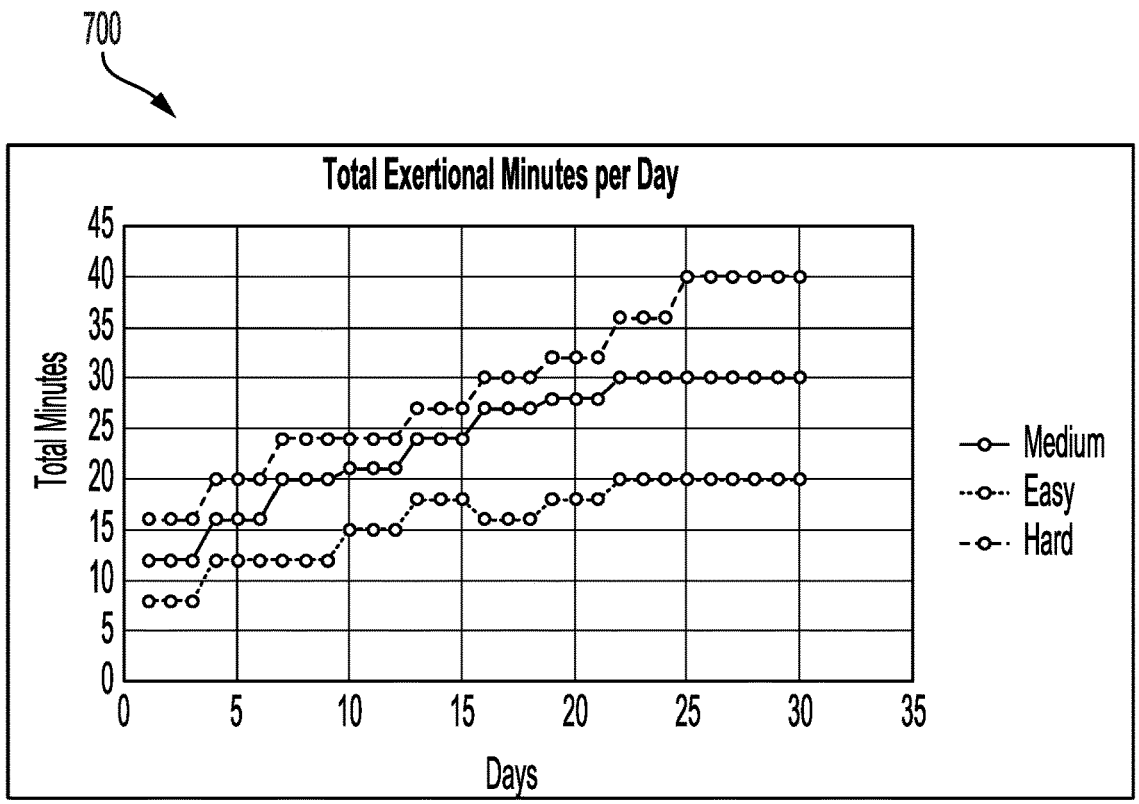
FIG. 7A depicts a graph showing various difficulty levels for a cardiac rehabilitation plan, in accordance with an example of the present disclosure.

For example, for patients falling into Stage A, the processor can recommend a "hard" cardiac rehabilitation plan. For patients falling into Stage B, the processor can recommend a "medium" cardiac rehabilitation plan. For patients falling into Stage C or Stage D, the processor can recommend an "easy" cardiac rehabilitation plan. FIG. 7A illustrates a comparison of sample of an "easy," "medium," and "hard" cardiac rehabilitation plans. As shown in graph 700, the "easy" cardiac rehabilitation plan requires less total exertional minutes per day than the "medium" cardiac rehabilitation plan, and the "medium" cardiac rehabilitation plan requires less total exertional minutes per day than the "hard" cardiac rehabilitation plan.

Additionally or alternatively, the user interface control 720 can provide access to a set of available plan controls 720a-720d. As shown, the set of available plan controls can include, for example, a list of available cardiac rehabilitation plan options from which the physician can select. For example, as shown in FIG. 7C, the set of available plan controls 720a-720d includes a hard plan control 720a, a medium plan control 720b, an easy plan control 720c, and a custom plan control 720d. Each of the set of available plan controls 720a-720d can further include one or more notes. For example, hard plan control 720a can include notes indicating that the "hard" plan requires the highest initial exertion levels and is recommended for ACC/AHA Stage A patients, medium plan control 720b can include notes indicating that the "medium" plan has moderate initial exertion levels and is recommended for ACC/AHA Stage B patients, easy plan control 720c can include notes indicating the "easy" plan has the lowest initial exertion levels (as compared to, for example, the "medium" and "hard" plans) and is recommended for ACC/AHA Stage C and Stage D patients, the custom plan control 720d can include a note indicating that selection of that control launches a plan customizer interface, which is described below in the discussion of FIG. 7D.

As shown in FIG. 7C, the user interface control 722 includes a set of selectable buttons. In response to receiving a selection of the "submit" button, the processor can generate a cardiac rehabilitation plan for the patient as described herein. In response to receiving a selection of the "clear" button, the processor can delete existing selections and/or entered information from the user interface screen 715. In response to receiving a section of the "cancel" button, the processor can abort plan generation.

FIG. 7D illustrates a sample user interface screen 725 that the processor can provide to a physician in response to, for example, receiving a selection of the plan control 720d of FIG. 7C by the physician. For example, the user interface screen 725 can be implemented as a portion of the plan generation process 312 as described above. The processor can provide the user interface screen 725 to interact with the physician via user interface 406 of FIG. 4.

As illustrated in FIG. 7D, the user interface screen 725 includes user interface controls 726, 728, 730, and 732. In some examples, the user interface control 726 provides a physician with the option to customize an existing plan. In certain implementations, the user interface control 726 can provide the physician with the option to select from one of a "hard" cardiac rehabilitation plan, a "medium" cardiac rehabilitation, or an "easy" cardiac rehabilitation plan to customize. Upon selection of a plan and selecting the user interface control 726, the processor can present the physician with one or more options to alter at least a portion of an existing cardiac rehabilitation plan.

Alternatively, the user interface control 728 can provide the physician with the option to create a completely custom and individualized plan for a cardiac patient. For example, as shown in FIG. 7D, the user interface control 728 can display one or more specific exercise sessions to the physician for customization and inclusion in the custom cardiac rehabilitation plan. For example, the user interface control 728 can provide a set of parameters 728a to the physician. The parameters 728a can represent specific details for a first exercise session. In this example, the physician selects walking from a drop-down list of available exercise types provided within the user interface control 728 for exercise session 1. The processor can receive this selection and execute subsequent processing based on the selection. For instance, in certain implementations, depending upon the type of exercise session selected, the processor can display one or more additional fillable fields on user interface screen 725 for completion by the physician. As shown in FIG. 7D, the set of parameters 728a can include frequency, starting duration, ending duration, and target pace. However, it should be noted that these individual parameters are shown by way of example only. In some examples, the set of parameters 728a can include fewer or additional parameters as needed to provide adequate information for generating a custom cardiac rehabilitation plan. For example, as shown in FIG. 7D, the physician selects, and the processor receives, a frequency of daily, a starting duration of 10 minutes, an ending duration of 30 minutes, and a target pace of 60 steps per minute for parameters 728a. It should be noted that, as described herein, starting duration is the expected duration of the exercise session at the beginning of the cardiac rehabilitation plan and the ending duration is the expected or target duration at the completion of the cardiac rehabilitation plan. The cardiac rehabilitation plan generation process (e.g., plan generation process 312 as described herein) can be configured to generate a daily schedule of exercise sessions that are selected to increase the patient's cardiovascular health to reach the ending duration targets.

Referring again to FIG. 7D, the user interface control 728 can further provide a set of parameters 728b to the physician for providing related details for a second exercise session. In this example, the physician can select exercise session 2 as cycling. As above, in response to receiving the selection of cycling, the processor can display additional fields in user interface screen 725 that are related to the exercise type for completion by the physician such as frequency, starting duration, ending duration, and target speed. For example, as shown in FIG. 7D, the physician selects, and the processor receives, a frequency of three times per week, a starting duration of 15 minutes, an ending duration of 30 minutes, and a target speed of 10 miles per hour.

As further shown in FIG. 7D, the user interface control 728 can provide another set of parameters 728c for a third exercise session. In this example, the physician can select weight training to be exercise session 3. As above, the processor can receive this selection and display additional fields that are related to the exercise type for completion by the physician, such as frequency, starting repetitions, ending repetitions, and target weight. For example, as shown in FIG. 7D, the physician selects, and the processor receives, a frequency of two times per week, a starting repetition number of 10 repetitions, an ending repetition number of 25 repetitions, and a target weight of five pounds.

It should be noted that three exercise sessions and exercise types are shown in FIG. 7D by way of example only. In certain implementations, the physician can provide more or fewer exercise sessions. For example, the physician can include four exercise sessions in cardiac rehabilitation plan for a particular patient. In such an example, the user interface screen 725 can provide a user-selectable control for a physician to include an additional exercise session and a set of related parameters as described above.

In addition to the custom and individualized plan options related to user interface control 728, the user interface screen 725 can also provide the physician with the option to provide one or more general settings options using interface controls 730. For example, the general settings options can apply to the cardiac rehabilitation plan as a whole rather than any specific exercise session. For example, as shown in FIG. 7D, the user interface controls 730 can provide the physician with an option to provide heart rate information such as target heart rate and maximum heart rate. As shown in FIG. 7D, the physician has provided 100 bpm for a target heart rate and 120 as a maximum heart rate. For added convenience, the user interface screen 725 can further provide a note regarding recommended maximum heart rate levels. For example, as shown, the note can provide a reminder that ACC/AHA Stage A patients can have a recommended maximum heart rate of 150 bpm, ACC/AHA Stage B patients can have a recommended maximum heart rate of 135 bpm, ACC/AHA Stage C patients can have a recommended maximum heart rate of 120 bpm, and ACC/AHA Stage D patients can have a recommended maximum heart rate of 100 bpm.

Additionally, the user interface control 730 can provide additional general setting controls such as a maximum exercise sessions per day control. The maximum exercise sessions per day control can provide the physician with an option to limit the number of exercise sessions a patient is scheduled in a single day. For example, as shown in FIG. 7D, the physician selects, and the processor receives, a maximum of 2 exercise sessions per day. In addition, as shown in FIG. 7D, the physician selects exercise session 1 (walking) to occur daily (seven exercise sessions per week), exercise session 2 (cycling) to occur three times per week, and exercise session 3 (weight training) to occur two times per week, for a total of 12 exercise sessions per week. Thus, if the physician selects a maximum of one exercise session per day, the user interface screen 725 can provide a warning that the total number of prescribed exercise sessions a week exceeds the total number of available exercise sessions to be scheduled for the patient. Alternatively or additionally, in certain implementations, the user interface screen 725 can provide another user interface control to display and receive values for a minimum number of exercise sessions per day. In these implementations, the processor can provide, via the user interface screen 725, a warning if the physician fails to select a high enough number of exercise sessions per day.

The user interface control 730 can also provide a plan length control. The plan length control can provide the physician with an option to select the overall length of the cardiac rehabilitation plan (e.g., the rehabilitation period as described herein). For example, as shown in FIG. 7D, the physician selects, and the processor receives, a plan length of 30 days. In certain implementations, the physician can select any length of a rehabilitation period. In some implementations, the physician can select from a set of rehabilitation periods including, for example, periods between about 2 days and about at least one of 1 week, 2 weeks, 4 weeks, 3 months, 6 months, one year, two years, and three years.

As shown in FIG. 7D, the user interface control 732 includes a set of selectable buttons. Upon completion of the custom plan options and the general settings options, the physician can select one of the buttons included in the user interface control 732. In response to receiving a selection of the "submit" button, the processor can generate a customized cardiac rehabilitation plan for the patient as described herein, the customized plan including the custom plan options and general settings options as selected by the physician. In response to receiving a selection of the "clear" button, the processor can delete existing selections and/or entered information from the user interface screen 725. In response to receiving a selection of the "cancel" button, the processor can abort the customized cardiac rehabilitation plan generation.

It should be noted that the set of physician selectable parameters as described herein, such as shown in FIGS. 7C and 7D and described above, can be modified as a patient advances through a specific cardiac rehabilitation plan during a rehabilitation period as described herein.

Returning to process 500 of FIG. 5, the processor can receive 504 a physician-selected cardiac rehabilitation plan for a specific patient. For example, the processor can receive 504 the rehabilitation plan selected and/or entered by a physician via the user interface screens 715 and/or 725 described above.

The process 500 can further include the processor receiving 506 threshold information from an HCP via, for example, the user interface control 730 of the user interface screen 725. As noted above, several parameters are reviewed prior to and during an exercise session to determine if a patient should participate in an exercise session or if an exercise session should be stopped. The processor can provide values for these parameters to the HCP via the user interface controls 730 or use a set of default values already associated with one or more cardiac rehabilitation plans. For example, Table 4 below includes a sample list of parameters and thresholds that the user interface can expose to an HCP.

TABLE 4

| Parameter | Example Threshold |
|---|---|
| Shortness of Breath prior to exercise session | 3 or above on a scale of 0-10 |
| Chest Pain prior to exercise session | 3 or above on a scale of 0-10 |
| Fatigue prior to exercise session | 3 or above on a scale of 0-10 |
| Maximum Heart Rate during exercise session | Above 120bpm or more than 30 bpm above resting heart rate |
| Average Step Rate during exercise session | Above 60 steps per minute |

Figure 7B:
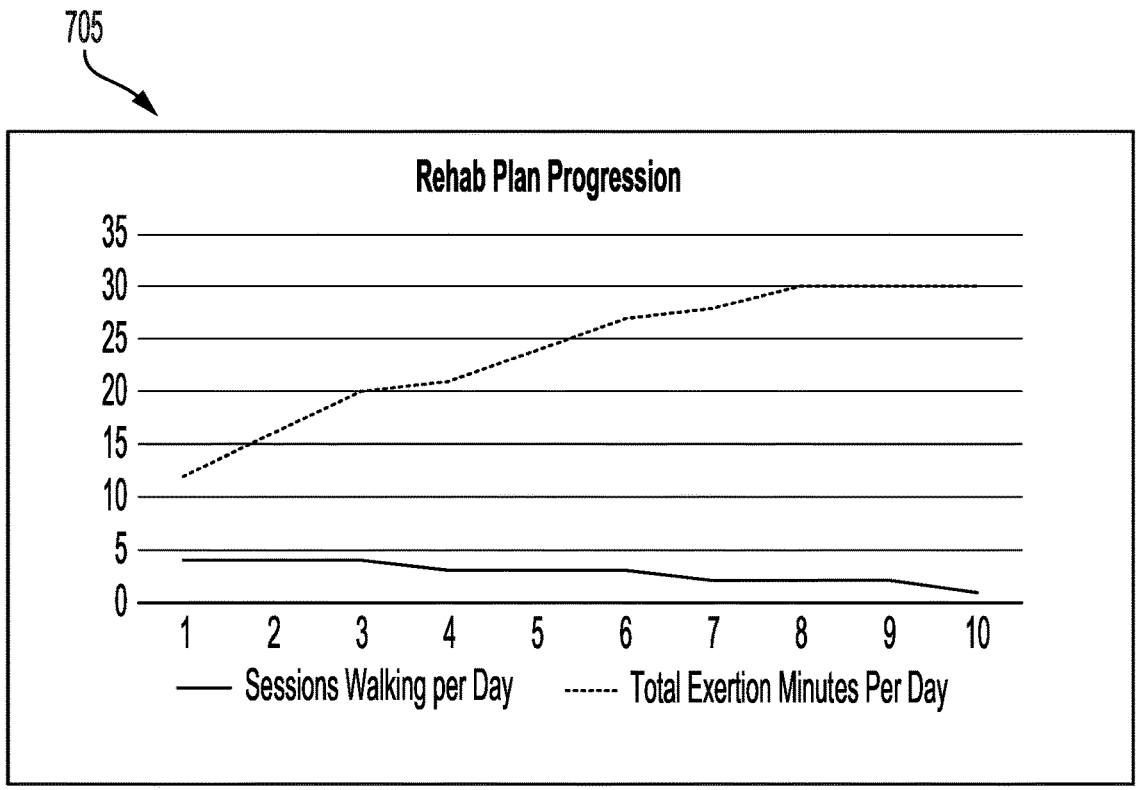
FIG. 7B depicts a graph showing a patient's progression through a cardiac rehabilitation plan, in accordance with an example of the present disclosure.

Based upon the threshold information, the processor can develop 508 a patient-specific cardiac rehabilitation plan. For example, the processor can identify a series of physical exercise sessions selected based upon the selected difficulty level as described above and include the identified exercise sessions in the rehabilitation plan. The threshold information for monitoring and determining patient progression through the cardiac rehabilitation plan can include the HCP-provided threshold information as described above. Once developed, the processor can transmit 510 the patient-specific plan to a patient device such as a WCD prescribed to the patient and cause the patient device to administer the cardiac rehabilitation plan. During administration of the cardiac rehabilitation plan over a rehabilitation period, the processor can monitor 512 the patient's progress and generate 514 one or more physician reports for review by the patient's HCP. For example, FIG. 7B illustrates a sample graph 705 illustrating a patient's progress through a cardiac rehabilitation plan, highlighting the total exertion minutes per day as compared to total walking sessions per day. As shown in graph 705, the patient is reducing the number of walking sessions per day while increasing their overall exertion minutes, thereby indicating that the patient is increasing the total number of exertion minutes per walking session, i.e., the patient is walking for a longer time per session. Additional detail related to execution of cardiac rehabilitation plans and monitoring patient progress is described below.

Figure 6:
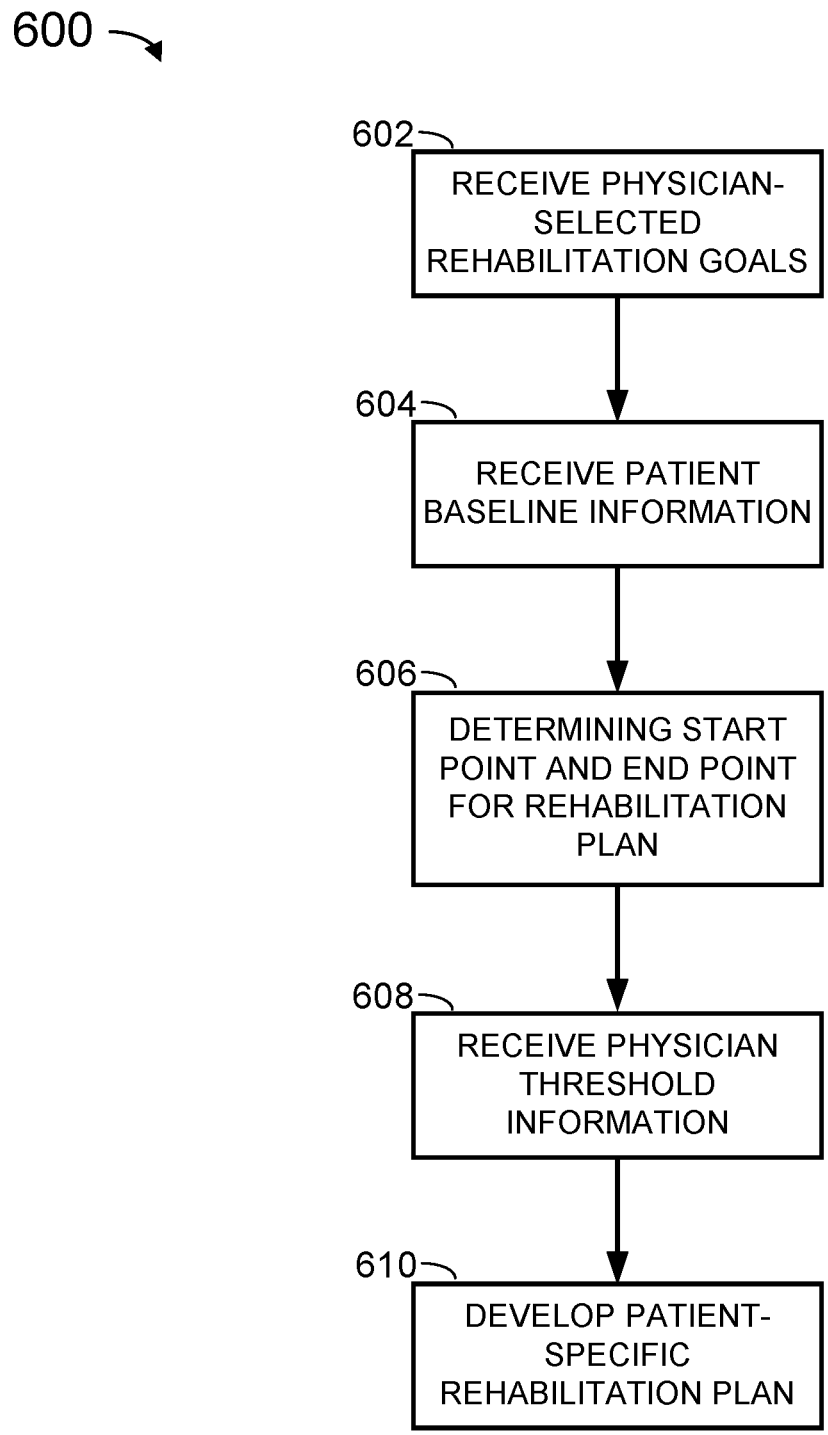
FIG. 6 depicts a sample process flow for generating a patient-specific cardiac rehabilitation plan based upon physician-provided goals, in accordance with an example of the present disclosure.

In certain implementations, rather than use a pre-existing cardiac rehabilitation plan, an HCP can use an automated process such as plan generation process 312 as described above to generate a patient-specific cardiac rehabilitation plan. Process 600 as shown in FIG. 6 illustrates a sample process for generating such a patient-specific cardiac rehabilitation plan. As shown in process 600, a processor such as processor 402 and/or the processor 118 as described above can receive 602 one or more physician-selected cardiac rehabilitation goals from a patient's HCP. For example, the goals can include one or more desired physical activities that the patient should be able to complete upon the end of the cardiac rehabilitation plan. In certain implementations, the goals can include taking one 30-minute walk a day without pausing or resting while maintaining a pace of 60 steps per minute. In other examples, the goal can include walking a particular distance such as 1.5 miles without pausing or resting.

For example, FIG. 7E illustrates a sample user interface screen 735 that the processor can provide to a physician in response to, for example, receiving a selection of the plan control 718 of FIG. 7C by the physician to generate a recommended plan based upon starting information and goal information provided by a patient's physician. For example, the user interface screen 735 can be implemented as a portion of the plan generation process 312 as described above. The processor can provide the user interface screen 735 to interact with the physician via user interface 406 of FIG. 4.

As illustrated in FIG. 7E, the user interface screen 735 includes user interface controls 736, 738, and 740. In some examples, the user interface control 736 provides a physician with the option to provide starting information for a patient. For example, the starting information can include information related to completion of one or more exercise sessions by the patient prior to discharge from the hospital. For example, as shown in FIG. 7E, the user interface control 736 can provide a set of parameters 736a to the physician.

The parameters 736a can represent specific details from a first exercise session completed by the patient. In this example, the physician can select walking from a drop-down list of available exercise types provided within the user interface control 736 for exercise session 1. The processor can receive this selection and execute subsequent processing based on the selection. For instance, in certain implementations, depending upon the type of exercise session selected, the processor can display one or more additional fillable fields on user interface screen 735 for completion by the physician. As shown in FIG. 7E, the set of parameters 736a can include date completed, duration, maximum heart rate, and average pace. However, it should be noted that these individual parameters are shown by way of example only. In some examples, the set of parameters 736a can include fewer or additional parameters as needed to provide adequate information for generating a custom cardiac rehabilitation plan. For example, as shown in FIG. 7E, the physician selects, and the processor receives, a date completed of Jan. 1, 2019, a duration of six minutes, a maximum heart rate of 115 bpm, and an average pace of 56 steps/minute.

The user interface control 736 can further provide a set of parameters 736b to the physician for providing related details for a second exercise session completed by the patient. In this example, the physician can select exercise session 2 as cycling. As above, in response to receiving the selection of cycling, the processor can display additional fields in user interface screen 735 that are related to the exercise type for completion by the physician such as date completed, duration, maximum heart rate, and average speed. For example, as shown in FIG. 7E, the physician selects, and the processor receives, a completed date of Jan. 2, 2019, a duration of eight minutes, a maximum heart rate of 120 bpm, and an average speed of eight miles per hour.

It should be noted that two completed exercise sessions and exercise types are shown in FIG. 7E by way of example only. In certain implementations, the physician can provide information for more or fewer exercise sessions depending upon, for example, how many exercise sessions the patient has previously completed.

In addition to the starting information related to user interface control 736, the user interface screen 735 can also provide the physician with the option to provide one or more target goal information options using interface control 738. As described herein, the target goal information can define one or more physician-selected goals for the patient to achieve or work toward during progression through and completion of a cardiac rehabilitation plan.

The user interface control 738 can provide a set of parameters 738a to the physician. The parameters 738a can represent specific details related to a first goal to be achieved by the patient at the completion of the cardiac rehabilitation plan. In this example, the physician can select walking from a drop-down list of available exercise types provided within the user interface control for the first goal. The processor can receive this selection and execute subsequent processing based on the selection. For instance, in certain implementation, depending upon the type of exercise selected for the first goal, the processor can display one or more additional fillable fields on user interface screen 735 for completion by the physician. As shown in FIG. 7E, the set of parameters 738a can include target heart rate, target duration, and target pace for Exercise 1 as associated with the first goal. For example, as shown in FIG. 7E, the physician selects, and the processor receives, a target heart rate of 115 bpm, a target duration of 25 minutes, and a target pace of 70 steps per minute.

The user interface control 738 can further provide a set of parameters 738b to the physician. The parameters 738b can represent specific details related to a second goal to be achieved by the patient at the completion of the cardiac rehabilitation plan. In this example, the physician can select cycling from a drop-down list of available exercise types provided within the user interface control for the second goal. The processor can receive this selection and execute subsequent processing based on the selection. For instance, in certain implementation, depending upon the type of exercise selected for the second goal, the processor can display one or more additional fillable fields on user interface screen 735 for completion by the physician. As shown in FIG. 7E, the set of parameters 738b can include target heart rate, target duration, and target speed for Exercise 2 as associated with the second goal. For example, as shown in FIG. 7E, the physician selects, and the processor receives, a target heart rate of 120 bpm, a target duration of 25 minutes, and a target speed of 12 miles per hour.

As shown in FIG. 7E, the user interface control 740 includes a set of selectable buttons. Upon completion of the starting information and target goal information, the physician can select one of the buttons included in the user interface control 740. In response to receiving a selection of the "submit" button, the processor can generate a cardiac rehabilitation plan for the patient as described herein, the plan a selection of exercise sessions chosen and organized to assist the patient in progressing from the starting information to the target goal information. In response to receiving a selection of the "clear" button, the processor can delete existing selections and/or entered information from the user interface screen 735. In response to receiving a selection of the "cancel" button, the processor can abort the cardiac rehabilitation plan generation.

It should be noted that the set physician selectable parameters as described herein, such as shown in FIG. 7E and described above, can be modified as a patient advances through a specific cardiac rehabilitation plan during a rehabilitation period as described herein.

Referring back to FIG. 6, the processor can also receive 604 patient baseline information. This information can include previous exercise session information collected for the patient prior to discharge. For example, the baseline information can include information from a 6-minute walk test that the patient completed prior to discharge. In certain implementations, the baseline information can include starting information as described above in the discussion of FIG. 7E. The baseline information can include distance traveled during the test, average pace during the test, average heart rate during the test, maximum heart rate during the test, and other similar baseline information. The processor can use the goals and baseline information to determine 606 a start point and an end point for the cardiac rehabilitation plan. The processor can also receive 608 threshold information for the cardiac rehabilitation plan as outlined above. Based upon the start point, end point, threshold information, and other information collected during process 600, the processor can develop 610 a patient-specific rehabilitation plan for transmission to and execution on a patient device using a similar process as, for example, process 500 described above in FIG. 5 or process 800 described below in the discussion of FIGS. 8 and 9A.

As noted above, there are inherent drawbacks with some approaches to cardiac rehabilitation, for example, where a patient is required to make regular office visits and their progression through the rehabilitation plan is closely monitored. Based upon this in-person monitoring, a professional who is coordinating the patient's cardiac rehabilitation has the option to modify or adjust the cardiac rehabilitation plan based upon the patient's progression and response to the plan. However, as also noted above, by requiring patients to attend regular office visits for monitored exercise sessions, the number of patients who complete a cardiac rehabilitation program is low. The concepts as described herein use the monitoring and reporting capabilities of a wearable medical device such as a WCD to reduce or eliminate the need for a cardiac patient to attend cardiac rehabilitation exercise sessions at a specific location. Rather, the patient can perform the exercise sessions at home or another similarly convenient location while wearing the medical device. Information received from the wearable medical device can be reported back to a remote server for processing and evaluation. Based upon the information, the remote server can determine the patient's progression through the cardiac rehabilitation plan and dynamically adjust the plan to better suit the patient.

For example, as shown in FIG. 3, a cardiac patient may be prescribed a wearable medical device 304 prior to or upon discharge from the hospital. In certain implementations, the wearable medical device 304 can include a monitoring and treatment device such as a WCD. Upon enrollment in an outpatient cardiac rehabilitation program, a cardiac rehabilitation plan can be loaded on the wearable medical device 304. The wearable medical device 304 can be programmed to administer the cardiac rehabilitation plan and record patient information related to the patient's progression through and response to the cardiac rehabilitation plan. This information can be transmitted by the wearable medical device 304 to, for example, the remote server 308 for evaluation. Based upon the evaluation, the remote server 308 can dynamically adjust the rehabilitation plan and transmit the adjusted plan to the wearable medical device 304 for implementation. The wearable medical device 304 can then execute the adjusted cardiac rehabilitation plan accordingly.

Figure 8:
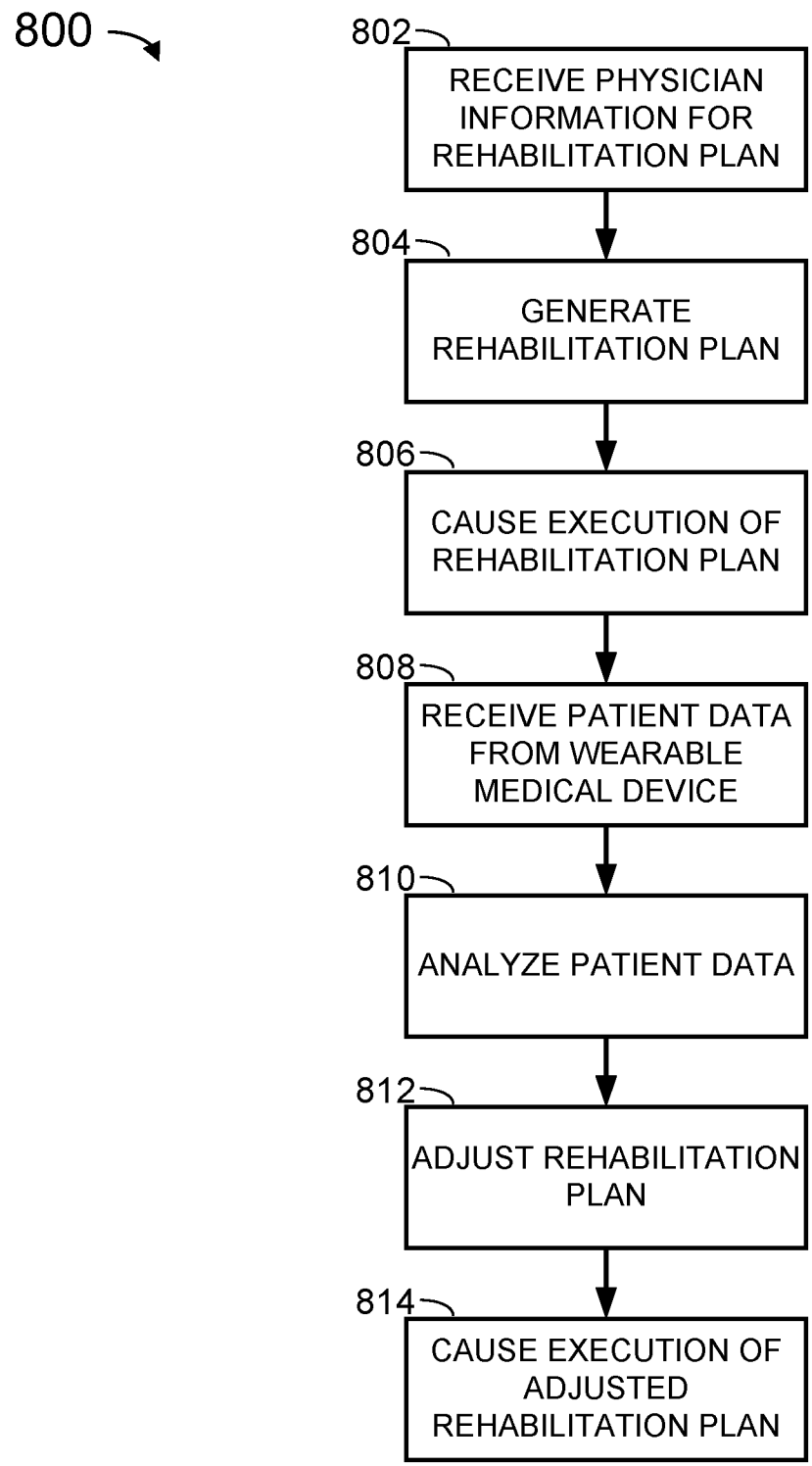
FIG. 8 depicts a sample process flow for dynamically adjusting a cardiac rehabilitation plan, in accordance with an example of the present disclosure.

FIG. 8 illustrates a sample process 800 for execution by, for example, a processor such as processor 402 of remote server 308 for dynamically adjusting a cardiac rehabilitation plan. However, it should be noted that at least a portion of the process 800 as shown in FIG. 8 can be implemented by a processor associated with, for example, a wearable medical device such as the wearable medical device 304 or, in certain implementations, by the processor 118 of the medical device controller 100 as described above.

Figure 9A:
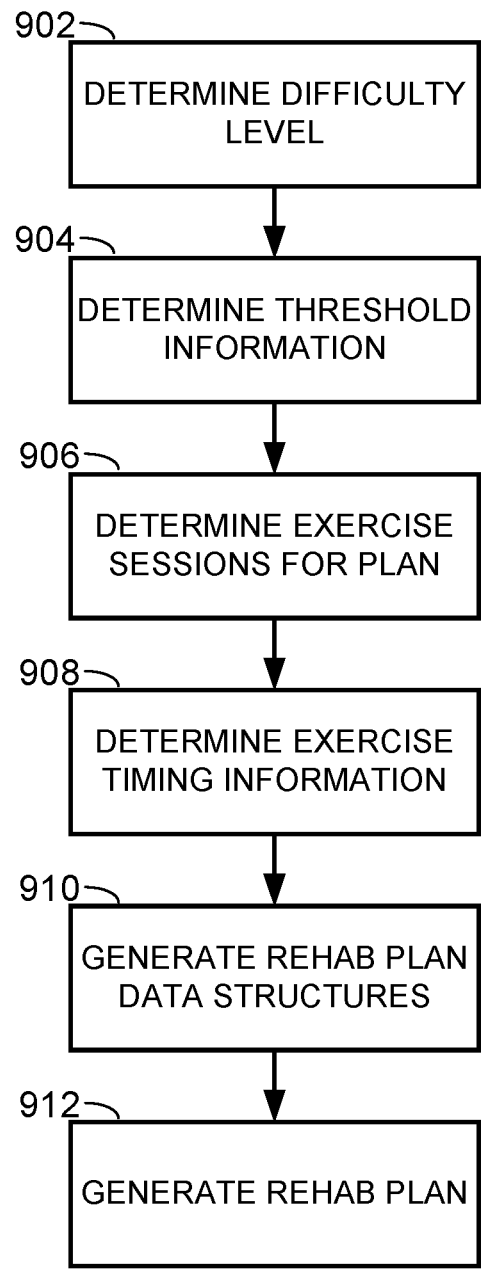
FIG. 9A depicts a sample process flow for generating a cardiac rehabilitation plan as shown in FIG. 8, in accordance with an example of the present disclosure.

As shown in FIG. 8, the processor can receive 802 physician-provided information for a cardiac rehabilitation plan and, based upon the received information, generate 804 the cardiac rehabilitation plan. For example, the processor can provide user interfaces similar to those as shown in FIGS. 7C, 7D and 7E, and receive physician-provided information as it is entered into the user interface(s). FIG. 9A illustrates an expanded set of process actions for generating 804 a cardiac rehabilitation plan, similar to processes 500 and 600 as shown in FIGS. 5 and 6 and as described above. However, FIG. 9A provides additional detail for an alternative process for generating a cardiac rehabilitation plan for a specific patient. For example, the processor can determine 902 an associated difficulty level for the cardiac rehabilitation plan based upon the physician-provided information. As noted above, the difficulty level for a cardiac rehabilitation plan can be labeled with a descriptor such as "easy," "medium," and "hard" as described herein, the difficulty levels providing an indication of how strenuous the cardiac rehabilitation plan is and how much exertion is required as the patient progresses through the plan and completes various exercise sessions. In certain implementations, the difficulty level of a cardiac rehabilitation plan can be automatically determined 902 based upon the patient's condition as determined from, for example, the patient's medical record or as provided by the physician.

As further shown in FIG. 9A, the processor can further determine 904 threshold information associated with the cardiac rehabilitation plan from the physician-provided information. For example, the threshold information can include similar parameters and threshold levels as shown above in Table 4 and provided, for example, by a physician accessing a user interface such as that shown in FIG. 7D and described above. The processor can further determine 906 what exercise sessions are to be included in the cardiac rehabilitation plan for completion by the patient as the patient progresses through the plan. The processor can determine 906 the exercise sessions based upon, for example, a comparison of the difficulty level associated with the cardiac rehabilitation plan and the associated difficulty rankings for each exercise session stored, for example, in a library of exercise sessions. In certain implementations, to provide the patient with a variety of types of exercise, the processor may iteratively assign types of exercise to sequence exercise sessions using a round-robin scheme.

In these implementations, the processor can draw from a library of pre-defined exercise sessions when populating a cardiac rehabilitation plan. The library of pre-defined exercise sessions can include standardized exercise sessions that have an associated, pre-assigned difficulty ranking. The difficulty ranking can be determined by, for example, a physical therapist or other similar HCP who analyzes various characteristics of the exercise session such as duration, target pace or speed, target heart rate, and other similar characteristics, and assigns a numerical ranking for each exercise session. In certain examples, the difficulty ranking of each exercise session can be on a scale of 1-5, wherein 1 is the most difficult and 5 is the easiest. The assigned difficulty rankings can be used, for example, when determining exercise sessions for populating a cardiac rehabilitation plan to ensure that a certain difficulty level of plan is populated with appropriate exercises. For example, a "hard" cardiac rehabilitation plan can include a larger number of exercise sessions having a difficulty ranking of 1 while an "easy" cardiac rehabilitation plan can include a larger number of exercise sessions having a difficulty ranking of 5. Table 5 below shows a 1-5 ranking scale for indicating how difficult or challenging an exercise session is and what specific cardiac rehabilitation difficulty level can include such an exercise session.

TABLE 5

| Difficulty Ranking | Associated Plan Difficulty Level |
| --- | --- |
| 1 | Hard |
| 2 | Medium/Hard |
| 3 | Medium/Hard |
| 4 | Easy/Medium/Hard |
| 5 | Easy/Medium/Hard |

Thus, as shown in Table 5, a "hard" cardiac rehabilitation plan can include exercise sessions having any difficulty ranking 1-5, while an "easy" cardiac rehabilitation plan can include exercise sessions having a difficulty ranking of 4 or 5.

Similarly, the processor can determine 908 timing information such as duration, start time, and end time for each of the exercises. For example, the types of exercise and timing information for the exercises can be based upon the difficulty level of the cardiac rehabilitation plan. Similarly, additional information such as target pace and distance can be determined by the processor. For example, Table 6 below shows sample exercise sessions and their associated difficulty rankings:

TABLE 6

| Difficulty Ranking | Exercise Type | Notes |
| --- | --- | --- |
| 1 | Walking | 20 minutes at a 75 step per minute pace, target distance 1 mile without resting, start at 10:00 am and complete at 10:20 am |
| 2 | Walking | 12 minutes at 70 steps per minute pace, target distance 0.5 miles without resting, start at 10:00 am and complete at 10:12 am |
| 3 | Walking | 10 minutes at 65 steps per minute pace, target distance 0.35 miles with a 1-minute rest, start at 10:00 am and complete at 10:11 am |
| 4 | Walking | 6 minutes at 60 steps per minute pace, no target distance without resting, start at 10:00 am and complete at 10:06 am |

TABLE 6-continued

| Difficulty Ranking | Exercise Type | Notes |
|---|---|---|
| 5 | Walking | 6 minutes at 60 steps per minute pace, no target distance with a 1-minute rest, start at 10:00 am and complete at 10:07 am |

Based upon the threshold information, the timing information, the exercise type information, acceptable difficulty rankings for exercise sessions to be populated into a specific cardiac rehabilitation plan difficulty level (e.g., "easy," "medium," ~ or "hard"), and various other information, the processor can generate 910 one or more rehabilitation plan data structures and store the data structures in, for example, a database to generate 912 the rehabilitation plan. In certain implementations, a rehabilitation plan data structure can include a database table entry or multiple tables within, for example, an RDBMS database that can be queried using a standard querying language such as SQL. In some examples, a rehabilitation plan data structure can be an XML document, a JSON file, a CSV file, an XLS(X) file, or another similar data structure format suited to store organized database information in a searchable and/or reportable format.

FIG. 10A illustrates a sample overview of a rehabilitation plan data structure 1000. As shown in FIG. 10A, the structure 1000 can include various categories of fields such as overall plan fields 1005 and individual exercise data fields 1010. Each of the categories of fields can have various fields nested therein. For example, overall plan fields 1005 can include a plan identifier field 1005a that indicates which plan or plan template is to be used for generating the cardiac rehabilitation plan, an overall number of exercises field 1005b, a plan difficulty level field 1005c, and a plan recommendation field 1005d for the cardiac rehabilitation patient that indicates, for example, an end goal for the patient. Similarly, individual exercise fields 1010 for a particular day can include an exercise identifier field 1010a, a type of exercise field 1010b (e.g., walking, swimming, running, climbing stairs, uphill walking, treadmill activity, elliptical activity, weight-lifting, or other), a prescribed length of exercise field 1010c, a prescribed post-activity RPE field 1010d, a prescribed average heart rate field 1010e, a set of default pre-exercise questions field 1010f, and a set of default post-exercise questions field 1010g. In certain implementations, a particular exercise can include a warm-up period during which the patient is to perform a particular activity for a particular period of time, and/or a cool down period of time. In such an example, the individual exercise fields can include a warm-up indicator field 1010h, a type of warm-up activity field 1010i (e.g., stretching, walking, light run, light weight lifting, or other), and a prescribed length of warm-up field 1010j, a cool down indicator field 1010k, a type of cool down activity field 1010m (e.g., stretching, walking, light run, or other), and a prescribed length of cool down field 1010n.

FIG. 10B illustrates the sample rehabilitation plan data structure 1000 populated with sample data for the various plan identifier fields 1005 and individual exercise fields 1010 as listed above. While only day one is shown in data structure 1000, the individual exercise fields can be repeated for each day of the cardiac rehabilitation plan or for each exercise session in the cardiac rehabilitation plan. For example, the overall number of exercise sessions in the rehabilitative plan can be between about 2 rehabilitative exercises and at least one of 10, 20, 50, 100, and 500 rehabilitative exercises. For instance, the plan may have about 30 exercise sessions spread out over a rehabilitation period of time of around 4 weeks.

It should be noted that, while the example fields as shown in structure 1000 as shown in FIG. 10B are populated with text, this is shown by way of example to convey what information may be contained within the data structure. In an actual implementation, the data structure 1000 would likely be populated with numerical codes indicative of pointers or references to other points of data or variables for access and interpretation by the processor.

Referring back to FIG. 8, upon generation of the cardiac rehabilitation plan, the processor can transmit the cardiac rehabilitation plan to the patient's wearable medical device and cause 806 administration of the cardiac rehabilitation plan by the wearable medical device. For example, in some implementations, the processor can provide an indication separate from transmitting the plan to the wearable medical device to begin executing the rehabilitation plan. In an example, the wearable medical device can be configured to automatically begin executing the plan on receiving an appropriately formatted plan data structure.

The processor can receive 808 patient data from the wearable medical device that has been collected by the wearable medical device prior to, during, and post exercise. The patient data can include ECG information for the patient including, for example, heart rate information such as average heart rate, maximum heart rate, pre-exercise heart rate, post exercise heart rate, resting heart rate, sleeping heart rate, and other similar heart rate information. For example, heart rate information can include metrics such as average, median, mode, or other statistical measure of the heart rate, and/or maximum, minimum, resting, pre-exercise, and post-exercise heart rate values and/or ranges.

Additionally, the ECG information can include measured and/or computed metrics such as, RR interval metrics (such as average, median, mode, or other statistical measure of the RR interval measure, and/or maximum, minimum, resting, pre-exercise, and post-exercise RR interval values and/or ranges), heart rate variability metrics, premature ventricular complex burden or counts, atrial fibrillation (AF) burden metrics (including onset and offset times and associated ECG information), pauses, heart rate turbulence metrics, QRS height, QRS width, changes in a size or shape of morphology of the ECG data, cosine R-T, artificial pacing, QT interval, QT variability, T wave width, T wave alternans, T-wave variability, and ST segment changes.

In an example, non-ECG physiological information can be received and used to (along with ECG information) determine dynamic changes to the plan. For example, as described herein, motion information including step rate can be used to determine patient progress, completion, and incompletion within activity sessions in a plan. The current motion information can be compared to predetermined criteria as described in further detail below to determine dynamic changes to the plan.

In an example, non-ECG physiological information can include respiration information for the patient. For example, one or more vibrational sensors can be used to monitor the patient's respiration (respiration data), pulmonary condition (pulmonary-vibrational data), and cardiac condition (cardio-vibrational data). In monitoring the patient's respiration, the vibrational sensor monitors low frequency vibrations such as chest wall movements of the patient. An example of a vibrational sensor is described in U.S. application Ser. No. 16/355,171, titled "Monitoring Physiological Status Based on Bio-Vibrational and Radio Frequency Data Analysis,"

filed Mar. 15, 2019, now U.S. Pat. No. 10,932,726, the entire contents of which are incorporated herein by reference. In an implementation, the vibrational sensor can include a high-fidelity diaphragm (e.g., a dynamic, electret condenser, ribbon based or a piezoelectric crystal-based diaphragm). Separately, a plurality of motion sensors (e.g., at least two, four, six, or more) can be located around a periphery of the diaphragm. The vibrational signals from the diaphragm and the plurality of motion sensors can be digitized by a series of analog to digital converters (ADC) and processed through a digital signal processing unit. For example, the digital signal processing unit can include a series of digital filters. The signals from one or more of the plurality of motion sensors can be used to monitor low frequency vibrations. For example, such low frequency vibrations can be produced by breathing and/or chest wall movement.

When monitoring higher frequency range vibrational signals (e.g., certain lung vibrations, heart murmurs, etc.) the diaphragm signal can be analyzed as outlined below. To allow for better isolation of the higher frequencies of interest, the signals from the peripheral motion sensors 710 can be summed to determine a common mode signal. The common mode signal can represent lower frequency components that can then be removed from the diaphragm signal.

A table such as Table 7 shown below may be stored in data storage 104. Typical sampling rates in a range of 44.1 kHz to around 60 kHz can be implemented in the ADC to transform the acquired diaphragm vibrational signals into digital vibration signals. In some examples, the ADCs may implement sample sizes in a range from 12-bits to 16-bits, with higher bit lengths to allow for more dynamic range resolution. A variety of digital filters can be run on the input digital signal to remove, for example, interference signals such as 60 Hz components and common mode signals as described above. The digitized vibrational signals can then be analyzed to determine various vibrations based on Table 7. For example, frequency selection filters and circuits can operate in the digital domain to isolate frequency ranges of interest in accordance with the table below. Example digital filtering techniques can include Fast Fourier Transform (FFT), Discrete Cosine Transform (DCT), Infinite impulse response (IIR) filters, among others. A processor can be configured to receive instructions indicating a type of condition to be monitored. Based on the indicated condition, a processor 118 can retrieve a relevant range of frequencies from memory and isolate the relevant signals via a digital filter arrangement for analysis and input.

TABLE 7

| Condition being monitored | Digital filter range |
| --- | --- |
| Breathing/chest wall movement | 0.1-10 Hz |
| Stridor | >500 Hz |
| Wheezing | >100-5000 Hz |
| Rhonchus | 100-200 Hz |
| Pleural friction | <350 Hz |
| S1-S4 heart vibrations | 20-500 Hz |
| Diastolic murmur | 50-150 Hz |
| Aortic regurgitation | 200-600 Hz |

In certain implementations, a vibrational analysis of vibrations detected via a thoracic vibrational sensor as described above can provide information about characteristic vibrational patterns. The vibrational analysis can include monitoring for vibrations ranging from 1/10th to about 1 Hz for monitoring low frequency thoracic cavity movements such as breathing, chest wall movements, and, in some cases, heart wall movements. For example, where the sensor is substantially aligned with an apex of a ventricle of the patient, the sensor implementing vibrational analysis can detect and monitor ventricular wall motion. Similarly, other vibrational patterns can be monitored.

Frequencies involving heart vibrations and murmurs are typically in a range from around 20 to 500 Hz. Low frequency heart vibrations are those where the dominant frequencies are less than around 100 Hz, such as S3, S4, and diastolic murmur of mitral stenosis. Certain murmurs have higher frequency components such as aortic regurgitation, where dominant frequencies are around 400 Hz.

When the processor 118 detects an indication of respiratory disorder or respiratory distress prior to an activity session (e.g., 1 hour before an activity), the processor 118 can cause user interface 108 to indicate that the patient should not perform the upcoming activity. Further, the plan is dynamically adjusted to skip the activity, or otherwise reschedule the activity for a later time. For example, the rescheduled time can be set by a user-configuration parameter. In some implementations, as noted below, the device controller 100 can send a notification to a remote system so an HCP can be informed. In such a scenario, the processor 118 can suspend execution of the rest of the plan until the HCP provides approval. The HCP can provide remote approval regarding the patient's continuation with the plan.

Similarly, when the processor 118 detects an indication of respiratory disorder or respiratory distress duration an activity session, the processor 118 can cause user interface 108 to indicate that the patient should immediately stop performing the activity. Further, in this situation the processor 118 can dynamically adjust the plan to mark the session incomplete, or otherwise reschedule the activity for a later time. In some implementations, the device controller 100 can send a notification to a remote system so an HCP can be informed. In such a scenario, the processor 118 can suspend execution of the rest of the plan until the HCP provides approval. The HCP can provide remote approval regarding the patient's continuation with the plan.

With respect to respiration, the processor 118 can be preset with an expected range of between 10 and 32 breaths per minute for a patient during an activity session (for example, normal breathing range is between 10 to 20 breaths per minute). This respiration range can be user-configurable under direction of an HCP. Accordingly, when the processor 118 detects that the patient's breath rate has transgressed the range (e.g., breathing more rapidly than 32 breaths per minute), the processor 118 can cause the user interface 108 to indicate that the patient should slow down, take a break, or stop performing the activity. The specific instruction to the patient can be pre-set in consultation with the HCP. In an implementation, if the patient's breath rate transgresses the range, the user interface 108 can indicate to the patient to slow down. If the breath rate does not return to within the expected range within a predetermined (in some implementations, user-configurable) time, such as 30 seconds, the device can instruct to the patient to take a break. If after a further predetermined amount of time has passed (in some implementations, also user-configurable) time, such as an additional 30 seconds, the device can instruct the patient to stop the activity. Further, the device dynamically adjusts the plan to mark the session incomplete, or otherwise reschedules the activity for a later time. In some implementations, the device controller 100 can send a notification to a remote system so an HCP can be informed. In such a scenario, the processor 118 can suspend execution of the rest of the plan until the HCP provides approval. The HCP can provide remote approval regarding the patient's continuation with the plan.

In an implementation, a non-ECG physiological parameter can include peak VO2 values (measured in mL/kg/min). Peak VO2 max can be calculated for the patient and used to, for example, describe peak VO2 predetermined criteria to measure a patient's exertional levels during activity sessions. While VO2 max can be used to describe a plateau of the maximum oxygen consumption reached during exercise (e.g., oxygen consumption does not increase beyond a plateau value or range even where external work increases), VO2 max may not be achieved in chronic heart failure patients because they are usually limited by symptoms of fatigue or dyspnea. Peak VO2 (VO2 at peak exercise) may better describe a highest oxygen uptake achieved in chronic heart failure patients. Like maximal work-load and exercise duration, peak VO2 can be dependent upon patient motivation and the patient's perceived symptoms (or HCP's perception of the patient's symptoms). In some cases, exceeding the anaerobic threshold (which can occur at 60-70% of the peak VO2) or a respiratory exchange ratio (the ratio of VCO2 to VO2) exceeding 1.0 at peak exercise can indicate adequate patient effort.

In examples, peak VO2 can be calculated using the formula below, as described in "Simple prediction formula for peak oxygen consumption in patients with chronic heart failure," Journal of Exercise Science & Fitness, Vol. 10, Issue 1, June 2012, Pgs. 23-27.

$$VO2 = 16.7 - 1.3(\text{sex}) - 3.8 \times (\text{New York Heart Association functional class}) + 0.04 \times (\text{peak heart rate}) + 0.92 \times (\text{estimated metabolic equivalents or } METs).$$

The Peak VO2 max for a session can be calculated using the peak heart rate for the session. A peak VO2 parameter can be user-configurable under supervision of an HCP and can be used to determine adjustments to the plan. For example, if the patient's peak VO2 max indicates that the patient is able to easily perform the "easy" exercises, the plan can dynamically adjust to increase the intensity to the "medium" exercises, or further on to the "hard" exercises.

In implementations, metabolic equivalent of tasks (METs) can be assigned as indicated in the below table. In examples, a MET is used to describe the energy needed to sit quietly. Moderate-intensity activities are those in which the patient is moving fast enough or strenuously enough to burn off three to six times as much energy per minute as they would do when sitting quietly (e.g., exercises that are assigned 3 to 9 METs). Hard activities can be assigned more than 6 METs as shown below.

TABLE 8

| <=3.0 METs | 3.0-6.0 METs | >6.0 METs |
| --- | --- | --- |
| Walking-slowly (4 METs) | Walking-very brisk (4 mph) (6 METs) | Hiking-moderately challenging (9 METs) |
| light work (cooking, washing dishes) (2 METs) | Bicycling-light effort (10-12 mph) (6 METs) | Jogging at 6 mph (9 METs) |
| Fishing-sitting (2 METs) | Moderate aerobic exercise (5 METs) | Weight lifting-moderately challenging (8 METs) |

TABLE 8-continued

| <=3.0 METs | 3.0-6.0 METs | >6.0 METs |
| --- | --- | --- |
| Steady, easy yoga (2 METs) | | Bicycling fast (14-16 mph) (8 METs) |

In one implementation, noninvasive estimates of tissue pH, tissue lactate, or muscle oxygen saturation (SmO2) can be obtained via infrared or near infrared spectrographic methods. For example, such techniques of obtaining such information are described in U.S. Pat. No. 8,818,477, titled "Physical Performance Monitoring and Monitors," and filed Jul. 14, 2008 (the '477 patent), the entire contents of which are incorporated herein by reference. For example, as noted in the '477 patent, such noninvasive methods can estimate anaerobic threshold and/or oxygen consumption rates. In implementations, such devices, systems, and techniques can monitor and measure near-infrared spectra of human tissue via reflectance and/or absorbance measurements to quantitatively determine physiological parameters such as pH, blood hematocrit, and oxygen saturation of the tissues.

From one or more of these parameters, an anaerobic threshold can be determined. Accordingly, using such systems, devices, and methods, anaerobic thresholds can be determined without performing multiple invasive measurements (e.g., serial blood withdrawals), and without interfering with the patient completing a rehabilitation plan. In this manner, oxygen consumption rates can be determined remotely, without the patient needing to make clinical visits, without the aid of a metabolic cart, and/or sophisticated gas analysis equipment and trained operators. An anaerobic threshold can be described as a rate of oxygen consumption (or other quantity related to exercise intensity) at which a rate of change of concentration of lactate in a patient's blood increases with incrementally greater work (e.g., incrementally greater physical exertion). For a subject undergoing increasing exercise intensity up to the anaerobic threshold, the patient's blood lactate concentration increases at a rate that is approximately constant in time. Once the patient's anaerobic threshold is reached, the patient's blood lactate concentration begins to rise at a faster rate. Physiologically, the anaerobic threshold corresponds to a point at which a rate of lactate production in the tissue exceeds the rate at which lactate is removed. The anaerobic threshold and hydrogen ion concentration are related in tissue, because production of blood lactate during periods of exercise changes in proportion to the local pH in the tissue. As a result, lactate concentration in a tissue of a patient, which may be used to determine anaerobic threshold, can be monitored by measuring hydrogen ion concentration in the tissue.

For example, an anaerobic threshold can be determined based on a plurality of pH values of the tissue. The plurality of pH values can be obtained by measuring a spectrum of the tissue as obtained via infrared or near-infrared spectroscopy, and determining a pH value from the spectrum. Determining the anaerobic threshold based on the plurality of pH values can include fitting more than one of the plurality of pH values to a mathematical equation as shown below. The anaerobic threshold can then be obtained from the mathematical equation. Accordingly, determining the anaerobic threshold based on the plurality of pH values can include determining a plurality of hydrogen ion concentration values of the tissue from the plurality of pH values, fitting more than one of the plurality of hydrogen ion concentration values to a mathematical equation to determine parameters of the equation, and determining the anaerobic threshold from the mathematical equation. The mathematical equation can be of the form $$y = \begin{Bmatrix} y_1 + s_1(x - x_0), & x < x_0 \\ y_2 + s_2(x - x_0), & x > x_0 \end{Bmatrix}$$

where x is a measure of exercise intensity, x0 is an adjustable parameter that corresponds to the anaerobic threshold, y is the hydrogen ion concentration, and y1, y2, s1, and s2 are adjustable parameters. In examples, a measure of exercise intensity can be a rate of oxygen consumption in the tissue. Determining the anaerobic threshold can include determining a plurality of hydrogen ion concentration values of the tissue from the plurality of pH values, fitting more than one of the plurality of hydrogen ion concentration values to a mathematical equation to determine parameters of the equation, and determining a measure of exercise intensity at which a first derivative of the mathematical equation changes.

In examples, infrared reflectance and/or absorbance measurements are taken in a continuous or periodic manner. For example, such measurements are taken by non-ECG physiological sensors including infrared reflectance sensors and associated sensor circuitry that are disposed on the patient's skin and electrically coupled to a controller (controller 100). From such measurements, various tissue based physiological information can be derived, including tissue pH (from which hydrogen ion concentration is derived), tissue oxygen saturation, blood hematocrit, blood hemoglobin concentration, tissue oxygen partial pressure, and water fraction.

In examples, using such infrared reflectance and/or absorbance measurements, an oxygen consumption rate can be calculated. For example, the oxygen consumption rate can be a rate at which oxygen is removed from oxygenated blood, particularly during periods of physical activity even as oxygen consumption occurs at all times. In particular, during periods of strenuous physical activity, such as when the patient is exerting physical effort, a rate at which oxygen is consumed from blood in muscle tissues can increase relative to the rate of oxygen consumption during periods of physical inactivity. In examples, the oxygen consumption rate in the tissue of a patient can be deemed equivalent to an oxygen uptake rate.

In examples, hydrogen ion concentration for the patient can be determined from pH measurements in the tissue, where the hydrogen ion concentration [H$^+$] is related to pH mathematically as [H$^+$]=$10^{-pH}$. Tissue pH can be determined from near-infrared reflectance and/or absorbance measurements as described in the '477 patent. As a result, the systems, devices, and methods herein can be used to monitor blood lactate concentration in subject tissues from near-infrared measurements performed on the tissues.

Hemoglobin concentration [Hb] can be estimated as one third of the hematocrit level determined from near-infrared spectra. The hematocrit level can be measured from the near-infrared spectra as described in U.S. Pat. No. 6,006, 119, titled "Non-invasive optical measurement of blood hematocrit," filed Feb. 4, 1998 (the '119 patent), the entire contents of which are incorporated herein by reference. For example, as described in the '119 patent, the method for measuring hematocrit level includes irradiating blood with optical radiation having a selected range of optical wavelengths to produce an optical spectrum. The wavelengths in the selected range are affected by a plurality of red blood cell constituents. Hematocrit is determined by processing the optical spectrum with a mathematical model. The model is constructed by relating optical properties of the plurality of red blood cell constituents to known blood hematocrit. As shown in FIG. 1 of the '119 patent, the model is generated by taking optical spectra for a range of wavelengths affected by the plurality of red blood cell constituents from a number of samples at known hematocrit values, and then processing the spectra and the hematocrit values with a multivariate calibration procedure, e.g., a Partial Least Squares (PLS) fitting algorithm. The model is then used to determine the blood hematocrit of a blood sample, e.g., tissue containing blood, by measuring a reflection or transmission spectrum from the blood, and then comparing the spectrum to the model. Alternatively, or in addition, the hemoglobin concentration can be determined directly from near-infrared spectral measurements.

Returning to FIG. 1, the non-ECG physiological information can be derived from non-ECG physiological sensors 123 configured to be attached to the patient as disclosed herein. For example, such sensors and associated circuitry for determining one or both of an anaerobic threshold and oxygen consumption rates can be configured to be attached directly to an arm of a subject via an adjustable (e.g., elastic) strap or adhesive pad. Alternatively, or in addition, the non-ECG physiological sensors and associated circuitry can be attached to a belt or waistband, e.g., of the garment (e.g., garment 1710 of FIG. 17A). In some configurations, the non-ECG sensors can extend from the controller 1720 in FIG. 17A and be configured to be attached to the skin of the patient via an attachment mechanism such as an adhesive pad.

The processor 118 can execute instructions configured to measure both anaerobic threshold and oxygen consumption rates. For example, the controller 100 can transmit, (e.g., wirelessly transmit via network interface 106) the non-ECG physiological data parameters such as anaerobic threshold and oxygen consumption rates, to a remote computing device such as a monitoring server 308 (FIG. 3) for comparison against predetermined criteria and subsequent dynamic adjustment of the plan based on the comparison.

For example, initial or baseline values for an anaerobic threshold and/or oxygen consumption rate can be calculated during a clinical visit by the patient. Once the initial or baseline value(s) are determined, an HCP can set the predetermined criteria using such initial or baseline value(s). For example, if the anaerobic threshold determined from initial or baseline blood lactate measurements, rate of carbon dioxide production (VCO2), or [H+] measurements is around 1.95+/−0.27 L/min, the predetermined criteria for such anaerobic threshold for the patient can be set to around a maximum of 2 L/min.

The received patient data can also include non-ECG physiological information such as motion information collected by one or more motion sensors in the wearable medical device. The motion information can include information related to the patient's pace during the exercise, the duration of the exercise, the start time and/or end time of the exercise, the total distance covered during the exercise, periods of activity outside of the exercise, time spent sleeping or in a prone position, and other similar information that can be determined based upon collected motion information.

As further shown in FIG. 8, the processor can further analyze 810 the patient data to determine how the patient is progressing through the cardiac rehabilitation plan and, if necessary, adjust 812 the cardiac rehabilitation plan. Table 9 as shown below includes various actions and related notes for analyzing patient data (ECG physiological data, non-ECG physiological data, and/or patient feedback) and adjusting a cardiac rehabilitation plan.

heart rate field 1105g, an overall ECG metrics field 1105h, an exercise ECG metric field 1105i, a non-exercise ECG metric field 1105j, an overall RPE field 1105k, and other

TABLE 9

| Action | Notes |
|---|---|
| Non-ECG physiological data: Analyze Session Duration | For example, session duration can be determined based on one or both of output from a multi-axial accelerometer and ECG-based heart rate activity. When the patient activity ceases (e.g., output of accelerometer indicates that the patient is no longer running or otherwise active), the processor records the session duration. The session duration is then compared to the expected duration for the activity. If duration of session achieved, proceed to next action. If not, repeat session. |
| Non-ECG physiological data: Analyze Respiration Rate | If respiration rate exceeds a respiration threshold (e.g., 25 breaths per minute) instruct patient to (in escalating intervals) slow down, take a break, or stop the activity. Patient is asked to repeat session. |
| Non-ECG physiological data: Analyze Step Rate based on multi-axial on-board accelerometer output | If step rate exceeds step rate threshold (e.g., 60 steps per minute), proceed to next action. If not, repeat session. |
| ECG data: Analyze Maximum Heart Rate based on ECG information | Conditionally review heart rate data: If heart rate greater than 120 bpm, repeat session. If heart rate less than 120 bpm but more than 30 bpm above resting heart rate, repeat session If heart rate less than 30 bpm above resting heart rate and duration achieved and step rate achieved, advance to next action. |
| Patient Feedback data: Query Patient for Rating of Perceived Exertion (e.g., via user interface 108) | If patient responds 16 or higher (e.g., on a 6-20 scale), repeat (or don't count) session in the cardiac rehabilitation. If patient responds 15 or less, advance to next session. |

Figure 9B:
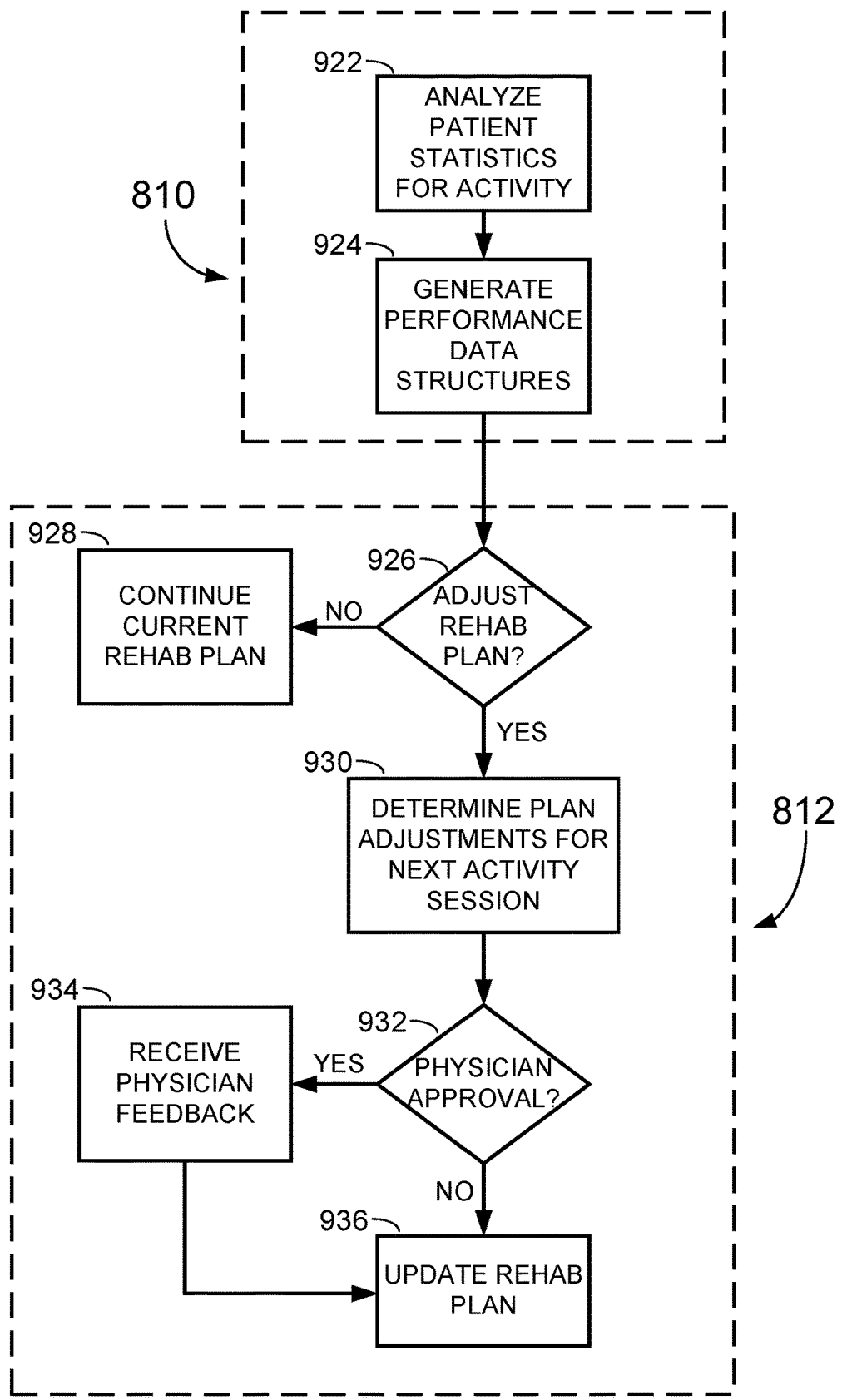
FIG. 9B depicts a sample process flow for analyzing patient data and adjusting a cardiac rehabilitation plan as shown in FIG. 8, in accordance with an example of the present disclosure.

FIG. 9B illustrates a more detailed process flow for analyzing 810 the patient data and adjusting 812 the cardiac rehabilitation plan.

As shown in FIG. 9B, the processor can analyze 922 various patient statistics for an individual exercise session. For example, the patient statistics can include both physiological information such as ECG information as well as non-ECG physiological information such as motion data. Based upon the analysis, the processor can generate 924 one or more exercise performance data structures. In certain implementations, and similar to the rehabilitation plan data structure as described above, an exercise performance data structure can include a database table entry or multiple tables within, for example, an RDBMS database that can be queried using a standard querying language such as SQL. In some examples, a rehabilitation plan data structure can be an XML document, a JSON file, a CSV file, an XLS(X) file, or another similar data structure format suited to store organized database information in a searchable and/or reportable format.

FIG. 11A illustrates a sample overview of an exercise performance data structure 1100. As shown in FIG. 11A, the structure 1100 can include various categories of fields such as overall plan data fields 1105 and individual exercise fields 1110. Each of the categories of fields can have various fields nested therein. For example, overall plan fields 1105 can include a plan identifier field 1105a, a performance evaluation field 1105b, an overall average heart rate field 1105c, a heart rate during exercise field 1105d, a non-exercise heart rate field 1105e, a resting heart rate field 1105f, a sleeping similar fields. Similarly, individual exercise fields 1110 for a particular day can include an exercise identifier field 1110a, a type of exercise field 1110b (e.g., walking, running, weight-lifting, or other), a completion status field 1110c, a duration completed field 1110d, a completed RPE field 1110e, a completed heart rate field 1110f, a warm-up indicator field 1110g, a warm-up duration field 1110h, a cool down indicator field 1110i, a cool down duration field 1110j, a pre-exercise questions and responses field 1110k, a post-exercise questions and responses field 1110m, and other similar exercise-related fields. While only day one is shown in data structure 1100, the individual exercise fields 1110 can be repeated for each day of the cardiac rehabilitation plan.

FIG. 11B illustrates the sample rehabilitation plan data structure 1100 populated with sample data for the various plan identifier fields 1105 and individual exercise fields 1110 as listed above. While only day one is shown in data structure 1100, the individual exercise fields can be repeated for each day of the cardiac rehabilitation plan or for each exercise session in the cardiac rehabilitation plan.

It should be noted that, while the example fields as shown in structure 1100 as shown in FIG. 11B are populated with text, this is shown by way of example to convey what information may be contained within the data structure. In an actual implementation, the data structure 1100 would likely be populated with numerical codes indicative of pointers or references to other points of data or variables for access and interpretation by the processor.

Referring back to FIG. 9B, the processor can compare the performance data structures to predetermined criteria to determine 926 if any adjustments are required for the cardiac rehabilitation plan. The predetermined criteria for determining whether and when the plan is to be adjusted for the next activity session can be based on ECG and non-ECG physiological information. For example, if the patient has completed an exercise session for a particular day and their average heart rate and maximum heart rate are below acceptable thresholds, the processor can continue 928 the current rehabilitation plan without adjustment. Conversely, if the patient has not completed an exercise session for a particular day or one or more measured parameters have exceeded their associated threshold, the processor can determine 926 that the cardiac rehabilitation plan should be adjusted.

Based upon the performance data structures, the processor can determine 930 one or more plan adjustments for the next exercise session in the cardiac rehabilitation plan. For example, the processor can determine 930 that a previous exercise session should be repeated. In some examples, the processor can determine 930 that the patient should complete an exercise session with a reduced number of exertion minutes for the next exercise session. Depending on the type of adjustments made to the cardiac rehabilitation plan, the processor can determine 932 if physician approval is required to implement the adjustment. If the processor does determine 932 that physician approval is required, the processor can transmit the adjusted cardiac rehabilitation plan to the patient's physician or other HCP for approval. Upon receiving 934 physician feedback and approval, the processor can update the rehabilitation plan. Similarly, if the processor determines 932 that physician approval is not necessary, the processor can simply update 936 the rehabilitation plan. It should be noted, however, that the physician approval is shown by way of example only and in some implementations the processor can implement one or more adjustments without determining 932 whether approval is necessary. For example, sample predetermined criteria for determining whether and when the plan is to be adjusted for the next activity session can be based on ECG information, non-ECG physiological information, and patient feedback as follows:

1. Determine next session based on predetermined criteria
    A. Duration assessment (comparing to duration predetermined criteria)
        a. If duration (e.g., D minutes) not achieved—repeat this session
        b. If duration is less than D minutes, but greater than D1 minutes—mark session incomplete and move to next session
    B. Respiration rate assessment (comparing to respiration predetermined criteria)
        a. If average breath rate for activity is less than 20 breaths/minute—repeat this session
        b. If breath rate exceeds 32 breaths/minute during activity—instruct patient to stop activity session.
            i. Postpone or skip session
            ii. Prompt patient to indicate that session is being postponed or skipped
            iii. Prompt patient to contact HCP
            iv. Adjust subsequent exercises in plan to reduce difficulty level
            v. Notify HCP about event, wait until HCP provides approval to continue with plan, or require HCP override to increase difficulty level (see, e.g., Action 932)
        c. If respiratory distress or disorder detected—instruct patient to stop activity session.
            i. Postpone or skip session
            ii. Prompt patient to indicate that session is being postponed or skipped
            iii. Prompt patient to contact HCP
            iv. Adjust subsequent exercises in plan to reduce difficulty level
            v. Notify HCP about event, wait until HCP provides approval to continue with session, or require HCP override to increase difficulty level (see, e.g., Action 932)
    C. Step rate assessment (comparing to step rate predetermined criteria)
        a. If average step rate less than 60 steps/min—repeat this session
    D. Maximum heart rate (HR) (comparing to HR predetermined criteria)
        a. If average HR>120 bpm—repeat this session
        b. Determine resting heart rate pre-exercise (e.g., patient may be asked to sit for 2 min to collect data)
        c. If average HR<120 bpm but more than 30 bpm above resting HR—repeat this session
        d. If average HR<30 bpm above resting HR AND duration achieved AND average step rate >60 steps/min—advance to next session
    E. RPE at end of exercise (comparing to RPE predetermined criteria)
        a. If report 15 or higher on 6-20 scale, move down one session for the next session.
        b. Advance to next session if RPE level 15 or less
    F. If ECG Arrhythmia (e.g., bradycardia onset episode, tachycardia onset episode, AF onset episode, etc.) is detected during session
        a. Immediately stop session
        b. Advise patient to sit down
        c. Prompt patient to indicate that session is being postponed or skipped
        d. Prompt patient to contact HCP
        e. Adjust subsequent exercises in plan to reduce difficulty level
        f. Require HCP override to increase difficulty level (see, e.g., Action 932)
    G. If ECG arrhythmia (e.g., bradycardia onset episode, tachycardia onset episode, AF onset episode, etc.) is detected within 1 hour prior to scheduled session start time (duration can be customized by HCP prescription/request)
        a. Postpone or skip session
        b. Prompt patient to indicate that session is being postponed or skipped
        c. Prompt patient to contact HCP
        d. Adjust subsequent exercises in plan to reduce difficulty level
        e. Notify HCP about event, wait until HCP provides approval to continue with plan, or require HCP override to increase difficulty level (see, e.g., Action 932)

Referring back to FIG. 8, following adjustment of the cardiac rehabilitation plan, the processor can transmit the adjusted cardiac rehabilitation plan to the patient's wearable medical device and cause 814 execution of the adjusted cardiac rehabilitation plan on the device. In certain implementations, the processor can further confirm that the wearable medical device is operating according to the adjusted cardiac rehabilitation plan.

Described below in Tables 12, 13, 14 and 15 are sample cardiac rehabilitation plans. In these examples, it is assumed that the plan is not dynamically adjusted. As such, these plans may be loaded initially into the medical device for the processor to execute and begin collecting exercise performance data.

Shown below in Table 12 is a sample "easy" cardiac rehabilitation plan. In the below plan, it is assumed that the plan is not adjusted. The plan duration or rehabilitation period is 30 days. In this example, the cardiac rehabilitation plan comprises of all walking exercise sessions. As shown, the duration of the initial sessions is about 2 minutes. Further, there are at least 4 walking sessions each day. As the patient progresses through the plan, the duration increases to 3 minutes per session, at around day 27, the patient is required to walk around 10 minutes, and at around day 30, the patient is required to walk around 20 minutes. Also, the number of sessions per day reduces as the duration of each session increases. In between each session, there is a blanking period, e.g., a duration of time when the device will not require the patient to perform an exercise session. As noted, the blanking period initially is set to 2 hours between sessions, and towards the end of the program is around 12 hours between sessions.

TABLE 12

| Day | Session_ID | Total Minutes Walking | Minimum Blanking period between session (hrs) |
|---|---|---|---|
| 1 | 1 | 2 | 2 |
| 1 | 2 | 2 | 2 |
| 1 | 3 | 2 | 2 |
| 1 | 4 | 2 | 2 |
| 2 | 5 | 2 | 2 |
| 2 | 6 | 2 | 2 |
| 2 | 7 | 2 | 2 |
| 2 | 8 | 2 | 2 |
| 3 | 9 | 3 | 2 |
| 3 | 10 | 3 | 2 |
| 3 | 11 | 3 | 2 |
| ... | ... | ... | ... |
| 27 | 74 | 10 | 4 |
| 27 | 75 | 10 | 4 |
| 28 | 76 | 20 | 12 |
| 29 | 77 | 20 | 12 |
| 30 | 78 | 20 | 12 |

Shown below in Table 13 is a sample "medium" cardiac plan. As shown, the duration of the initial sessions is about 3 minutes, longer than the initial duration in the "easy" ~ plan. Further, there are at least 4 walking sessions each day. In one example, there may be more walking sessions per day to reflect the increased difficulty. As the patient progresses through the plan, the duration increases to 5 minutes per session, at around day 27, the patient is required to walk around 15 minutes, and at around day 30, the patient is required to walk around 30 minutes, which are longer sessions than in the "easy" plan. Also, the number of sessions per day reduces as the duration of each session increases. As noted, the blanking period initially is set to 2 hours between sessions, and towards the end of the program is around 12 hours between sessions.

TABLE 13

| Day | Session_ID | Total Minutes Walking | Minimum Blanking period between session (hrs) |
|---|---|---|---|
| 1 | 1 | 3 | 2 |
| 1 | 2 | 3 | 2 |
| 1 | 3 | 3 | 2 |
| 1 | 4 | 3 | 2 |
| 2 | 5 | 3 | 2 |
| 2 | 6 | 3 | 2 |
| 2 | 7 | 3 | 2 |
| 2 | 8 | 3 | 2 |
| 3 | 9 | 5 | 2 |
| 3 | 10 | 5 | 2 |
| 3 | 11 | 5 | 2 |
| ... | ... | ... | ... |
| 27 | 80 | 15 | 4 |
| 27 | 81 | 15 | 4 |
| 28 | 82 | 30 | 12 |
| 29 | 83 | 30 | 12 |
| 30 | 84 | 30 | 12 |

Shown below in Table 14 is a sample "hard" cardiac plan. As shown, the duration of the initial sessions is about 4 minutes, longer than the initial duration in the "easy" and "medium" plans. Further, there are at least 4 walking sessions each day. In an implementation, there may be more walking sessions per day in this plan to reflect the increased difficulty over the "easy" and "medium" plans. As the patient progresses through the plan, the duration increases to 7 minutes per session, at around day 27, the patient is required to walk around 20 minutes, and at around day 30, the patient is required to walk around 40 minutes, which are longer sessions than in the "easy" and "medium" plans. Also, the number of sessions per day reduces as the duration of each session increases. As noted, the blanking period initially is set to 2 hours between sessions, and towards the end of the program is around 12 hours between sessions.

TABLE 14

| Day | Session_ID | Total Minutes Walking | Minimum Blanking period between session (hrs) |
|---|---|---|---|
| 1 | 1 | 4 | 2 |
| 1 | 2 | 4 | 2 |
| 1 | 3 | 4 | 2 |
| 1 | 4 | 4 | 2 |
| 2 | 5 | 4 | 2 |
| 2 | 6 | 4 | 2 |
| 2 | 7 | 4 | 2 |
| 2 | 8 | 4 | 2 |
| 3 | 9 | 7 | 2 |
| 3 | 10 | 7 | 2 |
| 3 | 11 | 7 | 2 |
| ... | ... | ... | ... |
| 27 | 80 | 20 | 4 |
| 27 | 81 | 20 | 4 |
| 28 | 82 | 40 | 12 |
| 29 | 83 | 40 | 12 |
| 30 | 84 | 40 | 12 |

Shown below in Table 15 is another sample cardiac plan. Here, the RPE indicating exercise intensity is designated on the Borg scale of 6 to 20. Further, the notations "VVL" means very, very light, "VL" means very light, "L" means light, and "SH" means somewhat hard.

TABLE 15

| Day | Total Minutes Per Day | Sessions per Day | Total Minutes Per Session | Minutes Warm Up | RPE Warm Up | Intensity Warm Up | Minute Exercise | RPE Exercise | Intensity Exercise |
|---|---|---|---|---|---|---|---|---|---|
| 1 | 12 | 4 | 3 | 0 | | | 3 | 7 | VVL |
| 2 | 16 | 4 | 4 | 0 | | | 4 | 7 | VVL |
| 3 | 20 | 4 | 5 | 0 | | | 5 | 7 | VVL |
| 4 | 24 | 4 | 6 | 0 | | | 6 | 8 | VL |
| 5 | 28 | 4 | 7 | 0 | | | 7 | 8 | VL |
| 6 | 32 | 4 | 8 | 0 | | | 8 | 8 | VL |
| 7 | 36 | 4 | 9 | 0 | | | 9 | 8 | VL |
| 8 | 40 | 4 | 10 | 0 | | | 10 | 9 | L |
| 9 | 33 | 3 | 11 | 0 | | | 11 | 9 | L |
| 10 | 36 | 3 | 12 | 0 | | | 12 | 9 | L |
| ... | ... | ... | ... | ... | ... | ... | ... | ... | ... |
| 19 | 42 | 2 | 21 | 3 | 9 | VL | 15 | 13 | SH |
| 20 | 44 | 2 | 22 | 3 | 9 | VL | 16 | 13 | SH |
| 21 | 46 | 2 | 23 | 3 | 9 | VL | 17 | 13 | SH |
| 22 | 48 | 2 | 24 | 3 | 9 | VL | 18 | 13 | SH |
| 23 | 50 | 2 | 25 | 3 | 9 | VL | 19 | 13 | SH |
| 40 | 42 | 1 | 42 | 5 | 9 | VL | 32 | 13 | SH |
| ... | ... | ... | ... | ... | ... | ... | ... | ... | ... |
| 48 | 50 | 1 | 50 | 5 | 9 | VL | 40 | 13 | SH |
| 49 | 51 | 1 | 51 | 5 | 9 | VL | 41 | 13 | SH |
| 50 | 52 | 1 | 52 | 5 | 9 | VL | 42 | 13 | SH |
| 51 | 53 | 1 | 53 | 5 | 9 | VL | 43 | 13 | SH |
| 52 | 54 | 1 | 54 | 5 | 9 | VL | 44 | 13 | SH |
| 53 | 55 | 1 | 55 | 5 | 9 | VL | 45 | 13 | SH |
| 54 | 56 | 1 | 56 | 5 | 9 | VL | 46 | 13 | SH |
| 55 | 57 | 1 | 57 | 5 | 9 | VL | 47 | 13 | SH |
| 56 | 58 | 1 | 58 | 5 | 9 | VL | 48 | 13 | SH |
| 57 | 59 | 1 | 59 | 5 | 9 | VL | 49 | 13 | SH |
| 58 | 60 | 1 | 60 | 5 | 9 | VL | 50 | 13 | SH |

| Day | RPE Check Timing (e.g., frequency of how often to check RPE, in minutes) | | | Minutes Cool Down | RPE Cool Down | Intensity Cool Down | Heart Rate |
|---|---|---|---|---|---|---|---|
| 1 | | | | 3 | 0 | | HR <30 + resting |
| 2 | | | | 4 | 0 | | HR <30 + resting |
| 3 | | | | 5 | 0 | | HR <30 + resting |
| 4 | | | | 6 | 0 | | HR <30 + resting |
| 5 | | | | 7 | 0 | | HR <30 + resting |
| 6 | | | | 8 | 0 | | HR <30 + resting |
| 7 | | | | 9 | 0 | | HR <30 + resting |
| 8 | 5 | | | 10 | 0 | | HR <30 + resting |
| 9 | 5 | | | 11 | 0 | | HR <30 + resting |
| 10 | 5 | | | 12 | 0 | | HR <30 + resting |
| ... | ... | ... | ... | ... | ... | ... | ... |
| 19 | 5 | 10 | 15 | 18 | 3 | 9 VL | HR <30 + resting |
| 20 | 5 | 10 | 15 | 19 | 3 | 9 VL | HR <30 + resting |
| 21 | 5 | 10 | 15 | 20 | 3 | 9 VL | HR <30 + resting |
| 22 | 5 | 10 | 15 | 21 | 3 | 9 VL | HR <30 + resting |
| 23 | 5 | 10 | 15 | 22 | 3 | 9 VL | HR <30 + resting |
| 40 | | | | 37 | 5 | 9 VL | HR <30 + resting |
| ... | ... | ... | ... | ... | ... | ... | ... |
| 48 | | | | 45 | 5 | 9 VL | HR <30 + resting |
| 49 | | | | 46 | 5 | 9 VL | HR <30 + resting |
| 50 | | | | 47 | 5 | 9 VL | HR <30 + resting |
| 51 | | | | 48 | 5 | 9 VL | HR <30 + resting |
| 52 | | | | 49 | 5 | 9 VL | HR <30 + resting |
| 53 | | | | 50 | 5 | 9 VL | HR <30 + resting |
| 54 | | | | 51 | 5 | 9 VL | HR <30 + resting |
| 55 | | | | 52 | 5 | 9 VL | HR <30 + resting |
| 56 | | | | 53 | 5 | 9 VL | HR <30 + resting |
| 57 | | | | 54 | 5 | 9 VL | HR <30 + resting |
| 58 | | | | 55 | 5 | 9 VL | HR <30 + resting |

Below is sample high-level pseudocode for implementing a dynamic rehabilitation plan, including comparing the ECG and non-ECG information from the patient to predetermined criteria.

I. Patient able to check proposed exercise schedule on monitor—e.g., schedule for today, schedule for this week, and overall plan schedule
II. Confirm data link, e.g., confirm that device has Wi-Fi or Bluetooth connectivity
III. Safe to Start Plan (comparing to predetermined criteria for when device is ready and it is safe for the patient to start the plan)
  1. ECG and/or accelerometer signal quality—if adequate, then proceed to next action
  2. Heart Rate—if average HR>30 bpm and <90 bpm, then proceed to next action
  3. Patient symptom assessment (and comparing to predetermined criteria)
    a. Are you well enough to exercise? Yes or No
    b. What's your shortness of breath level? Scale 1-10 on the monitor
    c. What's your chest pain level? Scale 1-10 on the monitor
    d. What is your fatigue level? Scale 1-10 on the monitor
      i. If "YES" to 'well enough to exercise' AND chest pain and fatigue and shortness of breath score <=2, then proceed to session start
      ii. If "NO" to 'well enough to exercise' then do not start a session
      iii. If chest pain or fatigue or shortness of breath >=3—notify healthcare provider via data link, and do not start next session
  4. Rhythm assessment (e.g., rhythm disorders, or arrhythmias)—analyze ECG rhythm for conditions that may inhibit proper performance of session
IV. Exercise advancement—Launch rehabilitation program and compare ECG and non-ECG information to predetermined criteria
  1. Session #1 will be predetermined from the protocol chosen by HCP
  2. All subsequent sessions will be based on previous session
    a. Adjust duration if needed—follow exercise protocol
    b. Adjust frequency if needed—follow exercise protocol
  3. Determine next session
    a. Duration assessment (comparing to duration predetermined criteria)—if duration not achieved—repeat this session
    b. Step rate assessment (comparing to step rate predetermined criteria)—if average step rate less than 60 steps/min—repeat this session
    c. Maximum heart rate (HR) (comparing to HR predetermined criteria)
      a. If average HR>120 bpm—repeat this session
      b. Determine resting heart rate pre-exercise (e.g., patient may be asked to sit for 2 min to collect data)
      c. If average HR<120 bpm but more than 30 bpm above resting HR—repeat this session
      d. If average HR<30 bpm above resting HR AND duration achieved AND step rate >60 steps/min—advance to next session
    d. RPE at end of exercise (comparing to RPE predetermined criteria)
      a. If report 15 or higher on 6-20 scale, move down one session for the next session.
      b. Advance to next session if RPE level 15 or less
V. Monitor during exercise session (comparing ECG and non-ECG information to predetermined criteria)
  1. Step rate
  2. Heart Rate—terminate session if HR>$HR_x$ bpm ($HR_x$=140 bpm default, can be customized)
  3. Rhythm-sustained VT/VF at or above rate threshold
  4. Monitor for other arrhythmias
  5. Continue to monitor signal quality
VI. Provider Notifications (e.g., via a display on a remote computer)
  1. Symptom report via online portal access—daily, weekly, custom schedule
  2. Compliance and Performance report via online portal access—number of sessions/day, days/week—rolling cumulative data, all data—HR, step rate, minutes, sessions/day
  3. Rehab protocol completion report via online portal access
  4. Push notification if T days with no exercise (T=7 default, can be customized)
VII. Patient Notifications
  1. Time to start
    a. Based on previous exercise session
    b. Pick exercise type
    c. Push button to start
  2. Safe to start—Go/No Go decision "OK to start walking"
  3. Step Rate instructions—calculate and report (e.g., every 10 seconds, 20 seconds, 30 seconds, 1 minute, or custom period)
    a. If<x steps/min—walk faster (x=80 default, can be customized)
    b. If >y steps/min—walk slower (y=100 default, can be customized)
    c. If x to y steps/min—walking at a good pace
  4. Duration instructions
    a. Total time to go at the beginning
    b. A minutes to go (A=2 minutes default, can be customized)
    c. B minute to go (B=1 minute default, can be customized)

As noted above, to track patient progress through a cardiac rehabilitation plan, and to determine whether the patient is adhering to the plan, some examples are configured to provide the patient's physician and/or other HCP with status reports that chart the patient's activities relative to the plan. This feature can be particularly helpful when expanding cardiac rehabilitation to include allowing the patient to complete exercise sessions at a remote location (e.g., at home) while wearing a wearable medical device (e.g., a cardiac monitoring device or a WCD). In this particular outpatient context, a supervising attendant may not be present to witness the patient as they complete exercise sessions. As such, the supervising attendant cannot report patient progress or adherence to the HCP. To solve this problem, the present disclosure provides for a process for monitoring and reporting a patient's progress through and adherence to a cardiac rehabilitation plan as described herein.

Figure 12:
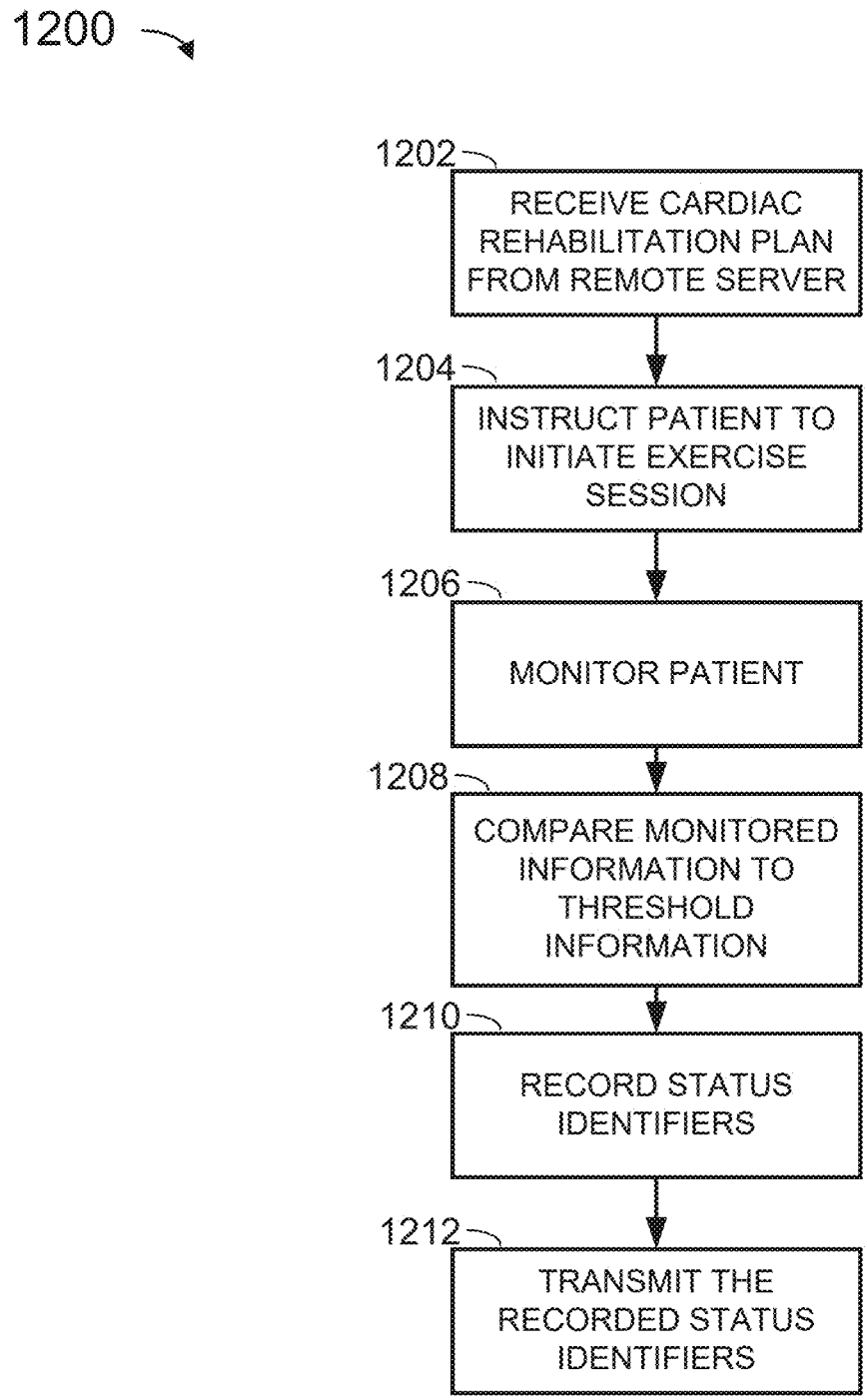
FIG. 12 depicts a sample process flow for monitoring a patient's progress and adherence to a cardiac rehabilitation plan, in accordance with an example of the present disclosure.

For example, FIG. 12 illustrates a sample process 1200 for monitoring a patient's progress and adherence to a cardiac rehabilitation plan. As shown in FIG. 12, a processor such as a processor integrated into a patient's wearable medical device, e.g., wearable medical device 304 as described above, can receive 1202 a cardiac rehabilitation plan from a remote server. In certain implementations, the remote server can generate the cardiac rehabilitation plan as described in various examples discussed above. The processor can instruct 1204 the patient to initiate a rehabilitative exercise session as included in the cardiac rehabilitation plan. For example, the processor can cause a user interface on the wearable medical device to display an indication that an exercise session is scheduled and provide the patient with pre-exercise instructions. The processor can also cause a button or other similar user-selectable area to be displayed on the user interface that, upon activation by the patient, causes the processor to initiate recording of the exercise session. Table 16 as shown below includes a sample set of patient notifications that can be displayed to a patient on, for example, a user interface on the patient's wearable medical device prior to, during, and after an exercise session.

TABLE 16

| Action | Notes |
| --- | --- |
| Display Time to Start | Can be based upon previous exercise sessions and/or cardiac rehabilitation schedule<br>Can prompt for exercise type<br>Can prompt patient to signal start of session |
| Display Safe to Start | Can provide a notification if patient should not initiate the session |
| Display Step Rate Data | Can calculate every 30 seconds, 45 seconds, 1 minute, or other user-configurable period, and display<br>"Walk Faster" if average steps per minute over last period are less than 80 steps per minute<br>"Walk Slower" if average steps per minute are greater than 100 steps per minute<br>"Good Pace" if average steps per minute between 80 and 100 |
| Display ECG Data | Can calculate every 30 seconds, 45 seconds, 1 minute, or other user-configurable period, and display<br>"Work harder" if average heart rate over last period is less than 75 beats per minute<br>"Slow down" if average heart rate over last period is greater than 130 beats per minute<br>"Good Pace" if average heart rate is between 75 and 130 beats per minute<br>"Stop Immediately and Rest" if average heart rate over last period is greater than 145 beats per minute<br>"Stop Immediately and Rest" if predetermined arrhythmia condition determined; follow up notification to call HCP |
| Display Duration Information | Total time at beginning<br>Running clock counting down to completion<br>Milestone displays<br>2 minutes remaining<br>1 minute remaining |
| Display Completion Information | Provide patient with summary data from session<br>Heart rate information<br>Average heart rate<br>Maximum heart<br>Step rate information<br>Average step rate<br>Cardiac Rehabilitation Plan information<br>Proceeding to next session<br>Skipping this session<br>Reason for skipping<br>Repeating this session<br>Reason for repeating |

FIG. 14A illustrates one example of a user interface screen 1400 configured to provide a patient with information regarding a future exercise session. As shown, the user interface screen 1400 includes an exercise type control 1402, a target duration control 1404, a target pace control 1406, a scheduled start time control 1408, a safe to start control 1410, a pre-session instructions control 1412, a start control 1414, and a cancel control 1416.

In some examples, the processor is configured to display a type of exercise to be performed during the future exercise session via the exercise type control 1402. In the example illustrated in FIG. 14A, the type of exercise is walking. The processor can be configured to display additional characteristics of the future exercise session (e.g., target duration, target pace, scheduled start time, whether the patient can safely start the future exercise session, and pre-session instructions) via an analogously named control (e.g. the target duration control 1404, the target pace control 1406, the scheduled start time control 1408, the safe to start control 1410, the pre-session instructions control 1412). In the example illustrated in FIG. 14A, the target duration is 10 minutes, the target pace is 60 steps per minute, the scheduled start time is 2:00 p.m., the processor calculates that it is safe for the patient to start the future exercise session, and the pre-session instructions include an instruction for the patient to stretch and secure a WCD to their person. It should be understood that examples of the user interface screen 1400 are not limited to the particular values illustrated in FIG. 14A. For instance, other exercises (e.g., running, bicycling, swimming, etc.) may be displayed by the processor via the exercise type control 1402. Similarly, the other user interface controls 1404-1412 can display other values of the characteristics of an exercise session as described herein. To determine whether an exercise session is safe to start, the processor can be configured to execute a process that assesses, among other parameters, the patient's condition. One example of such a process is described further below with reference to FIG. 13B.

As shown in FIG. 14A, the processor can be configured to initiate recording of the exercise session in response to receiving a selection of the start control 1414. The processor can also be configured to cancel the future exercise session in response to receiving a selection of the cancel control 1416.

Figure 13A:
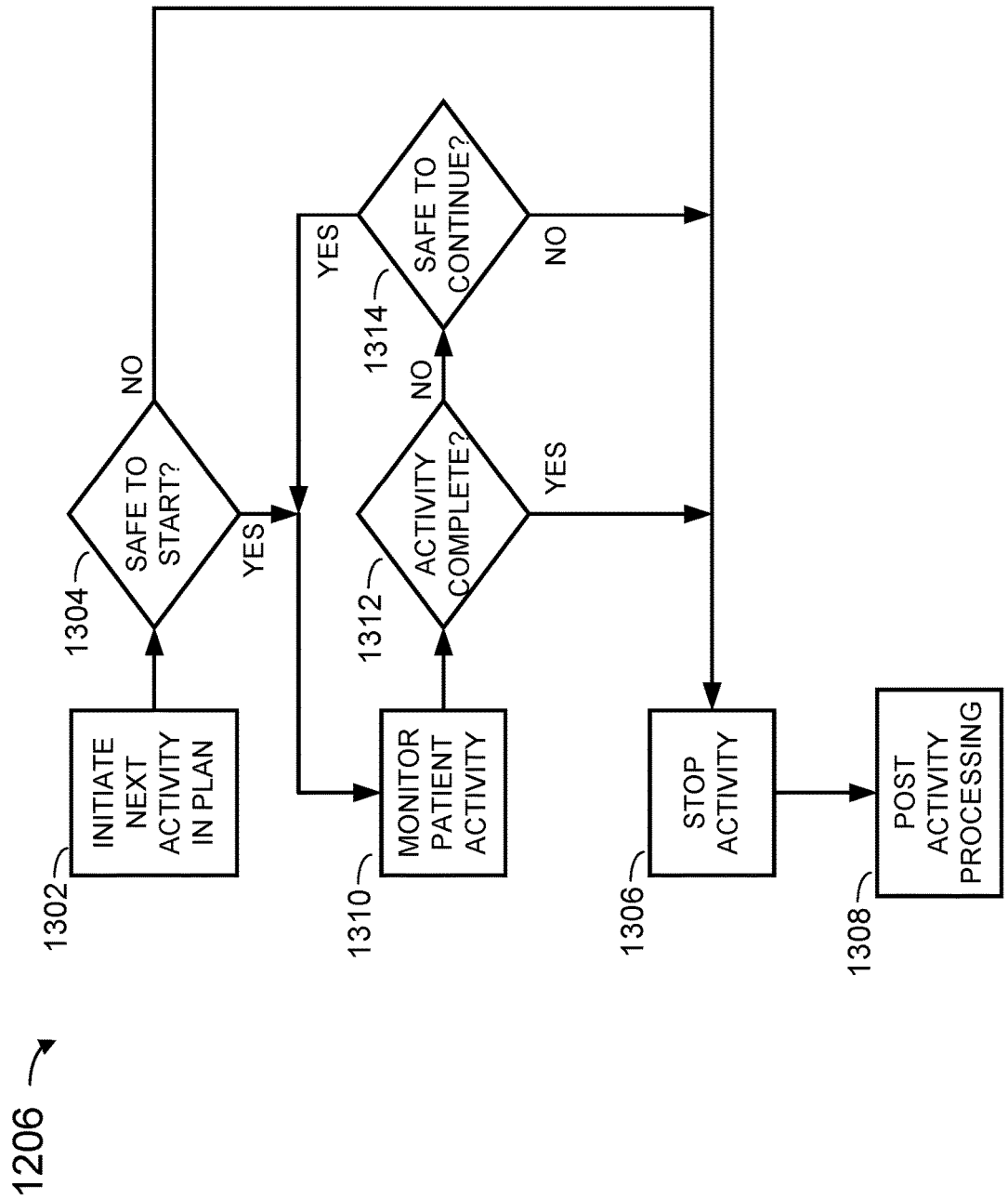
FIG. 13A depicts a sample process flow for initiating exercise and monitoring a patient as shown in FIG. 12, in accordance with an example of the present disclosure.

As further shown in FIG. 12, the processor can initiate 1206 the exercise and monitor the patient during the exercise. FIG. 13A illustrates a more detailed process flow for initiating 1206 the exercise and monitoring the patient during the exercise. For example, as shown in FIG. 13A, the processor can first initiate 1302 the next exercise session in the cardiac rehabilitation plan. The processor can further determine 1304 if it is safe to start the exercise session. For example, Table 17 as shown below includes various actions and related notes for determining 1304 if it is safe to start an exercise session.

TABLE 17

| Action | Notes |
| --- | --- |
| Determine Device Signal Quality | If signal quality is adequate, proceed to next action |
| Determine Initial Heart Rate | If less than 90 bpm, proceed to next action |
| Assess Patient Symptoms (e.g., via a patient user interface 1420 of FIG. 14B disposed on the externally-worn device) | Analyze Results:<br>If not feeling well, do not start a session<br>If feeling well and shortness of |

TABLE 17-continued

| Action | Notes |
|---|---|
| Ask if feeling well enough to exercise<br>Assess shortness of breath (e.g., 0-10 scale)<br>Assess chest pain (e.g., 0-10 scale)<br>Assess fatigue (e.g., 0-10 scale) | breath, chest pain and fatigue are acceptable levels (e.g., 3 or less), start session<br>If shortness of breath or chest pain or fatigue is an unacceptable level (e.g., above 3), do not start a session<br>Notify healthcare provider |

FIG. 14B illustrates one example of a user interface screen 1420 configured to provide a patient with a pre-exercise questionnaire to collect information helpful in determining whether it is safe for a patient to proceed with an exercise session. As shown, the user interface screen 1420 includes a wellness assessment control 1422, a shortness of breath control 1424, a chest pain control 1426, a fatigue control 1428, a submit control 1430, and a cancel control 1432.

In some examples, the processor is configured to prompt the patient to select an indication of whether the patient feels well enough to exercise via the wellness assessment control 1422. In the example illustrated in FIG. 14B, the selected indication is yes. The processor can be configured to prompt the patient to select additional indications of her current condition (e.g., shortness of breath, chest pain, fatigue) via an analogously named control (e.g. the shortness of breath control 1424, the chest pain control 1426, and the fatigue control 1428). In the example illustrated in FIG. 14B, the patient indicates a shortness of breath value of 2 on a scale of 0-10, indicates a chest pain value of 0 on a scale of 0-10, and a fatigue value of 1 on a scale of 0-10. It should be understood that examples of the user interface screen 1420 are not limited to the particular values illustrated in FIG. 14B. For instance, other scales can be used to report similar patient conditions and other patient conditions can be used to determine whether it is safe for a patient to perform a particular exercise session.

As shown in FIG. 14B, the processor can be configured to store, in memory, the patient's answers to the pre-exercise questionnaire in response to receiving a selection of the submit control 1430. The processor can also be configured to cancel the questionnaire in response to receiving a selection of the cancel control 1432.

Figure 13B:
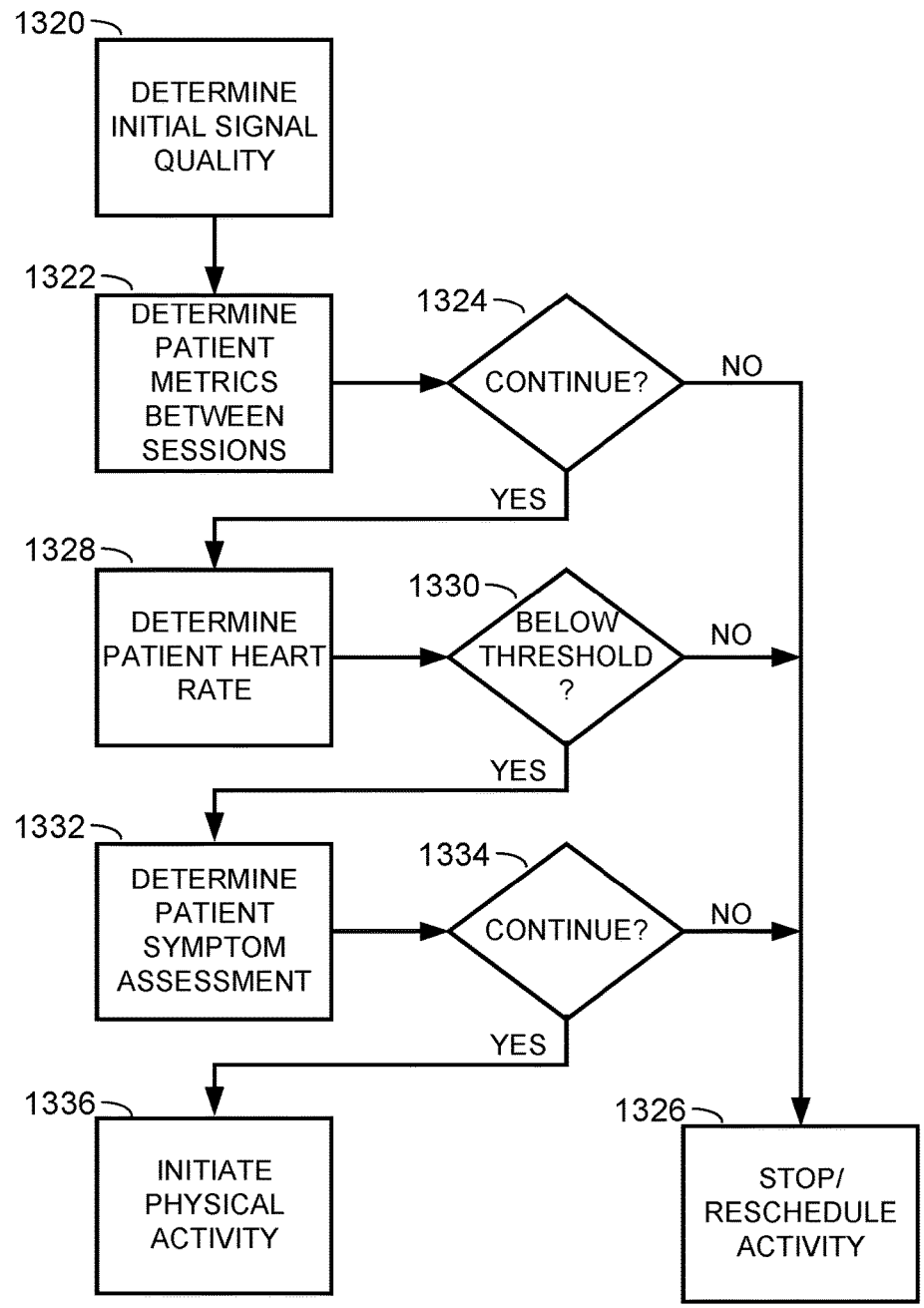
FIG. 13B depicts a sample process flow for initiating a next activity in a cardiac rehabilitation plan as shown in FIG. 13A, in accordance with an example of the present disclosure.

FIG. 13B illustrates a more detailed view of initiating 1302 the next exercise session in the cardiac rehabilitation plan and determining 1304 if it is safe to start the exercise session. For example, as shown in FIG. 13B, the processor can determine 1320 if an initial signal quality from the patient's wearable medical device is acceptable. The processor can also determine 1322 patient metrics such as ECG metrics collected between rehabilitation exercise sessions. The processor can then determine 1324 if the patient can continue with the exercise session. For example, if the patient has been experiencing a higher than usual resting heart rate between exercise sessions, the processor may determine 1324 that the patient should not continue with the exercise session and stop and/or reschedule 1326 the exercise session. Conversely, if the processor does determine 1324 that the patient has not experienced anything between exercise sessions that would cause the processor to stop the current exercise session, the processor can determine 1328 the patient's current heart rate and determine 1330 if the patient's current heart rate is below the threshold for starting an exercise session. For example, the patient heart rate threshold for starting an activity may be the current patient's heart rate within 15% of the patient's resting heart rate. If the processor determines 1330 that the patient's current heart rate is not below the threshold, the processor can stop and/or reschedule 1326 the activity. If the processor does determine 1330 that the patient's current heart rate is below the threshold, the processor can determine 1332 current patient symptoms. For example, as shown in Table 17, the processor can determine 1332 if the patient is experiencing shortness of breath, chest pains, and/or fatigue. Based upon the patient's symptoms, the processor can determine 1334 if it is safe for the patient to continue. If the processor determines 1334 it is safe to continue, the processor can initiate 1336 the physical activity. If the processor determines 1334 it is not safe, the processor can stop and/or reschedule 1326 the activity.

Referring back to FIG. 13A, if the processor determines 1304 that it is not safe to start the activity, the processor can stop 1306 the exercise session and perform 1308 and post-activity processing such as recording why the activity was stopped. Conversely, if the processor does determine 1304 that it is safe to start, the processor can monitor 1310 the patient's activity. Table 18 as shown below includes various actions and notes for monitoring 1310 the patient's activity.

TABLE 18

| Action | Notes |
|---|---|
| Monitor Step Rate | Collect Step Rate Data<br>Average step rate (steps per minute)<br>Maximum step rate<br>Minimum step rate |
| Monitor Heart Rate | Collect Heart Rate Data<br>Average heart rate<br>Maximum heart rate<br>Average heart rate above resting heart rate<br>Maximum heart rate above resting heart rate |
| Monitor Heart Rhythm | Monitor ECG data for sustained VT/VF at or above heart rate threshold (e.g., 120 bpm) |
| Monitor Signal Quality | Monitor signal quality from wearable medical device for possible noise and/or motion artifacts that may impact other collected data |

FIG. 14C illustrates one example of a user interface screen 1440 configured to provide a patient with information regarding an exercise session being performed currently. As shown, the user interface screen 1440 includes the target duration control 1404, a target pace control 1406, an actual pace control 1442, a remaining duration control 1444, a last milestone control 1446, and an end control 1448.

The target duration control 1404 and the target pace control 1406 are described above with reference to FIG. 14A. As such, the description of these user interface controls will not be repeated here, but each is configured to function within the user interface screen 1440 as it is configured to function in the user interface screen 1400.

In some examples, the processor is configured to display an actual pace of the patient during the current exercise session via the actual pace control 1442. In the example illustrated in FIG. 14C, the actual pace is 40 steps per minute. The processor can be configured to display additional characteristics of the current exercise session (e.g., remaining duration and last milestone achieved) via an analogously named control (e.g. the remaining duration control 1444, the last milestone control 1446). In the example illustrated in FIG. 14C, the remaining duration is 5 minutes and 30 seconds and the last milestone achieved was the 6 minutes to go mark. It should be understood that examples of the user interface screen 1440 are not limited to the particular values illustrated in FIG. 14C. For instance, the processor can be configured to display other types of pace (e.g., average miles per hour, strokes per minute, etc.) depending on the type of exercise being performed within the exercise session. Similarly, the processor can be configured to base milestones on threshold values of other exercise session metrics (e.g., number of minutes achieved, actual pace maintained, distance traversed, etc.).

As shown in FIG. 14C, the processor can be configured to end recording of the current exercise session in response to receiving a selection of the end control 1448. In some examples, the processor omits the end control 1448 and automatically ends the exercise session in response to the actual pace falling below a threshold value for a predetermined period of time (e.g., less than 2 steps a minute for a duration of 30 seconds) or in response to expiration of the remaining duration, whichever occurs first.

During the activity, the processor can determine 1312 if the activity is complete. If the activity is complete, the processor can stop 1306 the activity and perform 1308 any post activity processing. If, conversely, the processor determines 1312 that the activity is not complete, the processor can determine 1314 if it is safe for the patient to continue. For example, the processor can determine if the patient's heart rate is at an acceptable level. If the processor determines 1314 that it is not safe to continue, the processor can stop 1306 the activity and perform 1308 any post-activity processing. If the processor does determine 1314 that it is safe for the patient to continue, the processor can continue to monitor 1310 the patient activity.

Referring back to FIG. 12, the processor can compare 1208 the monitored patient information (e.g., heart rate and motion information) to threshold information for the activity. Based upon the comparison, the processor can record 1210 one or more status identifiers to the exercise session. For example, the status identifiers can provide an indication of whether the patient completed the exercise session as well as provide an indication as to how well the patient did during the exercise session. Table 19 below provides a sample set of status identifiers and the required criteria for receiving the status identifier for an exercise session that included walking for a specific duration at a set pace:

TABLE 19

| Status Identifier | Required Criteria |
| --- | --- |
| Completed Exercise Session | Satisfied the exercise session duration, any potential required distance traveled, and required pace of movement |
| Non-Completed Exercise Session | Did not satisfy at least one of the exercise session duration, any potential required distance traveled, and required pace of movement |
| Over-Performance of Exercise Session | Exceeded at least one of the potential required distance traveled or required pace of movement by 10% |
| Under-Performance of Exercise Session | Satisfied the duration but under-performed at least one of the potential required distance traveled or required pace of movement by 10% |
| Non-Performance of Exercise Session | Did not attempt exercise session |

Figure 15:
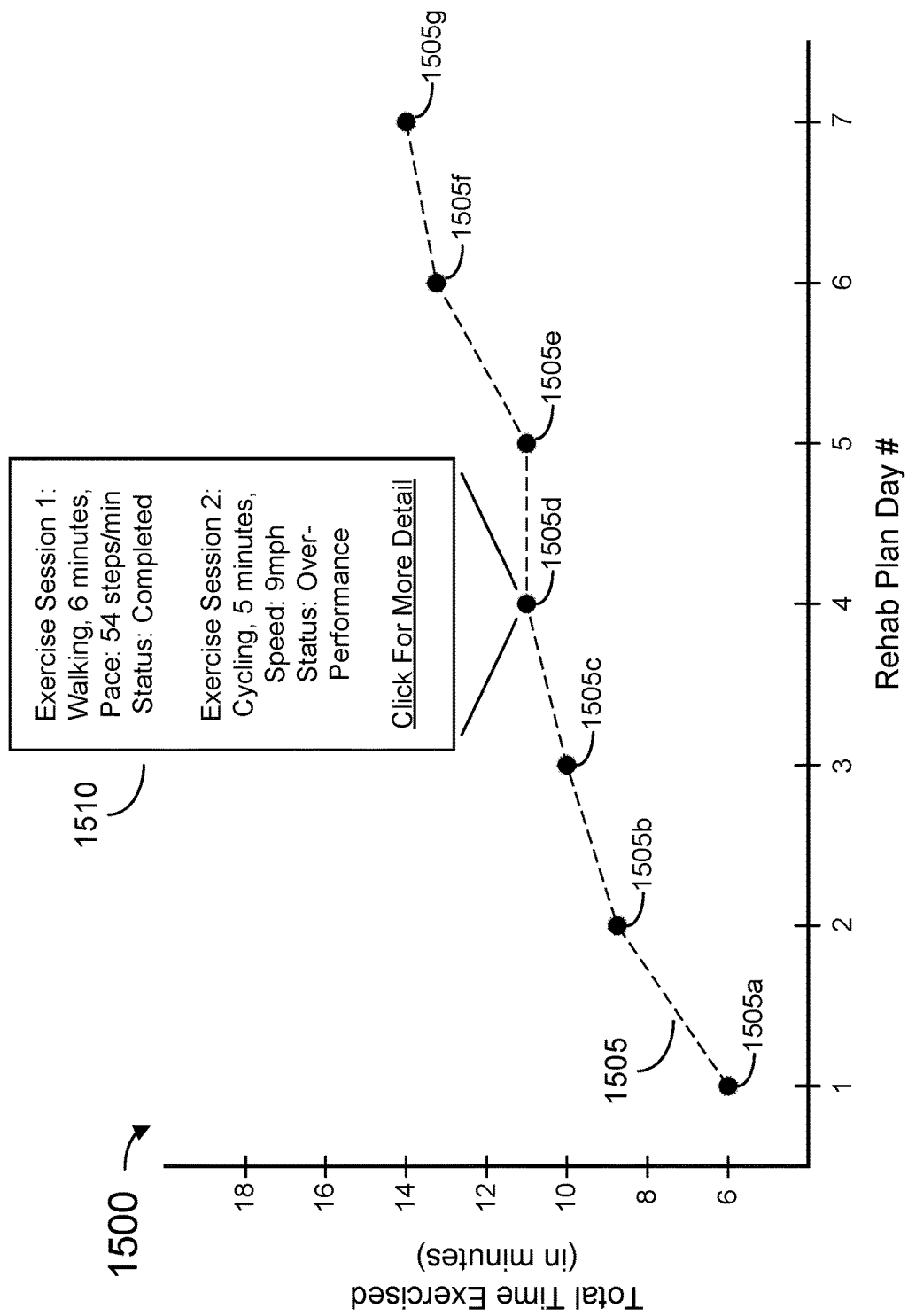
FIG. 15 depicts a graph showing patient progression and adherence to a cardiac rehabilitation plan, in accordance with an example of the present disclosure.

The processor can transmit 1212 the recorded status identifiers to the remote server for processing. For example, the remote server can construct or update patient report that includes adherence and/or performance information for a patient as the patient progresses through a cardiac rehabilitation plan. For example, FIG. 15 illustrates a sample graph 1500 that can be generated by the remote server based upon the status identifiers recorded by and provided from the wearable medical device. As shown in FIG. 15, the graph 1500 can include cardiac rehabilitation plan days on the X-axis and total time exerted on the Y-axis. The graph 1500 can further include line 1505 that passes through a set of user-selectable points 1505a-1505g. Upon receiving an indication that, for example, a patient's physician has selected one of the user-selectable points 1505a-1505g, the processor can determine and display information related to that day and one or more exercise sessions associated with that day. For example, as shown in FIG. 15, user-selectable point 1505d has been selected, the point associated with day 4 of the cardiac rehabilitation plan. As shown in graph 1500, a box 1510 can be displayed including more detailed information about the exercise sessions that the patient completed on day 4. For example, the information 1510 includes activity type information, duration information, pace/speed information, and status information for two exercise sessions that the patient completed on day 4. The information box 1510 can also include a link or other user-selectable control for obtaining additional detailed information related to the exercise sessions such as heart rate information and other information collected and stored in, for example, a data structure such as exercise performance data structure 1100 as shown in FIGS. 11A and 11B and described above. By reviewing graph 1500, and accessing additional information linked to or otherwise associated with the graph, a patient's physician or other HCP can quickly determine how the patient is progressing through the cardiac rehabilitation plan and if the patient is adhering to the plan.

FIG. 14D illustrates one example of a user interface screen 1460 configured to provide a patient with post exercise session information as well as one or more questions regarding an exercise session previously performed. As shown, the user interface screen 1460 includes an average heart rate control 1462, a maximum heart rate control 1464, an average pace control 1466, a performance control 1468, and a perceived exertion control 1470.

In some examples, the processor is configured to display an average heart rate of the patient during the previous exercise session via the average heart rate control 1462. In the example illustrated in FIG. 14D, the average heart rate is 100 beats per minute. The processor can be configured to display additional characteristics of the previous exercise session (e.g., maximum heart rate, average pace, and performance) via an analogously named control (e.g. the maximum heart rate control 1464, the average pace control 1466, and the performance control 1468). In the example illustrated in FIG. 14D, the maximum heart rate is 120 beats per minute, the average pace is 60 steps per minute, and the performance of the patient is insufficient to advance in the plan due to an insufficient average pace. The processor can be configured to prompt the patient to select at least additional indication of their current post-session condition (e.g., provide or rate their exertion during the last exercise session, thereby providing RPE as described herein) via an analogously named control (e.g. the perceived exertion control 1470). In the example illustrated in FIG. 14D, the patient indicates an exertion rating of 14 on an RPE scale of 6-20.

It should be understood that examples of the user interface screen 1460 are not limited to the particular values illustrated in FIG. 14D. For instance, the processor can be configured to display other physiological parameters recorded during the previous exercise session and use those parameters in determining patient performance.

As shown in FIG. 14D, the processor can be configured to close the user interface screen 1460 in response to receiving a selection of the OK control 1472.

Figure 16:
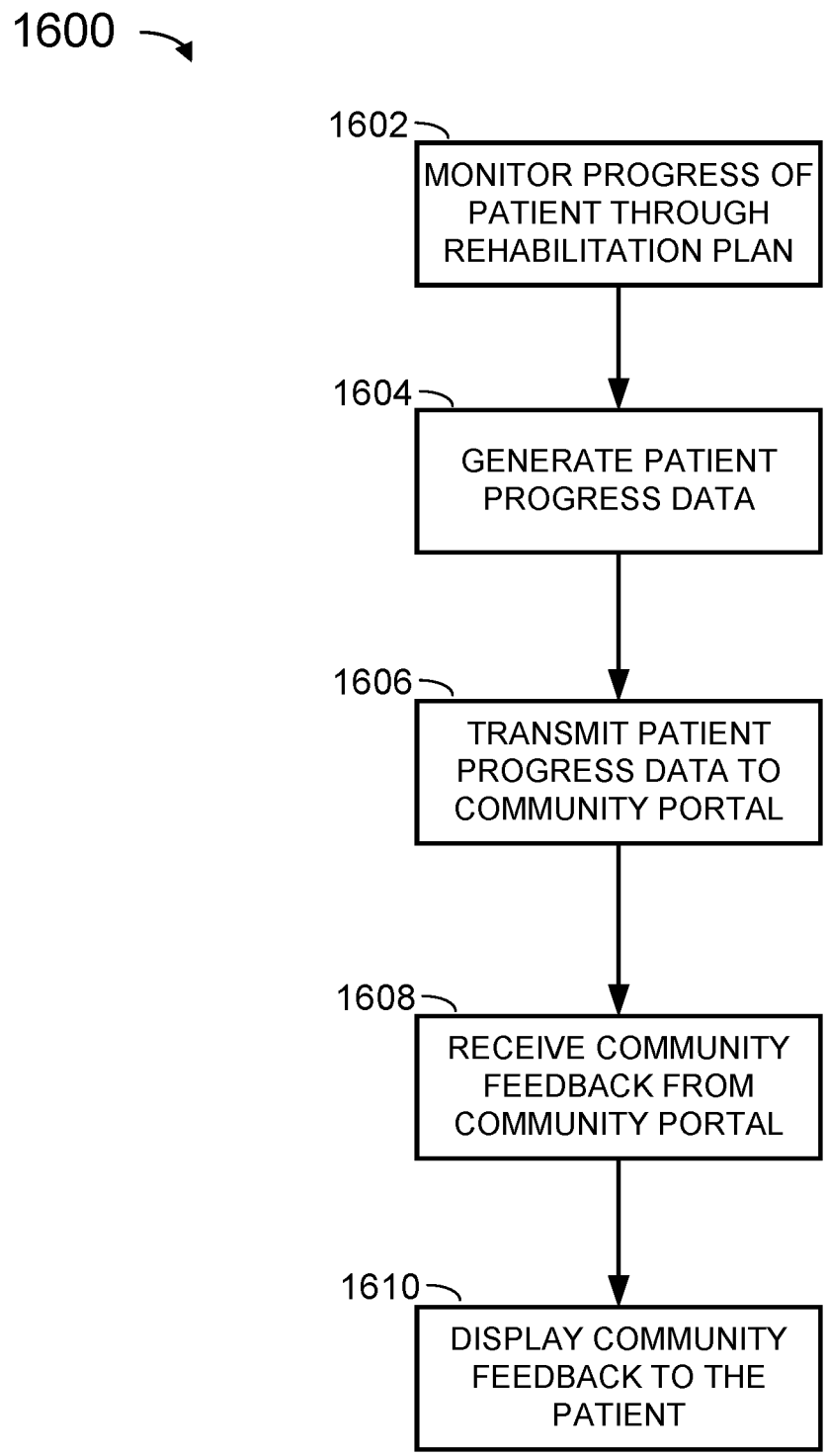
FIG. 16 depicts a sample process flow showing a patient's participation in a community portal, in accordance with an example of the present disclosure.

Additional implementations or examples can further include a community-based portal or other similar social aspect to the provide added motivation for a patient that is completing a cardiac rehabilitation program. For example, FIG. 16 illustrates a sample process 1600 for incorporating aspects of a community-based portal for a patient that has been prescribed outpatient cardiac rehabilitation program. As shown in FIG. 16, a processor such as a processor integrated into a remote server can monitor 1602 the progress of a patient through a cardiac rehabilitation plan. The processor can generate 1604 patient progress data including, for example, updates about how the patient is progressing through the cardiac rehabilitation plan, if the patient has received any positive status identifiers as described above (e.g., over-performance of an exercise session), and other similar information related to the patient's progression through the cardiac rehabilitation plan.

The processor can transmit 1606 the patient progress data to a community portal. For example, the community portal can include other patients who are progressing through cardiac rehabilitation programs, healthcare providers, friends and family of the patient, and other similar supportive acquaintances in the patient's life. Those members of the community portal can provide feedback such as positive reinforcement comments for the patient. The processor can be configured to receive 1608 the community feedback from the community portal to cause the community feedback to be displayed 1610 to the patient.

In some examples, the processor can further generate a patient score based upon the patient's progress information, transmit the patient score to the community portal, and receive patient ranking information from the community portal. The processor can then cause the patient score and ranking to be displayed to the patient.

In an example, a wearable medical device as described herein can be configured to provide a patient with access to a directed rehabilitation plan specifically designed for the patient. The device can include a monitor and an electrode belt as described herein. The device can be configured to analyze a 2-lead ECG from the electrode belt to determine cardiac information for the patient. The device can also analyze accelerometer or other similar motion sensor signals from the electrode belt to determine patient movement information such as step count.

The directed rehabilitation plan can include a patient symptom assessment, a resting heart rate monitoring period, an activity session, and a post-activity symptom assessment. Prior to the activity session, the device can assess adequate signal quality (e.g., ECG signal and quality and/or accelerometer signal quality) before instructing the patient to proceed to the activity session. For example, the accelerometer signal quality can be assessed during a two minute sitting period. During this period, the accelerometer signal can be determined to be adequate if there are less than or equal to five total steps measured during the two minutes of rest. The device can assess ECG signal quality by assessing the overall quality of the received signals continuously throughout device wear. For example, the device can monitor noise in the received ECG signals and, if the noise does not exceed a certain amplitude or frequency in the ECG signals, the ECG signals can be determined to be adequate.

Prior to starting the activity session, the device can also perform a patient symptom assessment. For example, the device can display or otherwise present the patient with one or more questions as described herein and analyze the patient's responses. For example, the patient can be asked "Are you well enough to exercise today?" If the patient answers "No," the device can end the session. If the patient answers "Yes," the device can query the patient for additional information such as a rating of current chest pain on a scale of 1-10, a rating of current shortness of breath on a scale of 1-10, and a rating of current fatigue on a scale of 1-10. If, for example, the ratings for each of the additional queries are less than or equal to two, the device can continue with the session.

In some examples, the device can instruct the patient to sit for two minutes. During this time, the device can analyze the accelerometer signal as described above. Additionally, the device can monitor the patient's heart rate. If the patient's heart rate remains between 30 bpm and 90 bpm during the two minutes of rest, the device can continue the session. However, if the patient's heart rate is below 30 bpm or above 90 bpm during the two minutes of rest, the device can end the session.

If the session is continued, the device can access a particular activity as described herein for the patient to complete. For example, the device can access a medium walking program as described herein. The device can instruct the patient to begin walking. During the activity, the device can continuously monitor the patient's ECG signals and accelerometer signals. The device can regularly calculate the patient's step rate. For example, the device can calculate the patient's step rate every 15 seconds. In some examples, the device can calculate the patient's step rate at least one of every 10 seconds, every 20 seconds, every 30 seconds, and every minute.

Based upon the calculated step rate, the device can instruct the patient to adjust her speed. For example, if the step rate is less than 80 steps per minute, the device can instruct the patient to increase her speed. Conversely, if the step rate is greater than 120 steps per minute, the device can instruct the patient to decrease her speed. As described herein, various thresholds such as the patient's target step rate can be initially set by the patient's physician and adjusted by, for example, the physician or automatically by the device throughout the rehabilitation process. It should also be noted that a target step rate of between 80 and 120 steps per minute is provided by way of example only. In certain implementations, a patient's target step rate can be between about 60 and 100 steps per minute, between about 75 and 125 steps per minute, and between other similar step ranges.

In addition to monitoring the patient's step rate, the device can also monitor the patient's heart rate. For example, if the patient's heart rate exceeds 130 bpm, the device can signal to the patient that they should immediately stop the activity session. Depending upon the patient, the heart rate threshold for ending an activity session can vary accordingly. For example, the heart rate threshold for ending an activity session can be about 120 bpm, 125 bpm, 130 bpm, 135 bpm, 140 bpm, and other similar heart rate measurements.

The device can monitor the total time elapsed during the activity session as well. In certain implementations, the device can display or otherwise provide a notice to the patient of time elapsed and/or total time remaining in the activity session. Once the total time has elapsed, the device can instruct the patient to stop the activity.

Once the activity has stopped, either due to time elapsing or the patient's heart rate exceeding a particular threshold as described above, the device can perform a post-activity symptom assessment. For example, the device can prompt the patient for ratings of fatigue, chest pain, and shortness of breath on a scale of 1-10.

Based upon the patient's performance in the activity session, as well as the patient feedback in the post-activity symptom assessment, the device can determine if the patient should proceed to the next session in the rehabilitation plan, repeat the current session in the plan, or take some other action such as repeat a previous session or contact the patient's physician. For example, the device can analyze whether the total duration of the current session was achieved, if the patient maintained a target activity goal (e.g., step rate as described above), maintained an acceptable heart rate, and providing post-activity symptom ratings less than, for example, seven on a 1-10 scale.

In some examples, as the patient progresses through the rehabilitation plan, the device can provide an indication to the patient about what percentage of overall plan has been completed. Upon completion of the plan, the device can provide an indication to the of the plan completion patient. Additionally or alternatively, the device can, for example, provide indications of any additional activities the patient is instructed to complete upon completion of the overall plan, such as scheduling a visit with their physician and/or returning the device to its manufacturer for servicing.

The teachings of the present disclosure can be generally applied to external medical monitoring and/or treatment devices. Such external medical devices can include, for example, ambulatory medical devices as described herein that are capable of and designed for moving with the patient as the patient goes about his or her daily routine. An example ambulatory medical device can be a wearable medical device such as a WCD, a wearable cardiac monitoring device, an in-hospital device such as an in-hospital wearable defibrillator (HWD), a short-term wearable cardiac monitoring and/or therapeutic device, mobile cardiac event monitoring devices, and other similar wearable medical devices.

The wearable medical device can be capable of continuous use by the patient. In some implementations, the continuous use can be substantially or nearly continuous in nature. That is, the wearable medical device can be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless be considered continuous use. For example, the wearable medical device can be configured to be worn by a patient for as many as 24 hours a day. In some implementations, the patient can remove the wearable medical device for a short portion of the day (e.g., for half an hour to bathe).

In some examples, the wearable medical device can be designed for intermittent use. For example, the wearable medical device can be designed to be worn for half an hour in the morning, half an hour in the afternoon, and half an hour in the evening. During these wear periods, the device can be collecting ECG information for additional analysis as described herein.

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other HCP provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., electrocardiogram (ECG) information, including arrhythmia information, cardio-vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the ambulatory medical devices described herein can be pacing-enabled, e.g., capable of providing therapeutic pacing pulses to the patient. In some examples, the ambulatory medical devices can be configured to monitor for and/or measure ECG metrics including, for example, heart rate (such as average, median, mode, or other statistical measure of the heart rate, and/or maximum, minimum, resting, pre-exercise, and post-exercise heart rate values and/or ranges), heart rate variability metrics, PVC burden or counts, atrial fibrillation burden metrics, pauses, heart rate turbulence, QRS height, QRS width, changes in a size or shape of morphology of the ECG information, cosine R-T, artificial pacing, QT interval, QT variability, T wave width, T wave alternans, T-wave variability, and ST segment changes.

As noted above, FIG. 1 illustrates an example component-level view of a medical device controller 100 included in, for example, a wearable medical device. As further shown in FIG. 1, the therapy delivery circuitry 102 can be coupled to one or more electrodes 120 configured to provide therapy to the patient. For example, the therapy delivery circuitry 102 can include, or be operably connected to, circuitry components that are configured to generate and provide an electrical therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuitry and under control of one or more processors (e.g., processor 118) to provide, for example, at least one therapeutic shock to the patient including one or more pacing or defibrillation therapeutic pulses.

Pacing pulses can be used to treat cardiac arrhythmia conditions such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). In some examples, the capacitors can include a single film or electrolytic capacitor as a series connected device including a bank of the same capacitors. These capacitors can be switched into a series connection during discharge for a defibrillation pulse. For example, a single capacitor of approximately 140 uF or larger, or four capacitors of approximately 650 uF can be used. The capacitors can have a 1600 VDC or higher rating for a single capacitor, or a surge rating between approximately 350 to 500 VDC for paralleled capacitors and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuitry 102 can be configured to perform the switching and pulse delivery operations, e.g., under control of the processor 118. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 104 can include one or more of non-transitory computer-readable media, such as flash memory, solid state memory, magnetic memory, optical memory, cache memory, combinations thereof, and others. The data storage 104 can be configured to store executable instructions and data used for operation of the medical device controller 100. In certain examples, the data storage can include executable instructions that, when executed, are configured to cause the processor 118 to perform one or more operations. In some examples, the data storage 104 can be configured to store information such as ECG data as received from, for example, the sensing electrode interface.

In some examples, the network interface 106 can facilitate the communication of information between the medical device controller 100 and one or more other devices or entities over a communications network. For example, where the medical device controller 100 is included in an ambulatory medical device, the network interface 106 can be configured to communicate with a remote computing device such as a remote server or other similar computing device. The network interface 106 can include communications circuitry for transmitting data in accordance with a Bluetooth® wireless standard for exchanging such data over short distances to an intermediary device. For example, such an intermediary device can be configured as a base station, a "hotspot" device, a smartphone, a tablet, a portable computing device, and/or other devices in proximity of the wearable medical device including the medical device controller 100. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain examples, the user interface 108 can include one or more physical interface devices such as input devices, output devices, and combination input/output devices and a software stack configured to drive operation of the devices. These user interface elements can render visual, audio, and/or tactile content. Thus, the user interface 108 can receive input or provide output, thereby enabling a user to interact with the medical device controller 100.

The medical device controller 100 can also include at least one battery 110 configured to provide power to one or more components integrated in the medical device controller 100. The battery 110 can include a rechargeable multi-cell battery pack. In one example implementation, the battery 110 can include three or more 2200 mAh lithium ion cells that provide electrical power to the other device components within the medical device controller 100. For example, the battery 110 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 100.

The sensor interface 112 can include physiological signal circuitry that is coupled to one or more sensors configured to monitor one or more physiological parameters of the patient. As shown, the sensors can be coupled to the medical device controller 100 via a wired or wireless connection. The sensors can include one or more ECG sensing electrodes 122, and non-ECG physiological sensors 123 such as vibration sensor 124, tissue fluid monitors 126 (e.g., based on ultra-wide band radiofrequency devices), and motion sensors (e.g., accelerometers, gyroscopes, and/or magnetometers). In some implementations, the sensors can include a plurality of conventional ECG sensing electrodes in addition to digital sensing electrodes.

The sensing electrodes 122 can be configured to monitor a patient's ECG information. For example, by design, the digital sensing electrodes 122 can include skin-contacting electrode surfaces that may be deemed polarizable or non-polarizable depending on a variety of factors including the metals and/or coatings used in constructing the electrode surface. All such electrodes can be used with the principles, techniques, devices and systems described herein. For example, the electrode surfaces can be based on stainless steel, noble metals such as platinum, or Ag—AgCl.

In some examples, the electrodes 122 can be used with an electrolytic gel dispersed between the electrode surface and the patient's skin. In certain implementations, the electrodes 122 can be dry electrodes that do not need an electrolytic material. As an example, such a dry electrode can be based on tantalum metal and having a tantalum pentoxide coating as is described above. Such dry electrodes can be more comfortable for long term monitoring applications.

Referring back to FIG. 1, the vibration sensors 124 be configured to detect cardiac or pulmonary vibration information. For example, the vibration sensors 124 can detect a patient's heart valve vibration information. For example, the vibration sensors 124 can be configured to detect cardio-vibrational signal values including any one or all of S1, S2, S3, and S4. From these cardio-vibrational signal values or heart vibration values, certain heart vibration metrics may be calculated, including any one or more of electromechanical activation time (EMAT), average EMAT, percentage of EMAT (% EMAT), systolic dysfunction index (SDI), and left ventricular systolic time (LVST). The vibration sensors 124 can also be configured to detect heart wall motion, for instance, by placement of the sensor in the region of the apical beat. The vibration sensors 124 can include a vibrational sensor configured to detect vibrations from a subject's cardiac and pulmonary system and provide an output signal responsive to the detected vibrations of a targeted organ, for example, being able to detect vibrations generated in the trachea or lungs due to the flow of air during breathing. In certain implementations, additional physiological information can be determined from pulmonary-vibrational signals such as, for example, lung vibration characteristics based on sounds produced within the lungs (e.g., stridor, crackle, etc.). The vibration sensors 124 can also include a multi-channel accelerometer, for example, a three-channel accelerometer configured to sense movement in each of three orthogonal axes such that patient movement/body position can be detected and correlated to detected cardio-vibrations information. The vibration sensors 124 can transmit information descriptive of the cardio-vibrations information to the sensor interface 112 for subsequent analysis.

The tissue fluid monitors 126 can use radio frequency (RF) based techniques to assess fluid levels and accumulation in a patient's body tissue. For example, the tissue fluid monitors 126 can be configured to measure fluid content in the lungs, typically for diagnosis and follow-up of pulmonary edema or lung congestion in heart failure patients. The tissue fluid monitors 126 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 126 can transmit information descriptive of the tissue fluid levels to the sensor interface 112 for subsequent analysis.

In certain implementations, the cardiac event detector 116 can be configured to monitor a patient's ECG signal for an occurrence of a cardiac event such as an arrhythmia or other similar cardiac event. The cardiac event detector can be configured to operate in concert with the processor 118 to execute one or more methods that process received ECG signals from, for example, the sensing electrodes 122 and determine the likelihood that a patient is experiencing a cardiac event. The cardiac event detector 116 can be implemented using hardware or a combination of hardware and software. For instance, in some examples, cardiac event detector 116 can be implemented as a software component that is stored within the data storage 104 and executed by the processor 118. In this example, the instructions included in the cardiac event detector 116 can cause the processor 118 to perform one or more methods for analyzing a received ECG signal to determine whether an adverse cardiac event is occurring. In other examples, the cardiac event detector 116 can be an application-specific integrated circuit (ASIC) that is coupled to the processor 118 and configured to monitor ECG signals for adverse cardiac event occurrences. Thus, examples of the cardiac event detector 116 are not limited to a particular hardware or software implementation.

In some implementations, the processor 118 includes one or more processors (or one or more processor cores) that each are configured to perform a series of instructions that result in manipulated data and/or control the operation of the other components of the medical device controller 100. In some implementations, when executing a specific process (e.g., cardiac monitoring), the processor 118 can be configured to make specific logic-based determinations based on input data received and be further configured to provide one or more outputs that can be used to control or otherwise inform subsequent processing to be carried out by the processor 118 and/or other processors or circuitry with which processor 118 is communicatively coupled. Thus, the processor 118 reacts to specific input stimulus in a specific way and generates a corresponding output based on that input stimulus. In some example cases, the processor 118 can proceed through a sequence of logical transitions in which various internal register states and/or other bit cell states internal or external to the processor 118 can be set to logic high or logic low. As referred to herein, the processor 118 can be configured to execute a function where software is stored in a data store coupled to the processor 118, the software being configured to cause the processor 118 to proceed through a sequence of various logic decisions that result in the function being executed. The various components that are described herein as being executable by the processor 118 can be implemented in various forms of specialized hardware, software, or a combination thereof. For example, the processor 118 can be a digital signal processor (DSP) such as a 24-bit DSP. The processor 118 can be a multi-core processor, e.g., having two or more processing cores. The processor 118 can be an Advanced RISC Machine (ARM) processor such as a 32-bit ARM processor or a 64-bit ARM processor. The processor 118 can execute an embedded operating system, and include services provided by the operating system that can be used for file system manipulation, display & audio generation, basic networking, firewalling, data encryption and communications.

As noted above, an ambulatory medical device such as a WCD can be designed to include a digital front-end where analog signals sensed by skin-contacting electrode surfaces of a set of digital sensing electrodes are converted to digital signals for processing. Typical ambulatory medical devices with analog front-end configurations use circuitry to accommodate a signal from a high source impedance from the sensing electrode (e.g., having an internal impedance range from approximately 100 Kiloohms to one or more Megaohms). This high source impedance signal is processed and transmitted to a monitoring device such as processor 118 of the controller 100 as described above for further processing. In certain implementations, the monitoring device, or another similar processor such as a microprocessor or another dedicated processor operably coupled to the sensing electrodes, can be configured to receive a common noise signal from each of the sensing electrodes, sum the common noise signals, invert the summed common noise signals and feed the inverted signal back into the patient as a driven ground using, for example, a driven right leg circuit to cancel out common mode signals.

As noted above, FIG. 4 illustrates a sample architecture of a remote computing device such as monitoring server 308 as described above. As seen in FIG. 4, the monitoring server 308 can include a processor 402, a memory 404, a user interface 406, and a network interface 408.

In some implementations, the processor 402 includes one or more processors (or one or more processor cores) that each are configured to perform a series of instructions that result in manipulated data and/or control the operation of the other components of the monitoring server 308. In some implementations, when executing a specific process, the processor 402 can be configured to make specific logic-based determinations based on input data received and be further configured to provide one or more outputs that can be used to control or otherwise inform subsequent processing to be carried out by the processor 402 and/or other processors or circuitry with which processor 402 is communicatively coupled. Thus, the processor 402 reacts to specific input stimulus in a specific way and generates a corresponding output based on that input stimulus. In some example cases, the processor 402 can proceed through a sequence of logical transitions in which various internal register states and/or other bit cell states internal or external to the processor 402 can be set to logic high or logic low. As referred to herein, the processor 402 can be configured to execute a function where software is stored in a data store coupled to the processor 402, the software being configured to cause the processor 402 to proceed through a sequence of various logic decisions that result in the function being executed. The various components that are described herein as being executable by the processor 402 can be implemented in various forms of specialized hardware, software, or a combination thereof. The processor 402 can execute an embedded operating system, and include services provided by the operating system that can be used for file system manipulation, display & audio generation, basic networking, firewalling, data encryption and communications.

The memory 404 can include one or more of non-transitory computer-readable media, such as flash memory, solid state memory, magnetic memory, optical memory, cache memory, combinations thereof, and others. In certain examples, the user interface 406 can include one or more physical interface devices such as input devices, output devices, and combination input/output devices operably coupled to the user interface and a software stack configured to drive operation of the devices. These user interface elements can render visual, audio, and/or tactile content. In certain implementations, the user interface 406 can be configured to permit technicians or otherwise authorized users to perform a variety of system maintenance, monitoring, or new device/service actions. Such actions can include adding new patients for whom cardiac rehabilitation progress is to be monitored from one or more of a doctor, hospital, or other HCP computer network system, adding new devices associated with patients who are newly prescribed one or more cardiac monitoring and/or treatment devices, remotely changing the monitoring and/or treatment parameters of such devices, entering informational, reminder, and/or prescriptive messages that are transmitted to displays associated with the devices for viewing by patients or other persons associated with the patients, monitoring the operational status of devices, querying the devices for the most current ECG, physical activity, and/or other physiological information collected by the devices, remotely adding or changing one or more types of monitoring service implemented by the device (e.g., switching a cardiac monitoring only service to a cardiac monitoring and treatment service), querying a doctor, hospital or other HCP network system for updated information associated with a patient.

Figure 17A:
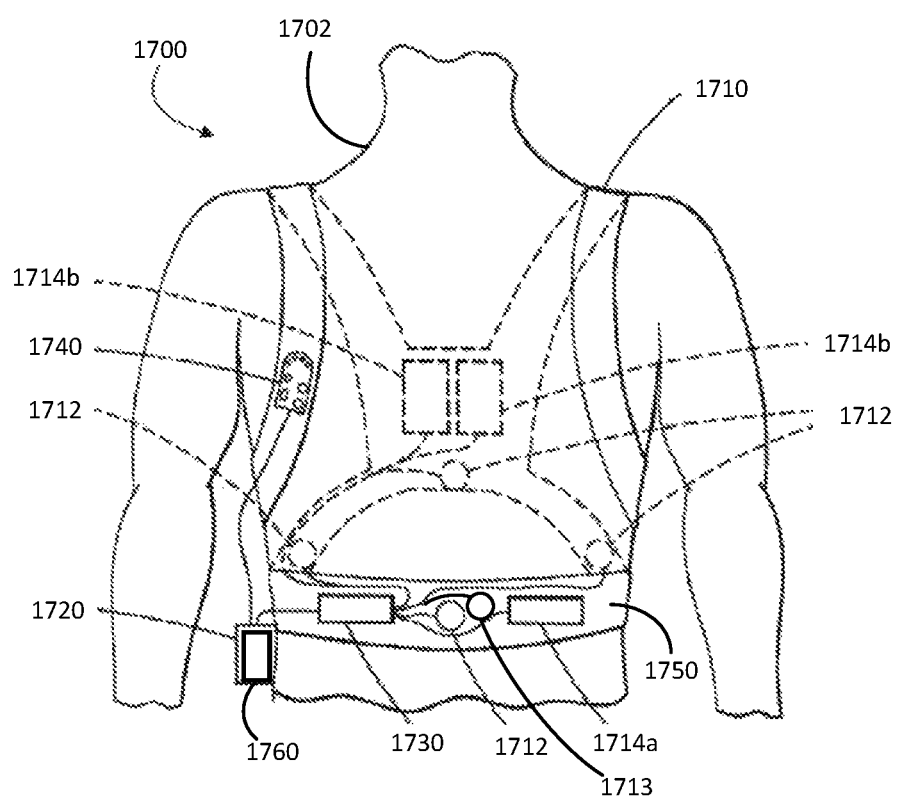

FIG. 17A illustrates an example medical device 1700 that is external, ambulatory, and wearable by a patient 1702, and configured to implement one or more configurations described herein. For example, the medical device 1700 can be a non-invasive medical device configured to be located substantially external to the patient. Such a medical device 1700 can be, for example, an ambulatory medical device that is capable of and designed for moving with the patient as the patient goes about his or her daily routine. For example, the medical device 1700 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 1700 can include one or more of the following: a garment 1710, one or more ECG sensing electrodes 1712, one or more non-ECG physiological sensors 1713, one or more therapy electrodes 1714a and 1714b (collectively referred to herein as therapy electrodes 1714), a medical device controller 1720 (e.g., controller 100 as described above in the discussion of FIG. 1), a connection pod 1730, a patient interface pod 1740, a belt 1750, or any combination of these. In some examples, at least some of the components of the medical device 1700 can be configured to be affixed to the garment 1710 (or in some examples, permanently integrated into the garment 1710), which can be worn about the patient's torso.

The medical device controller 1720 can be operatively coupled to the sensing electrodes 1712, which can be affixed to the garment 1710, e.g., assembled into the garment 1710 or removably attached to the garment, e.g., using hook and loop fasteners. In some implementations, the sensing electrodes 1712 can be permanently integrated into the garment 1710. The medical device controller 1720 can be operatively coupled to the therapy electrodes 1714. For example, the therapy electrodes 1714 can also be assembled into the garment 1710, or, in some implementations, the therapy electrodes 1714 can be permanently integrated into the garment 1710. In an example, the medical device controller 1720 includes a patient user interface 1760 to allow a patient interface with the externally-worn device. For example, the patient can use the patient user interface 1760 to respond to pre- and post-workout questions, prompts, and surveys as described herein.

Component configurations other than those shown in FIG. 17A are possible. For example, the sensing electrodes 1712 can be configured to be attached at various positions about the body of the patient 1702. The sensing electrodes 1712 can be operatively coupled to the medical device controller 1720 through the connection pod 1730. In some implementations, the sensing electrodes 1712 can be adhesively attached to the patient 1702. In some implementations, the sensing electrodes 1712 and at least one of the therapy electrodes 1714 can be included on a single integrated patch and adhesively applied to the patient's body.

The sensing electrodes 1712 can be configured to detect one or more cardiac signals. Examples of such signals include ECG signals and/or other sensed cardiac physiological signals from the patient. In certain examples, as described herein, the non-ECG physiological sensors 1713 are components such as accelerometers, vibrational sensors, and other measuring devices for recording additional non-ECG physiological parameters. For example, as described above, such non-ECG physiological sensors are configured to detect other types of patient physiological parameters and acoustic signals, such as tissue fluid levels, cardio-vibrations, lung vibrations, respiration vibrations, patient movement, etc.

In some examples, the therapy electrodes 1714 can also be configured to include sensors configured to detect ECG signals as well as other physiological signals of the patient. The connection pod 1730 can, in some examples, include a signal processor configured to amplify, filter, and digitize these cardiac signals prior to transmitting the cardiac signals to the medical device controller 1720. One or more of the therapy electrodes 1714 can be configured to deliver one or more therapeutic defibrillating shocks to the body of the patient 1702 when the medical device 1700 determines that such treatment is warranted based on the signals detected by the sensing electrodes 1712 and processed by the medical device controller 1720. Example therapy electrodes 1714 can include metal electrodes such as stainless-steel electrodes that include one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 1714 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device to convert the therapeutic medical device into a monitoring medical device for a specific use (e.g., for operating in a monitoring-only mode) or a patient. Alternatively, the optional therapeutic elements can be deactivated (e.g., via a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 17B:
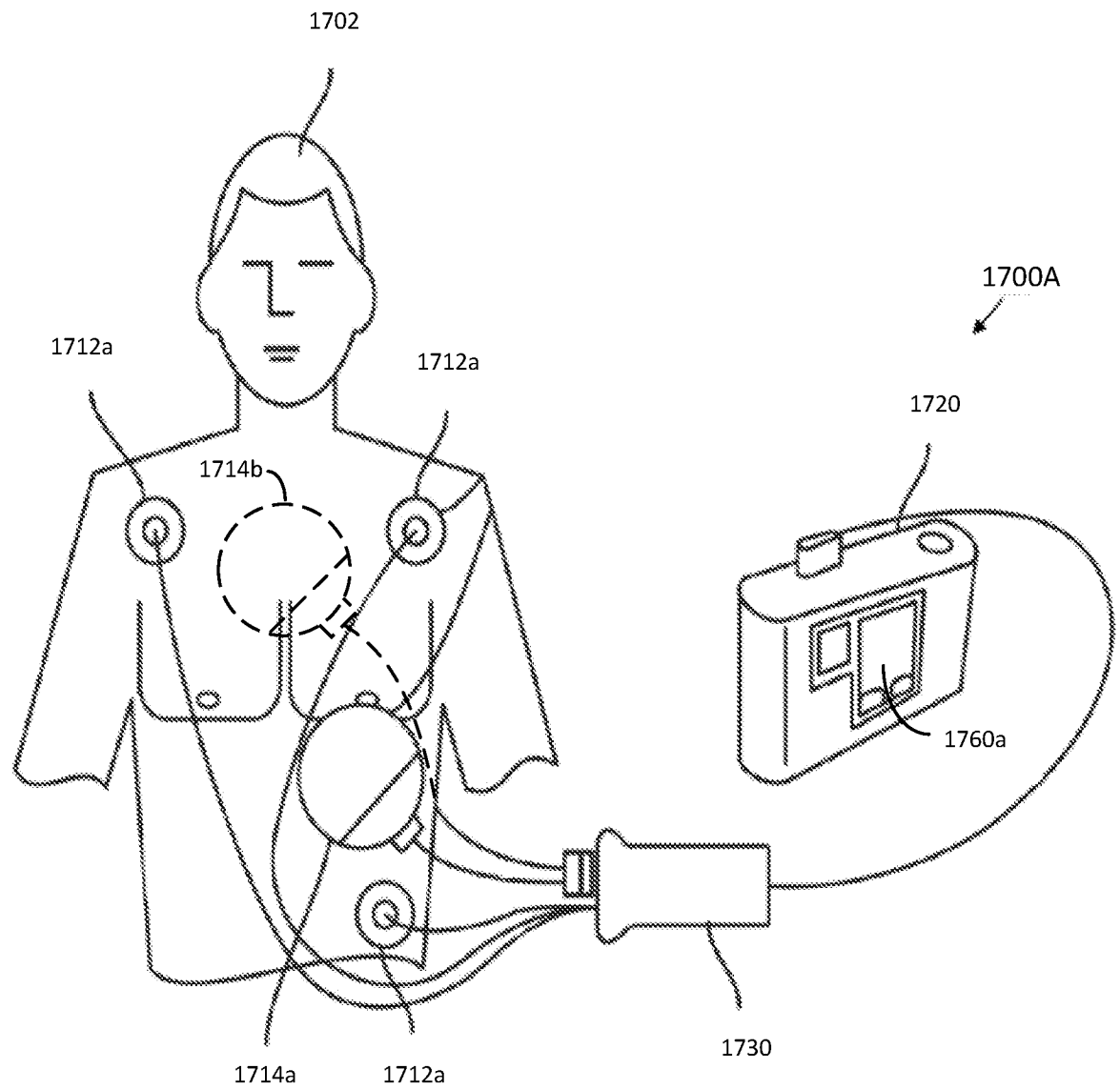

FIG. 17B illustrates a hospital wearable defibrillator 1700A that is external, ambulatory, and wearable by a patient 1702. Hospital wearable defibrillator 1700A can be configured in some implementations to provide pacing therapy, e.g., to treat bradycardia, tachycardia, and asystole conditions. The hospital wearable defibrillator 1700A can include one or more ECG sensing electrodes 1712a, one or more therapy electrodes 1714a and 1714b, a medical device controller 1720 and a connection pod 1730. For example, each of these components can be structured and function as like number components of the medical device 1700. For example, the electrodes 1712a, 1714a, 1714b can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. For example, the front adhesively attachable therapy electrode 1714a attaches to the front of the patient's torso to deliver pacing or defibrillating therapy. Similarly, the back adhesively attachable therapy electrode 1714b attaches to the back of the patient's torso. In an example scenario, at least three ECG adhesively attachable sensing electrodes 1712a can be attached to at least above the patient's chest near the right arm, above the patient's chest near the left arm, and towards the bottom of the patient's chest in a manner prescribed by a trained professional.

A patient being monitored by a hospital wearable defibrillator and/or pacing device may be confined to a hospital bed or room for a significant amount of time (e.g., 75% or more of the patient's stay in the hospital). As a result, a user interface 1760a can be configured to interact with a user other than the patient, e.g., a nurse, for device-related functions such as initial device baselining, setting and adjusting patient parameters, and changing the device batteries.

In some implementations, an example of a therapeutic medical device that includes a digital front-end in accordance with the systems and methods described herein can include a short-term defibrillator and/or pacing device. For example, such a short-term device can be prescribed by a physician for patients presenting with syncope. A wearable defibrillator can be configured to monitor patients presenting with syncope by, e.g., analyzing the patient's physiological and cardiac activity for aberrant patterns that can indicate abnormal physiological function. For example, such aberrant patterns can occur prior to, during, or after the onset of syncope. In such an example implementation of the short-term wearable defibrillator, the electrode assembly can be adhesively attached to the patient's skin and have a similar configuration as the hospital wearable defibrillator described above in connection with FIG. 17A.

Figure 17D:
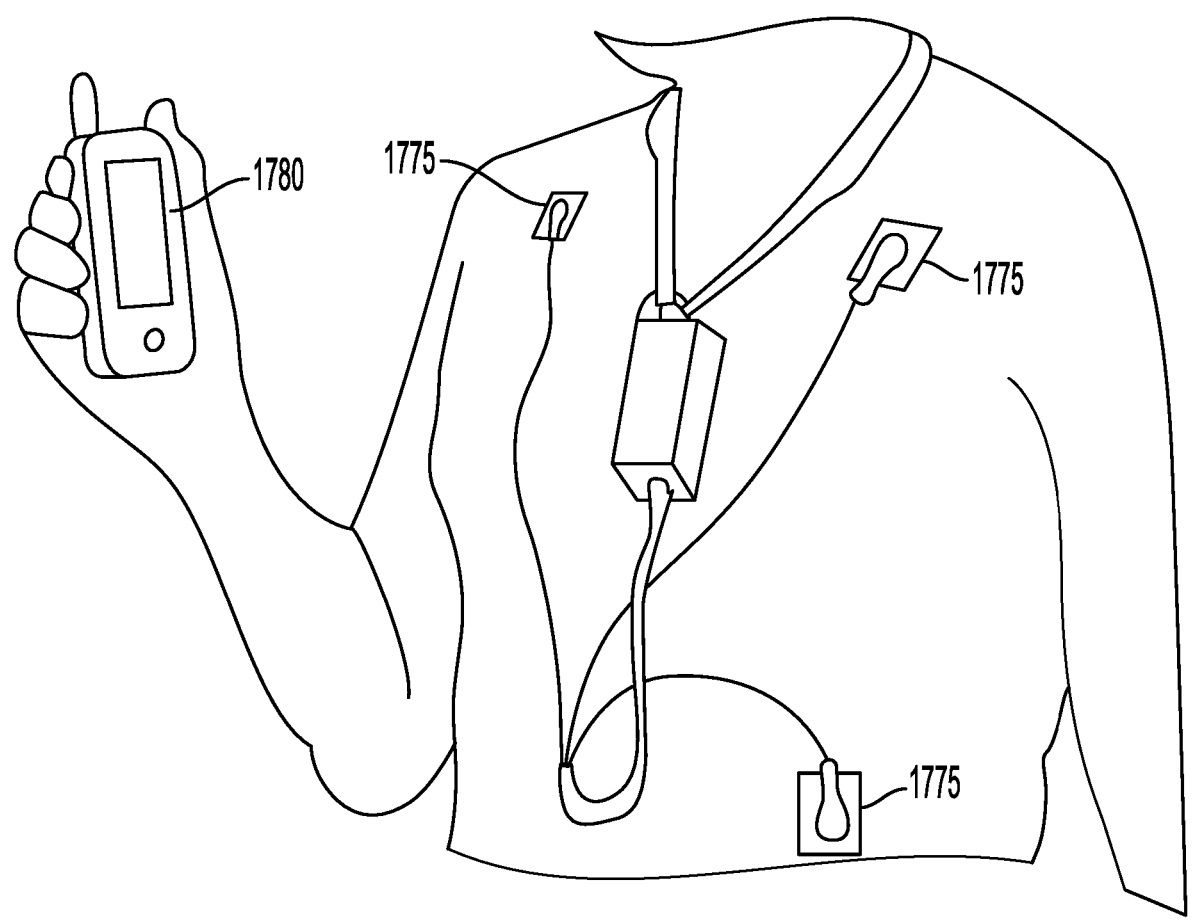

FIGS. 17C and 17D illustrate example wearable patient monitoring devices with no treatment or therapy functions. For example, such devices are configured to monitor one or more physiological parameters of a patient, e.g., for remotely monitoring and/or diagnosing a condition of the patient. For example, such physiological parameters can include a patient's ECG information, tissue (e.g., lung) fluid levels, cardio-vibrations (e.g., using accelerometers or microphones), and other related cardiac information. A cardiac monitoring device is a portable device that the patient can carry around as he or she goes about their daily routine.

Referring to FIG. 17C, an example wearable patient monitoring device 1700C can include tissue fluid monitors 1765 that use radio frequency (RF) based techniques to assess fluid levels and accumulation in a patient's body tissue. Such tissue fluid monitors 1765 can be configured to measure fluid content in the lungs, typically for diagnosis and follow-up of pulmonary edema or lung congestion in heart failure patients. The tissue fluid monitors 1765 can include one or more antennas configured to direct RF waves through a patient's tissue and measure output RF signals in response to the waves that have passed through the tissue. In certain implementations, the output RF signals include parameters indicative of a fluid level in the patient's tissue. In examples, device 1700C may be a cardiac monitoring device that also includes digital sensing electrodes 1770 for sensing ECG activity of the patient. Device 1700C can pre-process the ECG signals via one or more ECG processing and/or conditioning circuits such as an ADC, operational amplifiers, digital filters, signal amplifiers under control of a microprocessor. Device 1700C can transmit information descriptive of the ECG activity and/or tissue fluid levels via a network interface to a remote server for analysis.

Referring to FIG. 17D, another example wearable cardiac monitoring device can be attached to a patient via at least three adhesive digital cardiac sensing electrodes 1775 disposed about the patient's torso. The cardiac devices illustrated in FIGS. 17C and 17D are used in cardiac monitoring and telemetry and/or continuous cardiac event monitoring applications, e.g., in patient populations reporting irregular cardiac symptoms and/or conditions. These devices can transmit information descriptive of the ECG activity and/or tissue fluid levels via a network interface to a remote server for analysis. Example cardiac conditions that can be monitored include atrial fibrillation (AF), bradycardia, tachycardia, atrio-ventricular block, Lown-Ganong-Levine syndrome, atrial flutter, sino-atrial node dysfunction, cerebral ischemia, pause(s), and/or heart palpitations. For example, such patients may be prescribed a cardiac monitoring for an extended period of time, e.g., 10 to 30 days, or more. In some ambulatory cardiac monitoring and/or telemetry applications, a portable cardiac monitoring device can be configured to substantially continuously monitor the patient for a cardiac anomaly, and when such an anomaly is detected, the monitor can automatically send data relating to the anomaly to a remote server. The remote server may be located within a 24-hour manned monitoring center, where the data is interpreted by qualified, cardiac-trained reviewers and/or HCPs, and feedback provided to the patient and/or a designated HCP via detailed periodic or event-triggered reports. In certain cardiac event monitoring applications, the cardiac monitoring device is configured to allow the patient to manually press a button on the cardiac monitoring device to report a symptom. For example, a patient can report symptoms such as a skipped beat, shortness of breath, lightheadedness, racing heart rate, fatigue, fainting, chest discomfort, weakness, dizziness, and/or giddiness. The cardiac monitoring device can record predetermined physiologic parameters of the patient (e.g., ECG information) for a predetermined amount of time (e.g., 1-30 minutes before and 1-30 minutes after a reported symptom). As noted above, the cardiac monitoring device can be configured to monitor physiologic parameters of the patient other than cardiac related parameters. For example, the cardiac monitoring device can be configured to monitor, for example, cardio-vibrational signals (e.g., using accelerometers or microphones), pulmonary-vibrational signals, breath vibrations, sleep related parameters (e.g., snoring, sleep apnea), tissue fluids, among others.

In some examples, the devices described herein (e.g., FIGS. 17A-D) can communicate with a remote server via an intermediary device 1780 such as that shown in FIG. 17D. For instance, devices such as shown in FIGS. 17A-D can be configured to include a network interface communications capability as described herein in reference to, for example, FIG. 1.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the scope of the appended claims. For example, it is to be understood that the present disclosure contemplates that, to the extent possible, one or more features of any embodiment can be combined with one or more features of any other embodiment.

Other examples are within the scope of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A system for managing an individualized cardiac rehabilitation plan for an ambulatory cardiac rehabilitation patient, comprising:

an externally worn device configured to monitor cardiac activity of the patient, and a server in communication with the externally worn device, comprising a non-transitory computer-readable storage medium, and at least one server processor operably coupled to the computer-readable medium, wherein the at least one server processor is configured to receive one or more inputs from a healthcare provider related to the patient, develop a patient-specific cardiac rehabilitation plan based on the one or more inputs from the healthcare provider, the patient-specific cardiac rehabilitation plan comprising a plurality of exercise sessions, wherein each given exercise session comprises one or more physical activities for the patient to perform during the given exercise session, transmit the patient-specific cardiac rehabilitation plan to the externally worn device, receive patient data from the externally worn device after the externally worn device has started administering the patient-specific cardiac rehabilitation plan to the patient, record one or more status identifiers for each past exercise session based on the received patient data, wherein recording the one or more status identifiers for each past exercise session comprises recording a completed status identifier in response to the patient completing the given past exercise session or a non-completed status identifier in response to the patient not completing the given past exercise session, wherein the one or more status identifiers further comprise an over-performance status identifier recorded in response to the patient exceeding at least one requirement of the given past exercise session by at least a predetermined over-performance amount or an under-performance status identifier recorded in response to the patient satisfying at least one requirement of the given past exercise session and not meeting at least one additional requirement of the given past exercise session by at least a predetermined under-performance amount, adjust the patient-specific cardiac rehabilitation plan based on the one or more recorded status identifiers, wherein adjusting the patient-specific cardiac rehabilitation plan based on the one or more recorded status identifiers comprises performing at least a first adjustment based on an over-performance status identifier recorded for a past exercise session or performing at least a second adjustment based on an under-performance status identifier recorded for a past exercise session, and transmit the adjusted patient-specific cardiac rehabilitation plan to the externally worn device;

wherein the externally worn device is further configured to administer the patient-specific cardiac rehabilitation plan and the adjusted patient-specific cardiac rehabilitation plan;

monitor at least the patient's heart rate during a given exercise session;

determine whether the patient's monitored heart rate is below a minimum heart rate, above a maximum heart rate, or between the minimum heart rate and the maximum heart rate; and provide an alert based on the determination of whether the patient's heart rate is below the minimum heart rate, above the maximum heart rate, or between the minimum heart rate and the maximum heart rate.

2. The system of claim 1, wherein the one or more inputs from the healthcare provider, via a healthcare provider user interface, comprise a selection of a cardiac rehabilitation plan difficulty.

3. The system of claim 1, wherein the one or more inputs from the healthcare provider, via a healthcare provider user interface, comprise a selection of at least one of a frequency, a starting duration, an ending duration, or a target pace for an exercise session.

4. The system of claim 1, wherein the one or more inputs from the healthcare provider, via a healthcare provider user interface, comprise one or more thresholds for the patient-specific cardiac rehabilitation plan.

5. The system of claim 4, wherein the one or more thresholds comprises at least one of a shortness of breath prior to a given exercise session, chest pain prior to a given exercise session, fatigue prior to the given exercise session, a maximum heart rate during the given exercise session, or an average pace for the given exercise session.

6. The system of claim 4, wherein the at least one server processor is configured to develop the patient-specific cardiac rehabilitation plan based on the one or more inputs from the healthcare provider by selecting a difficulty ranking for each exercise session of the patient-specific cardiac rehabilitation plan based on the one or more thresholds.

7. The system of claim 4, wherein the at least one server processor is further configured to determine an average heart rate for the patient for a past exercise session; and adjust the patient-specific cardiac rehabilitation plan further based on the average heart rate for the patient for the past exercise session.

8. The system of claim 7, wherein the at least one server processor is configured to adjust the patient-specific cardiac rehabilitation plan further based on the patient data transgressing the one or more thresholds by at least one of stopping or rescheduling the given exercise session.

9. The system of claim 1, wherein the at least one server processor is configured to develop the patient-specific cardiac rehabilitation plan using one or more plan templates.

10. The system of claim 1, wherein the at least one server processor is configured to develop the patient-specific cardiac rehabilitation plan by selecting a pre-set plan based on the one or more inputs from the healthcare provider.

11. The system of claim 10, wherein the one or more inputs from the healthcare provider comprise a level of heart failure of the patient.

12. The system of claim 1, wherein the patient data comprises ECG information for the patient generated from the monitored cardiac activity of the patient.

13. The system of claim 1, wherein the externally worn device further comprises a motion sensor configured to monitor movement of the patient.

14. The system of claim 1, wherein the externally worn device further comprises an RF-based tissue fluid monitor configured to monitor tissue fluid levels of the patient.

15. The system of claim 1, wherein the externally worn device further comprises one or more non-ECG physiological sensors configured to monitor non-ECG physiological data for the patient;

wherein the patient data comprises non-ECG physiological information generated from the monitored non-ECG physiological data for the patient; and wherein the non-ECG physiological information for the patient comprises at least one of patient motion information, respiration information, lung fluid information, pulse information, or blood oxygenation information.

16. The system of claim 1, wherein the one or more physical activities for the patient to perform during the given exercise session comprise walking at a predetermined intensity level.

17. The system of claim 1, wherein each given exercise session further comprises at least one of a warm-up period or a cool-down period.

18. The system of claim 1, wherein the over-performance status identifier is recorded in response to the patient exceeding at least one of a required distance traveled or a required pace of movement for the given past exercise session by at least the predetermined over-performance amount.

19. The system of claim 1, wherein the under-performance status identifier is recorded in response to the patient satisfying a required duration for the given past exercise session and not meeting at least a required pace of movement for the given past exercise session by at least the predetermined under-performance amount.

* * * * *